US012053493B2

(12) United States Patent
Brodie et al.

(10) Patent No.: US 12,053,493 B2
(45) Date of Patent: Aug. 6, 2024

(54) MESENCHYMAL STEM CELLS POPULATIONS, THEIR PRODUCTS, AND USE THEREOF

(71) Applicant: EXOSTEM BIOTEC LTD., Tel Aviv (IL)

(72) Inventors: Chaya Brodie, Southfield, MI (US); Shlomit Brodie, Nof Ayalon (IL)

(73) Assignee: EXOSTEM BIOTEC LTD., Tel Aviv (IL)

(*) Notice: Subject to any disclaimer, the term of this patent is extended or adjusted under 35 U.S.C. 154(b) by 196 days.

(21) Appl. No.: 16/347,016

(22) PCT Filed: Nov. 2, 2017

(86) PCT No.: PCT/IL2017/051203
§ 371 (c)(1),
(2) Date: May 2, 2019

(87) PCT Pub. No.: WO2018/083700
PCT Pub. Date: May 11, 2018

(65) Prior Publication Data
US 2019/0269739 A1 Sep. 5, 2019

Related U.S. Application Data

(60) Provisional application No. 62/416,821, filed on Nov. 3, 2016.

(51) Int. Cl.
*A61K 35/50* (2015.01)
*A61K 35/28* (2015.01)
*A61P 3/10* (2006.01)
*A61P 21/00* (2006.01)
*A61P 25/00* (2006.01)
*A61P 35/00* (2006.01)
*A61P 37/00* (2006.01)
*C12N 5/00* (2006.01)
*C12N 5/0775* (2010.01)

(52) U.S. Cl.
CPC .............. *A61K 35/50* (2013.01); *A61K 35/28* (2013.01); *A61P 3/10* (2018.01); *A61P 21/00* (2018.01); *A61P 25/00* (2018.01); *A61P 35/00* (2018.01); *A61P 37/00* (2018.01); *C12N 5/0018* (2013.01); *C12N 5/0668* (2013.01)

(58) Field of Classification Search
CPC . A61K 35/50; A61P 3/10; A61P 21/00; A61P 25/00; A61P 35/00; C12N 5/0018; C12N 5/0668

See application file for complete search history.

(56) References Cited

U.S. PATENT DOCUMENTS 8,057,788 B2 * 11/2011 Hariri ................. C12N 5/0605
435/325
9,011,840 B2    4/2015 Bartholomew et al.
2012/0114618 A1   5/2012 Nolta et al.
2013/0195899 A1 * 8/2013 Ichim ................. A61K 39/0008
424/184.1
2015/0216899 A1   8/2015 Pusic et al.

FOREIGN PATENT DOCUMENTS

| CA | 2758120 C | 8/2014 | |
| EP | 2578677 A1 | 4/2013 | |
| EP | 2673636 A1 | 12/2013 | |
| EP | 2785359 B1 | 10/2014 | |
| KR | 20120096793 A | 8/2012 | |
| KR | 20140130592 A | 11/2014 | |
| WO | 2013093878 A1 | 6/2013 | |
| WO | WO-2013124816 A2 * | 8/2013 | ............. A61K 35/28 |
| WO | 2014013029 A1 | 1/2014 | |
| WO | 2014024183 A1 | 2/2014 | |
| WO | 2014054004 A1 | 4/2014 | |
| WO | 2015023901 A1 | 2/2015 | |
| WO | WO-2016086020 A1 * | 6/2016 | ........... A61K 31/191 |
| WO | 2016149358 A1 | 9/2016 | |
| WO | 2016157142 A1 | 10/2016 | |
| WO | 2017199250 A1 | 11/2017 | |

OTHER PUBLICATIONS

Uccelli A, Moretta L, Pistoia V. Mesenchymal stem cells in health and disease. Nat Rev Immunol. Sep. 2008;8(9):726-36. (Year: 2008).*
Yu B, Zhang X, Li X. Exosomes derived from mesenchymal stem cells. Int J Mol Sci. 2014; 15(3):4142-4157. (Year: 2014).*
Squillaro T, Peluso G, Galderisi U. Clinical Trials With Mesenchymal Stem Cells: An Update. Cell Transplant. 2016;25(5):829-48. Epub Sep. 29, 2015. (Year: 2015).*
Drela K, Siedlecka P, Sarnowska A, Domanska-Janik K. Human mesenchymal stem cells in the treatment of neurological diseases. Acta Neurobiol Exp (Wars). 2013;73(1):38-56. (Year: 2013).*
Zhang et al. Systemic administration of cell-free exosomes generated by human bone marrow derived mesenchymal stem cells cultured under 2D and 3D conditions improves functional recovery in rats after traumatic brain injury. Neurochem Int. Dec. 2017; 111: 69-81. Epub Aug. 15, 2016 (Year: 2016).*
Doeppner TR, Herz J, Görgens A, Schlechter J, Ludwig AK, Radtke S, de Miroschedji K, Horn PA, Giebel B, Hermann DM. Extracellular Vesicles Improve Post-Stroke Neuroregeneration and Prevent Postischemic Immunosuppression. Stem Cells Transl Med. Oct. 2015;4(10):1131-43. (Year: 2015).*
Ophelders DR, Wolfs TG, Jellema RK, Zwanenburg A, Andriessen P, Delhaas T, Ludwig AK, Radtke S, Peters V, Janssen L, Giebel B, Kramer BW. Mesenchymal Stromal Cell-Derived Extracellular Vesicles Protect the Fetal Brain After Hypoxia-Ischemia. Stem Cells Transl Med. Jun. 2016;5(6):754-63. (Year: 2016).*

(Continued)

Primary Examiner — Taeyoon Kim
(74) Attorney, Agent, or Firm — The Roy Gross Law Firm, LLC; Roy Gross

(57) ABSTRACT

The present invention provides pharmaceutical compositions comprising a mesenchymal stromal cell (MSC) population, extracellular vesicles secreted from said MSC population, and a combination thereof, and methods of use thereof in treatment of a disease or disorder.

18 Claims, 12 Drawing Sheets

(56) References Cited

OTHER PUBLICATIONS

Pawitan JA. Prospect of stem cell conditioned medium in regenerative medicine. Biomed Res Int. 2014;2014:965849. (Year: 2014).*
Chung S, Rho S, Kim G, Kim SR, Baek KH, Kang M, Lew H. Human umbilical cord blood mononuclear cells and chorionic plate-derived mesenchymal stem cells promote axon survival in a rat model of optic nerve crush injury. Int J Mol Med. 2016 (Year: 2016).*
Fischer UM, Harting MT, Jimenez F, et al. Pulmonary passage is a major obstacle for intravenous stem cell delivery: the pulmonary first-pass effect. Stem Cells Dev. 2009; 18(5):683-692. (Year: 2009).*
Ankrum JA, Ong JF, Karp JM. Mesenchymal stem cells: immune evasive, not immune privileged. Nat Biotechnol. Mar. 2014;32(3): 252-60. (Year: 2014).*
Kean TJ, Lin P, Caplan AI, Dennis JE. MSCs: Delivery Routes and Engraftment, Cell-Targeting Strategies, and Immune Modulation. Stem Cells Int. 2013;2013:732742. (Year: 2013).*
Anbari F, Khalili MA, Bahrami AR, et al. Intravenous transplantation of bone marrow mesenchymal stem cells promotes neural regeneration after traumatic brain injury. Neural Regen Res. 2014;9(9):919-923. (Year: 2014).*
Ziadlou R, Shahhoseini M, Safari F, Sayahpour FA, Nemati S, Eslaminejad MB. Comparative analysis of neural differentiation potential in human mesenchymal stem cells derived from chorion and adult bone marrow. Cell Tissue Res. Nov. 2015;362(2):367-77 (Year: 2015).*
Zhang J, Huang X, Wang H, Liu X, Zhang T, Wang Y, Hu D. The challenges and promises of allogeneic mesenchymal stem cells for use as a cell-based therapy. Stem Cell Res Ther. Dec. 1, 2015;6:234. (Year: 2015).*
Atouf F. Cell-Based Therapies Formulations: Unintended components. AAPS J. Jul. 2016; 18(4):844-8. (Year: 2016).*
Gonzalez et al. Chorion Mesenchymal Stem Cells Show Superior Differentiation, Immunosuppressive, and Angiogenic Potentials in Comparison With Haploidentical Maternal Placental Cells. Stem Cells Translational Medicine 2015;4:1109-1121 (Year: 2015).*
Marote et al. MSCs-Derived Exosomes: Cell-Secreted Nanovesicles with Regenerative Potential. Front. Pharmacol. 7:231, p. 1-8 (Year: 2016).*
Sarvar et al. Mesenchymal Stem Cell-Derived Exosomes: New Opportunity in Cell-Free Therapy. Adv Pharm Bull, 2016, 6(3), 293-299. (Year: 2016).*
Lopez-Verrilli et al. Mesenchymal Stem Cell-Derived Exosomes From Different Sources Selectively Promote Neuritic Outgrowth. Neuroscience 320 (2016) 129-139 (Year: 2016).*
M. H. Abumaree et al. "Human placental mesenchymal stem cells (pMSCs) modulate the immunopathogenesis process in experimental autoimmune encephalomyelitis (EAE)", Multiple Sclerosis Journal, vol. 21 Issue S11, p. 444, Sep. 30, 2015.
Indira Vishnubhatla et al., "The Development of Stem Cell-Derived Exosomes as a Cell-Free Regenerative Medicine", Journal of Circulating Biomarkers, vol. 3 No 2, 2014.
Xin Wei et al, "Mesenchymal stem cells: a new trend for cell therapy", Acta Pharmacol Sin. Jun. 2013;34(6):747-54.
International Search Report of PCT/IL2017/051203 Completed Feb. 11, 2018; Mailed Mar. 12, 2018 5 Pages.
Written Opinion of PCT/IL2017/051203 Completed Feb. 11, 2018; Mailed Mar. 12, 2018 7 Pages.

* cited by examiner

MESENCHYMAL STEM CELLS POPULATIONS, THEIR PRODUCTS, AND USE THEREOF

CROSS-REFERENCE TO RELATED APPLICATIONS

This application is a National Phase of PCT Patent Application No. PCT/IL2017/051203 having International filing date of Nov. 2, 2017, which claims the benefit of priority of U.S. Provisional Patent Application No. 62/416,821 filed on Nov. 3, 2016. The contents of the above applications are all incorporated by reference as if fully set forth herein in their entirety.

FIELD OF INVENTION

The present invention relates to specific mesenchymal stem cell populations, their secreted extracellular vesicles and other products and their uses for treating diseases in a subject.

BACKGROUND OF THE INVENTION

Mesenchymal stromal cells, also called mesenchymal stem cells (MSCs), are a type of adult stem cells that can be easily manipulated in in vitro conditions. Stem cells present in early embryonic stages are pluripotent, whereas MSCs exhibit more limited plasticity, differentiating mainly into osteoblasts, adipocytes and chondrocytes (mesodermal cells) and to some extent also to skeletal muscle and endothelial cells. MSCs are present in the bone marrow and adipose tissue, and are also present in peripheral blood, placenta, umbilical cord blood, dental pulp, and other tissues.

MSCs are attractive candidates for cell therapy and manipulation as they can easily be isolated from a patient's own tissues such as bone-marrow, adipose tissue or dental pulp, cultured in vitro, and autologously transplanted into patients. In addition, MSCs can be also obtained from tissues such as the Wharton's jelly of the umbilical cord and placenta and be used for allogeneic transplantation. MHC-II expression is relatively low or absent in MSCs, in particular those derived from umbilical cord and placenta, which allows them to be used with minimal complications and difficulties related to immune rejection of transplanted cells.

MSCs are characterized by high migratory potential and combined with their plasticity they can serve as an ideal tool for targeted therapeutic applications and tissue regeneration. MSCs have the capacity to migrate in response to signals produced by inflamed and injured tissues as well as by tumors. Thus, MSCs naturally migrate to the affected area of a diseased subject.

Great controversy, however, exists as to whether MSCs have a pro or anti-tumor role once they reach the tumor site. In some models, MSCs inhibit tumor growth (e.g. lung carcinoma, B16 melanoma) and in other models they were reported to enhance tumor growth (e.g. multiple myeloma, breast cancer). These differential effects are dependent on the tissue source of the MSCs, the tumor type and the factors that are involved in these differential effects are yet to be identified.

Understanding the MSC-tumor crosstalk can provide important information regarding MSC effects on tumor behavior and may have important implications for the choice of MSC source used for the treatment of various diseases. Thus, the secretome and various omics analyses of different sources and populations of MSCs, are of utmost important in understanding MSCs ability to induce immunomodulation and regenerative capacity in healthy individuals and in the context of the presence of lesions or tumor. Characterization of the MSCs' secretome and omics analyses may help determined their compatibility and potential for both therapeutic and regenerative potentials on the one hand and pro- or anti-tumor actions, on the other.

Communication between cells takes place via direct cell-to-cell contact or via the secretion of soluble factors. However, a novel mechanism that can operate over short and long distances has recently emerged, based on the release and uptake of extracellular vehicles (EVs). Extracellular vesicles are membrane-derived extracellular vesicles that can be divided into three main groups: exosomes, microextracellular vesicles and apoptotic bodies. Exosomes are small membrane extracellular vesicles of endocytic origin with a size of 50-100 nm. They can contain microRNAs (miRNA), long non-coding RNAs (lncRNA), mRNAs, DNA fragments, and proteins, which are shuttled from donor to recipient cells. Exosomes appear to play an important role in the exchange of information in the tumor microenvironment, as they have been shown to mediate transfer of oncogenic proteins between cancer cells. On the other hand, exosomes have also been shown to program the immune system to elicit an anti-tumor response.

In addition to their natural role in cell-cell interactions, exosomes can be loaded with various drugs and exogenous nucleic acids or proteins and deliver this cargo to different cells. Exosomes have multiple advantages over existing delivery vehicles for various therapeutics including RNA-based therapy. As they can be derived from a patient's own cells, they should be less immunogenic than any foreign delivery vehicle. More importantly, exosomes are natural carriers for miRNAs and other non-coding RNAs, and the direct membrane fusion with the target cell allows contents to be delivered directly into the cytosol. This makes exosomes an excellent delivery system for small molecules.

miRNAs induce gene silencing by partial sequence homology, thus a single miRNA can have hundreds of targets. The role of a miRNA, as an oncogene and/or tumor suppressor, is dependent on its mRNA targets. miRNAs are secreted through exosomes and play an important role in intracellular communication by mediating mRNA repression in neighboring or distant cells. Further, aberrantly expressed miRNAs have been described in various types of tumors. The expression and function of miRNAs have been studied with regards to tumorigenesis, patient prognosis, and as novel therapeutic targets. The most appealing advantage of using miRNAs for the treatment of cancer is their ability to affect multiple target genes in the context of a network, making them especially suitable to treat glioma as it is a complex heterogeneous tumor. Moreover, several in-vitro and pre-clinical studies demonstrated the therapeutic benefits of targeting miRNAs.

In addition to miRNAs, the human genome expresses tens of thousands of long non-coding RNAs (lncRNAs). These non-coding RNAs are >200 bases in length but lack significant open reading frame. lncRNAs exhibit diverse transcriptional patterns, exhibit tissue specificity and play important functions in various cellular processes in both physiological and pathological conditions.

There remains a need for a method of identifying, isolating and/or tailoring specific MSC populations and therapeutic effects. The miRNA, lncRNA and protein characteristics of these cells and their secretome provide information that allows for a more educated targeted and specific MSC therapy for a wide range of diseases.

SUMMARY OF THE INVENTION

The present invention provides compositions comprising different sources and subpopulations of mesenchymal stem cells (MSCs) and/or extracellular vesicles secreted from said MSCs, kits comprising same and therapeutic use thereof.

The present invention further relates to treating various diseases or conditions with MSCs having unique expression profiles disclosed herein as well as with extracellular vesicles secreted from said MSCs.

According to a first aspect there is provided a method of treating a disease or condition in a subject in need thereof, the method comprising:
  (a) providing an enriched population of chorionic placenta-derived mesenchymal stem cells (CH-MSCs); and
  (b) administering to the subject a pharmaceutical composition comprising a therapeutically effecting amount of at least one of:
    i. the CH-MSC population;
    ii. extracellular vesicles derived from the CH-MSC population;
    iii. conditioned media from the CH-MSC population; and
    iv. extracellular matrix secreted by the CH-MSC population;
  thereby treating the disease or condition.

According to another aspect, there is provided a method of selecting a mesenchymal stem cell (MSC) subpopulation, the method comprising:
  (a) providing MSCs; and
  (b) selecting at least one MSC expressing of at least one surface marker on the at least one MSC's surface, wherein expression of at least one of CD184, CD193, CD235a, CD318, CD255, CD268, fMLP, ITGA2, ITGA4, and CD326 indicates an MSC is an umbilical cord-derived MSC, expression of at least one of TCR alpha-beta, CD55, LIFR, ST6GALNACS, and MIC A/B indicates an MSC is a chorionic placenta-derived MSC, expression of at least one of CD24, CD48, CD66b, CD338, CD120b, CD268, FGFLR1, ITGA5, NES, and PDGFRAA indicates an MSC is a bone marrow-derived MSC, expression of at least one of CD84, PDGFRBB, and TNFRSF11B indicates an MSC is an adipose-derived MSC, and expression of CD157 indicates an MSC is an amniotic placenta-derived MSC;
  thereby selecting an MSC subpopulation.

According to another aspect, there is provided a pharmaceutical composition for use in treating a disease or condition comprising a pharmaceutically acceptable adjuvant, excipient or carrier and at least one of:
  (a) an isolated and enriched population of CH-MSCs;
  (b) extracellular vesicles derived from the CH-MSC population;
  (c) conditioned media from the CH-MSC population; and
  (d) extracellular matrix secreted by the CH-MSC population.

According to another aspect, there is provided a method of maintaining stem cells and primary cells in culture, the method comprising,
  (a) providing stem cells, primary cells or both;
  (b) growing the stem cells, primary cells or both in culture medium comprising extracellular vesicles derived from MSCs,
  thereby maintaining stem cells, primary cells or both in culture.

According to some embodiments, the disease or condition is selected from a neurological disease, a muscular disease, an autoimmune disease, an inflammatory disease, a digestive disease, an energy homeostasis disease, a fibrotic disease, aging, radiation induced injury, cell transplant rejection and a proliferative disease.

According to some embodiments, the neurological disease is selected from brain cancer, cancer metastasis to the brain, multiple sclerosis (MS), amyotrophic lateral sclerosis (ALS), Alzheimer's disease, Parkinson's disease, neurological injury, radiation induced injury to the brain, hypoxic injury to the brain and Rett syndrome.

According to some embodiments, the brain cancer is any one of an astrocytic tumor, a glioma, a medulloblastoma, a neuroblastoma and a meningioma. According to some embodiments the glioma is glioblastoma.

According to some embodiments, the muscular disease is selected from MS, a muscular dystrophy, muscle injury, muscle inflammation, cachexia and sarcopenia. According to some embodiments, the muscular dystrophy is Duchenne's muscular dystrophy (DMD), or Baker muscular dystrophy. According to some embodiments, the disease is a muscle disease and wherein the extracellular vesicles, conditioned media, extracellular matrix or a combination thereof comprise at least one of miR-29a, miR-29b, miR-29c and miR-656.

According to some embodiments, the autoimmune disease is selected from MS, diabetes, colitis, and Chron's disease.

According to some embodiments, the energy homeostasis disease is diabetes.

According to some embodiments, the digestive disease is selected from irritable bowel syndrome (IBD), Chron's disease, and colitis.

According to some embodiments, aging comprises at least one of skin aging, muscle aging, and brain aging.

According to some embodiments, the proliferative disease is cancer. According to some embodiments, the cancer is any one of brain cancer, metastasis to the brain, lung cancer, breast cancer, colon cancer, pancreatic cancer, prostate cancer, and head and neck cancer. According to some embodiments, the brain cancer is selected from glioma, medulloblastoma, neuroblastoma and meningioma. According to some embodiments, the glioma is glioblastoma. According to some embodiments, the MSC population, extracellular vesicles, conditioned media, extracellular matrix or a combination thereof comprise at least one of miR-145 and miR-656. According to some embodiments, the methods of the invention further comprise irradiating the subject.

According to some embodiments, the enriched population of CH-MSCs is substantially devoid of amniotic placenta-derived MSCs (AM-MSCs).

According to some embodiments, the providing comprises, selecting CH-MSCs from a mix of cells or placental tissue. According to some embodiments, the selecting comprises selecting at least one cell expressing at least one surface marker selected from TCR alpha-beta, CD55, LIFR, ST6GALNACS, and MIC A/B.

According to some embodiments, the administering comprises at least one of intravenous administration, intramuscular administration, intranasal administration, intrathecal administration, intrastriatal administration, intracranial administration, intraarterial administration, and subcutaneous administration.

According to some embodiments, the CH-MSC population is allogenic to the subject. According to some embodiments, the CH-MSC population is autologous to the subject.

According to some embodiments, the methods of the invention further comprise confirming expression of the at least one surface marker on the surface of the selected CH-MSC.

According to some embodiments, the methods of the invention further comprise culturing the MSC in MSC growth media.

According to some embodiments, the providing comprises providing tissue or a cell mixture and isolating MSCs from the tissue or cell mixture.

According to some embodiments, the isolating MSCs comprises isolation of cells expressing a plurality of surface marker selected from CD9, CD10, CD13, CD26, CD29, CD44, CD36, CD46, CD47, CD49a, CD49b, CD49c, CD49d, CD49e, CD50, CD51/61, CD54, CD55, CD58, CD59, CD61, CD63, CD71, CD73, CD81, CD83, CD87, CD90, CD91, CD95, CD97, CD98, CD99, CD105, CD108, CD109, CD140b, CD142, CD146, CD147, CD151, CD164, CD165, CD166, CD273, β2-microglobulin, HLA-A,B,C, HLA-A2, and STRO1.

According to some embodiments, the tissue is selected from placenta, umbilical cord, adipose tissue and bone marrow.

According to some embodiments, the methods of the invention further comprise confirming expression of the at least one surface marker on the surface of the selected MSC.

According to some embodiments, the culture medium comprises conditioned media from the MSC. According to some embodiments, the culture medium comprises extracellular matrix from the MSC.

According to some embodiments, the growing comprises coculture of the stem cells, primary cells or both with the MSC.

According to some embodiments, the methods of the invention further comprise growing the stem cells, primary cells or both in primary cell growth media.

According to some embodiments, the maintaining comprises extending survival of the stem cells, primary cells or both beyond survival of the cells in culture medium substantially devoid of extracellular vesicles from the MSC. According to some embodiments, the maintaining comprises culturing the stem cells, primary cells or both in vitro for at least 10 passages. According to some embodiments, the maintaining comprises the stem cells, primary cells or both retaining the ability to undergo both symmetric and asymmetric divisions.

According to some embodiments, the MSCs are umbilical cord-derived MSCs (UC-MSCs), CH-MSCs or a combination thereof. According to some embodiments, the MSCs are CH-MSCs.

According to some embodiments, the stem cell are cancer stem cells and the MSCs are bone marrow-derived MSCs, (BM-MSCs), adipose-derived MSCs (AD-MSCs), AM-MSCs, or a combination thereof.

According to another aspect, there is provided a pharmaceutical composition comprising at least one of: a mesenchymal stem cell (MSC) population, extracellular vesicles secreted from the MSC population, conditioned media from the MSC population and a combination thereof; the MSC population is characterized by an expression profile selected from any one of Tables 1-5.

According to some embodiments, the pharmaceutical compositions of the invention further comprise a pharmaceutically acceptable carrier.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
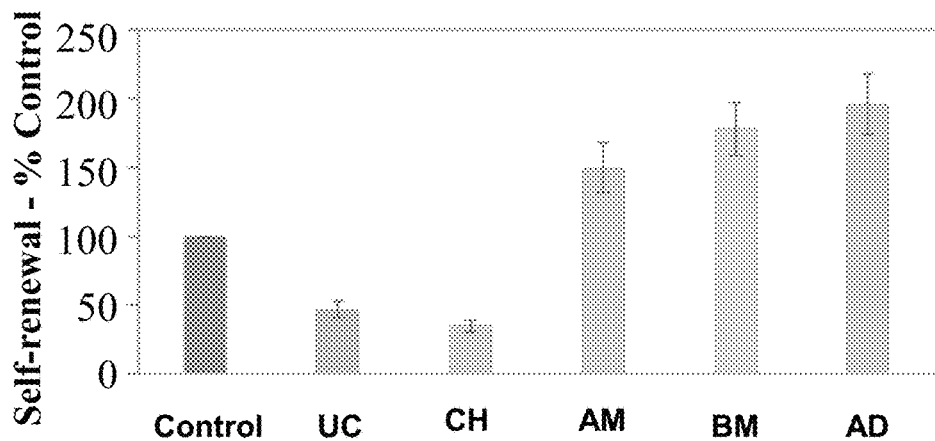
FIGS. 1A-C. Different MSC populations and their exosomes have opposite effects on glioma stem cells. (1A) A bar chart of self-renewal of glioblastoma cells after incubation with MSC subtypes. Self-renewal is represented as a percentage of the self-renewal when cells were incubated with control. (1B) A bar chart of self-renewal of glioblastoma cells after incubation with exosomes from various MSC subtypes. Self-renewal is represented as a percentage of the self-renewal when cells were incubated with control. (1C) A bar chart of relative mRNA expression levels of five mesenchymal and stemness markers in five MSC subtypes. Control expression was standardized to 1. The populations for each gene are presented in the following order: Control, UC, CH, AM, BM, AD.

According to some embodiments, the present invention provides MSC populations having specific and unique expression profile, and extracellular vesicles secreted from said MSC populations.

According to some embodiments, the present invention provides a method of treating a disease or condition in a subject in need thereof, by selecting or providing the MSC populations disclosed herein, and administering to said subject the MSC populations, extracellular vesicles secreted from the MSCs, conditioned media from the MSCs, extracellular matrix secreted by the MSCs or a combination thereof. In some embodiments, the provided MSC population is an isolated population. In some embodiments, the provided MSC population is an enriched population. In some embodiments, the provided MSC population is a substantially pure population. In some embodiments, the provided MSC population is an isolated and enriched population. In some embodiments, the provided MSC population is an isolated and substantially pure population.

The present invention is based, in part, on the unexpected finding that MSCs of different sources have a substantially varying expression profile, including coding and non-coding RNAs (e.g., miRNA and lncRNA), surface markers, and secretion of various factors, including but not limited to, exosomes and extracellular vesicles. Further, exosomes and extracellular vesicles secreted from various MSC subpopulation had unique and specific protein, surface markers and non-coding RNA profile.

The present invention is further based, in part, on the unexpected finding that specific MSC populations, as described herein, are amenable to treatment specific diseases and disorders, whereas other MSC populations were found to be ineffective, less effective or even promote the diseased state. As exemplified herein as a non-limiting example, only specific MSC populations were found to treat and inhibit glioblastoma, while other MSC populations did not and even promoted tumor growth.

"MSC", as used herein, refers to multipotent stromal stem cells having the ability to differentiate into osteoblasts, adipocytes, and chondroblasts as well as skeletal muscle and endothelial cells under some conditions. The term "multipotent" refers to stem cells which can give rise to many numbers of cell types. MSC are present in the bone marrow and adipose tissue, and are also present in peripheral blood, placenta, umbilical cord blood, dental pulp, among other tissues. In some embodiments, the MSCs described herein originates and/or is isolated from amniotic placenta, chorionic placenta, umbilical cord, bone marrow, adipose tissue, amniotic fluid, or dental pulp.

"MSC population", as used herein, refers to a population of MCSs having a unique profile, particularly an expression profile, including but not limited to, one or more unique proteins (e.g., surface markers and secreted proteins), genes, and one or more coding and non-coding RNAs (e.g., miRNA and lncRNA). An MSC population may also be characterized by extracellular vesicles having a unique profile, secreted from said MSCs such as exosomes and extracellular vesicles.

As specified herein below, the invention provides at least five MSC populations having a unique expression profile. Each MSC population may be isolated from a particular source or alternatively can be manipulated by various factors, known to a skilled artisan, to encompass and be defined by the unique profile as specified herein below.

A "population", as used herein, refers to a cell culture wherein at least 50%, at least 55%, at least 60%, at least 65%, at least 70%, at least 75%, at least 80%, at least 85%, at least 90%, at least 95%, at least 99%, or all cells of the culture have a similar profile. In some embodiments, a population is an enriched population. A "subpopulation", as used herein, refers to one of the MSC populations defined herein, being further manipulated by various growth conditions so as to endow a further unique expression profile to said MSCs. Each population consists of additional subpopulations exhibiting different combinations of expression profiles or different levels of expression. As used herein, "various growth conditions" includes but is not limited to enrichment by one or more protein (e.g., growth factors), one or more coding or non-coding RNAs, and growth in selective conditions and/or media (e.g., scaffold, hypoxia, glucose concentrations, co-cultures).

"Surface marker", as used herein, refers to any type of antigenic determinant on the surface of the plasma membrane of an MSC.

"Non-coding RNA", as used herein, refers to an RNA molecule that is not translated into a protein. Non-coding RNAs include microRNAs (miRs) and long non-coding RNAs (lncRNAs). Both of these non-coding RNAs are known to regulate mRNA stability and translation and thus protein expression. Sequences for the miRs presented herein can be found in resources such as the miR databases "miRbase" (www.mirbase.org) and miRDB (www.mirdb.org). Sequences of lncRNAs presented herein can be found in lncRNA databases such as lncRNAdb (www.lncrnadb.org) and LNCipedia (http://lncipedia.org).

"Extracellular vesicles", as used herein, refers to all cell-derived extracellular vesicles secreted from MSCs including but not limited to exosomes and microextracellular vesicles. "Exosome", as used herein, refers to cell-derived extracellular vesicles of endocytic origin, with a size of 50-100 nm, and secreted from MSCs. As a non-limiting embodiment, for the generation of exosomes cells are maintained with Opti-MEM and human serum albumin or 5% FBS that was depleted from exosomes. "Microextracellular vesicles", as used herein, refers to cell-derived extracellular vesicles originating from the plasma membrane, with a size of 100-1000 nm, and secreted from MSCs.

"Conditioned media", as used herein, refers to media in which the MSC populations of the invention have been growing. In some embodiments, the MSCs have been growing in the media for at least 1 hour, 2 hours, 4 hours, 6 hours, 12 hours, 18 hours, 24 hours, 36 hours, 48 hours, 60 hours, or 72 hours. Each possibility represents a separate embodiment of the invention. In some embodiments, the conditioned media comprises the extracellular vesicles secreted by the MSCs. In some embodiments, the conditioned media comprises proteins secreted by the MSCs. In some embodiments, the conditioned media comprises the secretome of the MSCs. As used herein, the term "secretome", refers to any substances secreted by a cell. In some embodiments, a secretome comprises any or all of secreted proteins, secreted nucleic acid molecules, and secreted vesicles.

"Extracellular matrix", and "ECM", as used herein, are interchangeable and refer to the extracellular molecules secreted by the MSCs which provide a structural and biochemical support to surrounding cells. In some embodiments, the ECM comprises membranes. In some embodiments, the ECM is structured.

Umbilical Cord-Derived MSC (UC-MSC) Population and Extracellular Vesicles Derived Therefrom In another embodiment, there is provided a pharmaceutical composition comprising UC-MSCs or UC-MSC-derived extracellular vesicles or conditioned media from UC-MSCs or a combination thereof, those MSCs and/or extracellular vesicles having an expression profile selected from:
(i) an MSC population comprising one or more lncRNAs selected from the group consisting of: DGCR5, H19, HAR1A, HOXA6AS, KRASP1, STOT3, TU-00176 and optionally GASS, MER11C, HOXA3AS and PCAT-32;
(ii) an MSC population comprising one or more miRNA selected form Table 10;
(iii) an MSC population comprising one of more secreted factors selected from the group consisting of VEGF, ANG, PDFRAA, NT-4, FGF4, TIMP1, IL-8, HAPLN1, DMP1, Stanniocalcin1, ADAM23, SCG5 and optionally BDNF and IGF-1;
(iv) an MSC population comprising one or more surface markers selected from the group consisting of: CD184, CD193, and CD235a, CD318, CD255, CD268, fMLP, ITGA2, ITGA4, and CD326;
(v) an MSC population comprising one of more of the upregulated genes selected from Table 11;
(vi) stemness and mesenchymal markers: low YKL40, SOX2, and KLF4.
(vii) MSC-derived extracellular vesicles comprising one or more proteins selected from the group consisting of: ATP1B3, ATPB1, ATPB3, CD47, CD55, BSG, CSPG4, EPHA2, GPC1, GPRC5A, MME, MMP14, MPZL1, NCSTN, PLAUR, PVR, SLC16A1, SLC1A3, SLC1A4, SLC1A5, SLC2A3, SLC39A14, and SLC7A1;
(viii) MSC-derived extracellular vesicles comprising one or more lncRNAs selected from the group consisting of: Y4 and optionally NEAT1 and PTENP1;
(ix) a combination thereof.

In some embodiments, the UC-MSC population may also express cell-derived extracellular vesicles comprising one or more proteins selected from the group consisting of: CASK, COL3A1, B2M, CDH2, CTNNA1, DLG1, EGFR, F3, FARP1, GPC1, CDH2, CTNNA1, HAPLN1, LAMB1, LAMB2, LAMPC1, LGALS3BP, LOXL2, MCAM, NID1, OLXNB2, S100A6, TNC, WNT5A, and PLXNB2.

In some embodiments, the present invention provides a method of treating a disease or disorder by administering a therapeutically acceptable amount of this pharmaceutical composition to a subject, thereby treating the disease. In some embodiments, the disease or disorder is selected from: brain cancers and brain metastasis thereof, diabetes, muscle diseases (e.g., DMD), ALS, multiple sclerosis (MS), Alzheimer's disease, Rett syndrome, autism, age-related disorders, allogenic transplantation, brain injury, spinal cord injury, cartilage injury, skeletal injury, cardiac diseases, graft vs host disease, rejection of allogeneic cell and tissue translations, radiation-induced injury, fibrosis disorders, asthma, autoimmune diseases, celiac disease, inflammatory bowel diseases, injuries, arthritis, atherosclerosis, allergies, myopathies, leukocyte defects, endocrine diseases, cystic fibrosis, Parkinson's disease, spinal cord injury, stroke, schizophrenia, drug addiction, cardiac disorders, orphan disorders in the CNS, cerebral palsy, vascular-induced dementia, epilepsy and neonatal ischemic injury.

Chorionic Placenta-Derived MSC (CH-MSC) Population and Extracellular Vesicles Derived Therefrom In another embodiment, there is provided a pharmaceutical composition comprising CH-MSCs or CH-MSC-derived extracellular vesicles or conditioned media from the CH-MSCs or a combination thereof, the CH-MSCs and/or extracellular vesicles having an expression profile selected from:
(i) an MSC population comprising one or more lncRNAs selected from the group consisting of: SCA8, TU00176, LINC-VLDLR and optionally ROR;
(ii) an MSC population comprising one or more miRNA selected form Table 10;
(iii) an MSC population comprising one of more secreted factors selected from the group consisting of HGF, wnt2, GDNF, Osteoprotegerin, MIP3α, NT-3, IL-6, IL-8, FGF7, NT-4, EGFL6 and optionally LIF and BDNF;
(iv) an MSC population comprising surface markers: TCR alpha-beta, CD55, LIFR, and ST6GALNACS;
(v) an MSC population comprising one of more of the upregulated genes selected from Table 11;

(vi) Stemness and mesenchymal markers: low YKL40 and KLF4.
(vii) MSC-derived extracellular vesicles comprising one or more proteins selected from the group consisting of: COL4A2, LGALS3, SCUBE1, LGAS3, and S100A10;
(viii) MSC-derived extracellular vesicles comprising one or more lncRNAs selected from the group consisting of BCMS, BIC, and optionally HAR1B;
(ix) a combination thereof.

In some embodiments, the CH-MSC population may also express cell-derived extracellular vesicles comprising one or more proteins selected from the group consisting of: CASK, COL3A1, B2M, CDH2, CTNNA1, DLG1, EGFR, F3, FARP1, GPC1, CDH2, CTNNA1, HAPLN1, LAMB1, LAMB2, LAMPC1, LGALS3BP, LOXL2, MCAM, NID1, OLXNB2, S100A6, TNC, WNT5A, and PLXNB2.

In some embodiments, the present invention provides a method of treating a disease or disorder by administering a therapeutically acceptable amount of this pharmaceutical composition to a subject, thereby treating the disease. In some embodiments, the disease or disorder is selected from: brain cancers and brain metastasis thereof, diabetes, muscle diseases (e.g., DMD), ALS, multiple sclerosis (MS), Alzheimer's disease, Rett syndrome, autism, age-related disorders, allogenic transplantation, brain injury, spinal cord injury, cartilage injury, skeletal injury, cardiac diseases, graft vs host disease, rejection of allogeneic cell and tissue translations, radiation-induced injury, fibrosis disorders, asthma, autoimmune diseases, celiac disease, inflammatory bowel diseases, injuries, arthritis, atherosclerosis, allergies, myopathies, leukocyte defects, endocrine diseases, cystic fibrosis, Parkinson's disease, spinal cord injury, stroke, schizophrenia, drug addiction, cardiac disorders, orphan disorders in the CNS, cerebral palsy, vascular-induced dementia, epilepsy and neonatal ischemic injury.

In some embodiments, UC- and CH-MSCs, and extracellular vesicles obtained from these cells, can be used as off the shelf treatments and can be maintained frozen in liquid nitrogen and thawed just before use.

Bone Marrow-Derived MSC (BM-MSC) Population and Extracellular Vesicles Derived Therefrom In another embodiment, there is provided a pharmaceutical composition comprising a BM-MSC population or BM-MSC-derived extracellular vesicles or conditioned media from BM-MSCs or a combination thereof, the BM-MSCs and/or extracellular vesicles having an expression profile selected from:
(i) an MSC population comprising one or more lncRNAs selected from the group consisting of: aHIF, ANRIL, HOTAIR, PANDA, SAF and optionally LIT and HOXA3AS;
(ii) an MSC population comprising one or more miRNAs selected form Table 10;
(iii) an MSC population comprising one of more secreted factors selected from the group consisting of IGFBP2, IL-4, ALPL, TSLC1, PGF, COL5A3, DSG2, PENK precursor and optionally TGFβ, IGF-1.
(iv) an MSC population comprising one or more surface markers selected from the group consisting of: CD48, CD66b, CD338, CD120b, CD268, FGFLR1 and ITGA5, NES, PDGFRAA;
(v) an MSC population comprising one of more of the upregulated genes selected from Table 11;
(vi) Stemness and mesenchymal markers: high YKL40, low SOX2.
(vii) MSC-derived extracellular vesicles comprising one or more proteins selected from the group consisting of: CACNA2D1, CLTC, CORO1C, DMBT1, IGHA1, and IGHA2;
(viii) MSC-derived extracellular vesicles comprising one or more lncRNAs selected from the group consisting of: BC017743, BIC and optionally TUG, and NEAT1; and
(ix) a combination thereof.

In some embodiments, the present invention provides a method of treating a disease or disorder by administering a therapeutically acceptable amount of this pharmaceutical composition to a subject, thereby treating the disease. In some embodiments, the disease is selected from: muscle diseases, skeletal diseases, bone injury, cartilage injury, brain injury, spinal cord injury, diabetes, multiple sclerosis (MS), orphan disorders in the CNS, cerebral palsy, neonatal ischemic injury, graft vs host disease and radiation-induced injury.

Adipose-Derived MSC (AD-MSC) Population and Extracellular Vesicles Derived Therefrom In another embodiment, there is provided a pharmaceutical composition comprising a AD-MSC population or AD-MSC-derived extracellular vesicles, or conditioned media from AD-MSCs or a combination thereof, the AD-MSCs and/or extracellular vesicles having an expression profile selected from:
(i) an MSC population optionally comprising lncRNA PCAT-29;
(ii) an MSC population comprising one or more miRNAs selected form Table 10;
(iii) an MSC population comprising one of more secreted factors selected from the group consisting of: IL-4, CCL2, CFRP1, COMP, CTSK, MFAP5, MMP1, CXCL6, IGFBP6 and optionally TGFβ and GDNF;
(iv) an MSC population comprising one or more surface markers selected from: CD84, PDGFRBB, and TNFRSF11B;
(v) an MSC population comprising one of more of the upregulated genes selected from Table 11;
(vi) Stemness and mesenchymal markers: intermediate YKL40, high SOX2, and KLF4.
(vii) MSC-derived extracellular vesicles comprising one or more proteins selected from the group consisting of: SOD3, TGM3, IGF2R, FGFR1, and ADAMTS13;
(viii) MSC-derived extracellular vesicles comprising one or more lncRNAs selected from the group consisting of: AAA1, GOMAFU, and HOTAIR; and
(ix) a combination thereof.

In some embodiments, the present invention provides a method of treating a disease or disorder by administering a therapeutically acceptable amount of this pharmaceutical composition to a subject, thereby treating the disease. In some embodiments, the disease is selected from: diabetes, muscle diseases, skeletal diseases, bone injury and cartilage injury.

Amniotic Placenta-Derived MSC (AM-MSC) Population and Extracellular Vesicles Derived Therefrom In another embodiment, there is provided a pharmaceutical composition comprising an AM-MSC population or AM-MSC-derived extracellular vesicles or conditioned media from AM-MSCs or a combination thereof, the AM-MSCs and/or extracellular vesicles having an expression profile selected from:
  (i) an MSC population comprising one or more lncRNAs selected from the group consisting of: GOMAFU, NDM29, 7SK, BIC, CMPDHOAIR, H19-AS and optionally 21A;
  (ii) an MSC population comprising one or more miRNAs selected form Table 10;
  (iii) an MSC population comprising one of more secreted factors selected from the group consisting of: RANTES, VTN, MFAP5, FMOD, IL-4, PRSS35, NPTX2, CPA4, GLS, Neuromedin and optionally LIF, BDNF, GDNF and VEGF;
  (iv) an MSC population comprising CD157 surface marker;
  (v) an MSC population comprising one of more of the upregulated genes selected from Table 11;
  (vi) Stemness and mesenchymal markers: high YKL40 and SOX2.
  (vii) MSC-derived extracellular vesicles comprising one or more lncRNAs selected from the group consisting of: aHIF, CMPD, DISC2, HOTTIP, HULC, KRASP1, MALAT1, MEG3, PCGEM1, SCA8, and optionally TUG and BACE1AS; and
  (viii) a combination thereof.

In some embodiments, the present invention provides a method of treating a disease or disorder by administering a therapeutically acceptable amount of this pharmaceutical composition to a subject, thereby treating the disease. In some embodiments, the disease is selected from: Alzheimer's disease, bone injury, cartilage injury.

In some embodiments, the AD- and AM-MSCs may be used to promote the generation of human tumors in models such as mice. In some embodiments, this is achieved by enhancing the epithelial to mesenchymal transition (EMT) of the tumor cells in culture or in vivo. In some embodiments, the model used is non-immune compromised. Typically, human xenografts are generated in immune-compromised mice to prevent the risk of tumor rejection. As detailed herein, AD- and AM-MSCs prevent human cell rejection in non-immune compromised mice and in addition enhance tumor engraftments and growth.

The term "EMT" as used herein refers to a process by which cells lose their epithelial cell characteristics, such as cell polarity and cell adhesion, and gain mesenchymal cell characteristics such as migratory and invasive properties. EMT of tumor cells is known to promote cancer progression and metastasis. A similar process is also known for non-epithelial tumors and is also considered a mesenchymal transformation.

The terms "immune compromised", "immunocompromised" or "immunodeficient" as used herein refers to mice, or cells derived from mice, that have an impaired immune system. This impairment can be in the form of impaired innate immune response, impaired adaptive immune response, or both. Examples of such mice are common in the literature and can include but are not limited to Nude mice, Scid mice, Rag mice, NSG mice and NRG mice.

Dental Pulp-Derived MSC (DP-MSC) Population and Extracellular Vesicles Derived Therefrom In another embodiment, there is provided a pharmaceutical composition comprising a DP-MSC population or DP-MSC-derived extracellular vesicles or conditioned media from DP-MSCs or a combination thereof, the DP-MSCs or their extracellular vesicles having an expression profile selected from:
  (i) an MSC population comprising enrichment one or more lncRNAs selected from the group consisting of: PCAT-1, IPW, MALAT-1, ST7OT1 and optionally LIT;
  (ii) an MSC population comprising one of more secreted factors selected from the group consisting of: BDNF, GDNF;
  (iii) Stemness and mesenchymal markers: no YKL40, high SOX2;
  (iv) MSC-derived extracellular vesicles comprising one or more lncRNAs selected from the group consisting of: EGO, H19-AS, LOC285149 LOC285194, LincRNA-VLDLR, LincRNA-SFMBT2, PSF-inhibiting RNA, ROR, ST70T3, UCA1, Y5 and optionally HAR1B; and
  (v) a combination thereof.

In some embodiments, the present invention provides a method of treating a disease or disorder by administering a therapeutically acceptable amount of this pharmaceutical composition to a subject, thereby treating the disease. In some embodiments, the disease is selected from: Alzheimer's disease, neurological disorders, cancer, bone injury, cartilage injury, bone engraftment in tooth transplantation.

Exfoliated Deciduous Teeth-Derived MSC (DD-MSC) Population and Extracellular Vesicles Derived Therefrom In another embodiment, there is provided a pharmaceutical composition comprising a DD-MS) population or DD-MSC-derived extracellular vesicles or conditioned media from DD-MSCs or a combination thereof, the DD-MSCs or extracellular vesicles having an expression profile selected from:
  (i) an MSC population comprising one or more lncRNAs selected from the group consisting of: BC017743, BC04343C, HOTAIRM, Y3, Y5ST7OT4 and optionally GASS, ROR and PCAT-32;
  (ii) an MSC population comprising one of more secreted factors selected from the group consisting of: NGF, IGF-1, GDNF and BDNF;
  (iii) Stemness and mesenchymal markers: no YKL40 and KLF4, high SOX2;
  (iv) MSC-derived extracellular vesicles comprising one or more lncRNAs selected from the group consisting of: BC200 and optionally BACE1AS; and
  (v) a combination thereof.

In some embodiments, the present invention provides a method of treating a disease or disorder by administering a therapeutically acceptable amount of this pharmaceutical composition to a subject, thereby treating the disease. In some embodiments, the disease is selected from: Alzheimer's disease, neurological disorders, cancer, bone injury, cartilage injury, and bone engraftment in tooth transplantation.

Dental Follicle-Derived MSC (DF-MSC) Population and Extracellular Vesicles Derived Therefrom In another embodiment, there is provided a pharmaceutical composition comprising a DF-MSC population or DF-MSC-derived extracellular vesicles, or conditioned media from DF-MSCs or a combination thereof, the DF-MSCs or extracellular vesicles having an expression profile selected from:
  (i) an MSC population comprising one or more lncRNAs selected from the group consisting of: DLG2AS, HULC, IGF2AS, UCA1, WT-1AS and optionally 21A, HOXA3AS and MER11C;
  (ii) an MSC population comprising one of more secreted factors selected from the group consisting of: NGF
  (iii) Stemness and mesenchymal markers: no YKL40 and SOX2, KLF4, Notch1
  (iv) MSC-derived extracellular vesicles comprising one or more lncRNAs selected from the group consisting of: LUST, PCAT-1, PCAT-29, Y3, Tu_0017629 and optionally PTENP1; and
  (v) a combination thereof.

In some embodiments, the present invention provides a method of treating a disease or disorder by administering a therapeutically effective amount of this pharmaceutical composition to a subject, thereby treating the disease. In some embodiments, the disease is selected from: Alzheimer's disease, neurological disorders, cancer, bone injury, cartilage injury, and bone engraftment in tooth transplantation.

Cell Selection

By another aspect there is provided a method of selecting a mesenchymal stem cell (MSC) from a mixture of cells, the method comprising:
  a. providing a mixture of cells comprising at least one MSC; and
  b. selecting at least one cell expression a plurality of surface markers selected from: CD9, CD10, CD13, CD26, CD29, CD44, CD36, CD46, CD47, CD49a, CD49b, CD49c, CD49d, CD49e, CD50, CD51/61, CD54, CD55, CD58, CD59, CD61, CD63, CD71, CD73, CD81, CD83, CD87, CD90, CD91, CD95, CD97, CD98, CD99, CD105, CD108, CD109, CD140b, CD142, CD146, CD147, CD151, CD164, CD165, CD166, CD273, β2-microglobulin, HLA-A,B,C, HLA-A2, and STRO1;
  thereby selecting an MSC from a mixture of cells.

By another aspect there is provided a method of selecting a mesenchymal stem cell (MSC) subpopulation, the method comprising:
  a. providing MSCs;
  b. selecting at least one MSC expressing of at least one surface marker on said at least one MSC's surface, wherein expression of at least one of CD184, CD193, CD235a, CD318, CD255, CD268, fMLP, ITGA2, ITGA4, and CD326 indicates an MSC is an umbilical cord-derived MSC, expression of at least one of TCR alpha-beta, CD55, LIFR, ST6GALNACS, and MIC A/B indicates an MSC is a chorionic placenta-derived MSC, expression of at least one of CD24, CD48, CD66b, CD338, CD120b, CD268, FGFLR1, ITGA5, NES, and PDGFRAA indicates an MSC is a bone marrow-derived MSC, expression of at least one of CD84, PDGFRBB, and TNFRSF11B indicates an MSC is an adipose-derived MSC, and expression of CD157 indicates an MSC is an amniotic placenta-derived MSC; and
  c. selecting at least one MSC with a desired tissue of origin;
  thereby selecting an MSC subpopulation.

In some embodiments, the mixture of cells is in culture. In some embodiments, the mixture of cells is part or all of a tissue or organ. In some embodiments, the tissue is selected from placenta, umbilical cord, adipose tissue and bone marrow. In some embodiments, the tissue is placenta and the methods of the invention allow for selection of only CH-MSCs or AM-MSCs.

Therapeutic Use

By another aspect there is provide a method of treating a disease or condition in a subject in need thereof, the method comprising:
  a. providing an isolated population of MSCs; and
  b. administering to the subject a pharmaceutical composition comprising a therapeutically effective amount of at least one of:
    i. the isolated MSC population;
    ii. extracellular vesicles derived from the isolated MSC population;
    iii. conditioned media from the isolated MSC population; and
    iv. extracellular matrix secreted by the isolated MSC population;
  thereby treating the disease or condition.

By another aspect there is provide a method of treating a disease or condition in a subject in need thereof, the method comprising:
  a. providing an isolated population of CH-MSCs; and
  b. administering to the subject a pharmaceutical composition comprising a therapeutically effective amount of at least one of:
    i. the isolated CH-MSC population;
    ii. extracellular vesicles derived from the isolated CH-MSC population;
    iii. conditioned media from the isolated CH-MSC population; and
    iv. extracellular matrix secreted by the isolated CH-MSC population;
  thereby treating the disease or condition.

As used herein, the term "isolated" refers to a population that has been selected from a mixture of cells, a tissue, or an organ. In some embodiments, an isolated population is an enriched population. In some embodiments, an isolated population is a pure or substantially pure population. In some embodiments, the population is isolated from any one of umbilical cord, placenta, bone marrow, adipose tissue, dental pulp, teeth, and dental follicles. In some embodiments, the isolated population is pure from non-MSC cells. In some embodiments, the isolated population is pure from MSCs derived from a different tissue. In some embodiments, the isolated population is pure from a different MSC population as described herein. In some embodiments, the CH-MSC population is isolated from placenta. In some embodiments, the placenta comprises CH-MSCs and AM-MSCs. In some embodiments, the isolated CH-MSC population is enriched in CH-MSCS. In some embodiments, the isolated CH-MSC population is devoid or substantially devoid from AM-MSCs. In some embodiments, the isolated CH-MSC population is devoid or substantially devoid from non-MSC placental cells. In some embodiments, the isolated CH-MSC population is devoid or substantially devoid from non-MSC placental cells and AM-MSCs.

In some embodiments, the enriched CH-MSC population comprises at least 50%, 60%, 70%, 80%, 90%, 95%, 97%, 99% or 100% CH-MSCs. Each possibility represents a separate embodiment of the invention.

As used herein, "substantially devoid" refers to have only a very small contamination of undesired cells. In some embodiments, a substantially pure population has less than 10%, 9%, 8%, 7%, 6%, 5%, 4%, 3%, 2%, 1%, 0.5%. 0.1%, 0.05% or 0.01% contaminating cells. Each possibility represents a separate embodiment of the invention.

In some embodiments, the providing comprises selecting an MSC population from a mixture of cells, a tissue or an organ. In some embodiments, the selecting comprises measuring expression of at least one surface marker on the surface of a cell of the mixture of cells, tissue or organ wherein expression of at least one of CD184, CD193, CD235a, CD318, CD255, CD268, fMLP, ITGA2, ITGA4, and CD326 indicates an MSC is an umbilical cord-derived MSC, expression of at least one of TCR alpha-beta, CD55, LIFR, ST6GALNACS, and MIC A/B indicates an MSC is a chorionic placenta-derived MSC, expression of at least one of CD24, CD48, CD66b, CD338, CD120b, CD268, FGFLR1, ITGA5, NES, and PDGFRAA indicates an MSC is a bone marrow-derived MSC, expression of at least one of CD84, PDGFRBB, and TNFRSF11B indicates an MSC is an adipose-derived MSC, and expression of CD157 indicates an MSC is an amniotic placenta-derived MSC.

In some embodiments, the providing comprises selecting CH-MSCs from a mix of cells or placental tissue. In some embodiments, the selecting comprises selected at least one cell expressing at least one surface marker selected from TCR alpha-beta, CD55, LIFR, ST6GALNACS, and MIC A/B indicates the cell is a CH-MSC. In some embodiments, the methods of the invention further comprise confirming expression of the at least one surface marker on the surface of the selected CH-MSC.

In some embodiments, providing comprises culturing the MSCs. In some embodiments, the culturing is in standard media for adherent cells. In some embodiments, the culturing is in MSC growth media. In some embodiments, the culturing is in specific growth media for the tissue of origin of the MSCs.

In some embodiments, the providing comprises providing a mixture of cells, tissue or an organ and isolated MSCs from the mixture, tissue or organ. In some embodiments, isolating MSCs comprises isolation of cells expressing a plurality of surface markers selected from CD9, CD10, CD13, CD26, CD29, CD44, CD36, CD46, CD47, CD49a, CD49b, CD49c, CD49d, CD49e, CD50, CD51/61, CD54, CD55, CD58, CD59, CD61, CD63, CD71, CD73, CD81, CD83, CD87, CD90, CD91, CD95, CD97, CD98, CD99, CD105, CD108, CD109, CD140b, CD142, CD146, CD147, CD151, CD164, CD165, CD166, CD273, β2-microglobulin, HLA-A,B,C, HLA-A2, and STRO1.

In some embodiments, the disease or condition is selected from a neurological disease, a muscular disease, an autoimmune disease, an inflammatory disease, a digestive disease, an energy homeostasis disease, aging, radiation induced injury, cell transplant rejection and a proliferative disease. In some embodiments, the disease or condition is a neurological disease. In some embodiments, the disease or condition is a muscular disease. In some embodiments, the disease or condition is a neuro-muscular disease. In some embodiments, the disease or condition is aging. In some embodiments, the disease or condition is radiation induced injury. In some embodiments, the disease or condition is cell transplant rejection. In some embodiments, the disease or condition is a proliferative disease.

In some embodiments, the proliferative disease is cancer. The term "cancer" refers to any type of cancer. In some embodiments, the cancer is brain cancer. In some embodiments, the brain cancer is selected from an astrocytic tumor, a glioma, a medulloblastoma, neuroblastoma and a meningioma. In some embodiments, the brain cancer is glioblastoma (GBM). In some embodiments, the glioma is GBM. In some embodiments, the astrocytic tumor is GBM. In some embodiments, the cancer is any one of: brain cancer, metastasis to the brain, breast cancer, lung cancer, head and neck cancer, colon cancer, pancreatic cancer, and prostate cancer.

The term "brain metastasis" refers to tumor cells that have spread to the brain from primary tumors in other organs in the body (such as lung, breast, melanoma, colon, and liver). Metastatic tumors represent the most common mass lesions in the brain.

In some embodiments, the cancer is any one of breast cancer, lung cancer, neuroblastoma and pancreatic cancer and the MSC population used to produce the pharmaceutical composition is UC-MSCs. In some embodiments, the cancer is any one of colon cancer, prostate cancer, metastasis to the brain, glioma, meningioma, medulloblastoma, or head and neck cancer and the MSC population used to produce the pharmaceutical composition is CH-MSCs.

In some embodiments, the disease is cancer and the CH-MSC population, extracellular vesicles, conditioned media, extracellular matrix or a combination thereof comprise at least one of miR-145 and miR-656.

In other embodiments, the method can further be performed in combination with administration of an anti-cancer agent along with the MSCs conditioned media, ECM, or extracellular vesicles. In some embodiments, treatment of cancer by the pharmaceutical compositions of the invention can be performed in combination with surgery, radiotherapy, chemotherapy, immunotherapy, viral therapy, gene therapy or combinations thereof. In some embodiments, the methods of the invention for treating a proliferative disease further comprise irradiation of the subject. In some embodiments, the proliferative disease is a brain cancer and the methods further comprise irradiation of the brain. In some embodiments, irradiation of the brain comprises a protective effect of the pharmaceutical compositions of the invention on the healthy brain cells.

Typically, radiation is a common treatment for cancer, though it can have damaging effects on the body. As demonstrated herein, UC- and CH-MSCs and to a lesser extent DP-MSCs and their secreted extracellular exosomes were found to protect against radiation-induced injury, in the brain partly by inhibiting specific microglia phenotypes, vascular damage, demyelination and inflammatory responses in general. In addition, they can sensitize the tumors and cancer stem cells to radiation induced injury. In some embodiments, a pharmaceutical composition of the invention is administered to a subject prior to radiation therapy. In some embodiments, a pharmaceutical composition of the invention is administered to a subject together with or subsequent to radiation therapy.

The term "diabetes" refers to the metabolic disease diabetes mellitus. In some embodiments, this refers to type I diabetes, also known as insulin-dependent diabetes mellitus. In other embodiments, this refers to type II diabetes, also known as adult onset diabetes mellitus.

The term "muscle disease or neuromuscular disease" refers to any disease that effects the muscles of the subject directly or indirectly. In some embodiments, the muscle disease is any one of a muscular dystrophy, cachexia, sarcopenia, muscle injuries and muscle inflammatory disorders. Examples of muscle inflammatory disorders include but are not limited to inflammatory myopathies, genetic disorders such as muscular dystrophies and HIBM, spinal injuries, ALS, spinal muscular atrophy, diseases of peripheral nerves and of neuro-muscular junctions such as myasthenia gravis. In some embodiments, the muscular dystrophy is selected from Duchenne's muscular dystrophy (DMD), and Baker muscular dystrophy. In some embodiments, the muscular dystrophy is DMD.

In some embodiments, the disease is a muscle disease and the extracellular vesicles, conditioned media, ECM or a combination thereof comprise at least one of miR-29a, miR-29b and miR-29c. In some embodiments, the disease is a muscle disease and the extracellular vesicles, conditioned media, ECM or a combination thereof comprise at least one of miR-29a, miR-29b, miR-29c and miR-656. In some embodiments, the disease is a muscle disease and the extracellular vesicles, conditioned media, ECM or a combination thereof comprise miR-656.

The term "aging" or "age-related disorders" refers to a persistent decline in the age-specific fitness components of a subject due to internal physiological degeneration. This may include, but is not limited to: muscle aging, cardiovascular function, mental acuity, skin elasticity, metabolism, visual acuity, auditory acuity, or pulmonary function to name but a few fitness components. In some embodiments, aging comprises at least one of skin aging, muscle again, and brain aging.

The terms "neurological disorder" and "neurological disease" are interchangeable and refer to any of the diseases that occur in the nervous system. In some embodiments, the neurological disease is selected from brain cancer, cancer metastasis to the brain, Parkinson's disease, Alzheimer's disease, Rett syndrome, amyotrophic lateral sclerosis (ALS), multiple sclerosis (MS), neurological injury, hypoxia induced injury and radiation induced injury. In some embodiments, a neurological disease is selected from any one of brain cancer, cancer metastasis to the brain, Parkinson's disease, Alzheimer's disease, Rett syndrome, amyotrophic lateral sclerosis (ALS), multiple sclerosis (MS), neurological injury, radiation induced injury, hypoxia induced injury, vascular-induced dementia, autism, depression, stroke, cerebral palsy and various orphan diseases in the CNS.

The term "autoimmune disease" refers to any disease in which an immune response is targeted against a healthy cell of the subject. In some embodiments, the autoimmune disease is selected from MS, diabetes and Chron's disease. In some embodiments, the autoimmune disease is associated with abnormal inflammation. In some embodiments, the autoimmune disease is selected from MS, diabetes, Chron's disease, lupus, colitis, and rheumatoid arthritis.

The term "energy homeostasis disease" refers to any disease or condition in which the energy production in the subject is abnormal or pathological. In some embodiments, the energy homeostasis disease is diabetes.

The term "digestive disease" refers to any disease or disorder of the digestive tract. In some embodiments, the digestive disease is selected from irritable bowel syndrome (IBD), Chron's disease and colitis.

The term "allogenic transplantation" refers to the transplantation of cells (e.g., neuronal, neural stem or glial cells) into a patient, when the cells originate from another person. In some embodiments, this other person is a sibling, parent, child, or other close relative. In other embodiments, the other person is an unrelated donor. In some embodiments, the CH-MSC population is allogenic to the subject. In some embodiments, the CH-MSC population is autologous to the subject. A person skilled in the art will understand that chorionic placenta cells are lowly or non-immunogenic and thus may come from an autologous source. Further, when exosomes, conditioned media or ECM are administered they are also lowly or non-immunogenic and thus may come from an autologous source.

The present invention also provides for extracellular vesicles (such as exosomes and/or microextracellular vesicles) derived and isolated from MSCs as cellular products. The MSCs can be any type described above.

Exosomes, extracellular vesicles, or microextracellular vesicles can be obtained by growing MSCs in culture medium with serum depleted from exosomes or in serum-free media such as OptiMeM and subsequently isolating the exosomes by ultracentrifugation. Other methods associated with beads, columns, filters and antibodies are also employed. In some embodiments, the MSCs are grown in hypoxic conditions or incubated in medium with low pH so as to increase the yield of the exosomes. In other embodiments, the MSCs are exposed to radiation so as to increases exosome secretion and yield. MSCs can also grow on low-attachment plates as spheroids which can increase their neuronal characteristics. The exosomes can then be suspended in appropriate media for administration. In some embodiments, any method of treatment for which a specific MSC population may be used, exosomes from that population may also be used.

The present invention also provides for a method of delivery by using at least one of an MSC, exosomes, extracellular vesicles, or microextracellular vesicles to deliver material to an individual. The specific MSCs or their exosomes/extracellular vesicles/microextracellular vesicles can also be employed to deliver modified RNA, siRNAs, antisense, miRNAs and long non-coding RNAs, modified mRNA in addition to viruses, drugs, plasmids and purified proteins. This delivery can be done by injecting iv, intraarterially, intranasally, intramuscular, intraperitoneal, intracranialy, and locally to tumor sites or diseased and targeted tissue. In addition, the exosomes/extracellular vesicles and microextracellular vesicles can be targeted to specific sites or tissues and organs using specific peptides.

The present invention provides advantages in that by characterizing specific populations of MSCs, and by using their derived extracellular vesicles, their impact can be more specific and efficient, with less unwanted effects and can be predicted for various clinical indications. Currently, the choice of MSCs for treatment of specific diseases is not based on any educated reason. Because MSCs can be obtained from allogeneic sources, using these MSCs is helpful in patients with genetic disorders or in situations where there is an urgent need to treat patients immediately and there is no ability to generate autologous cells. UC- and CH-MSCs are not rejected due to the lack of MHCII expression. Therefore, these MSCs can be used as "off the shelf" products. Further the exosomes of these MSC populations also do not express MHCII molecules as can also be used as "off the shelf" extracellular vesicles.

The present invention also provides an advantage by inhibiting the immune response during various therapies. Modified mRNA therapy and other therapies are immunogenic and may therefore raise unwanted side effects. Since MSCs downregulate immune responses, the delivery of these therapeutics with MSCs, or their secreted exosomes (in particular UC- and CH-MSCs), can combined a targeted delivery with the cells inherent ability to abrogate immune response towards the specific treatment.

MSC transfer of mitochondria to target cells can confer a therapeutic effect in preventing injuries and protecting cells in various pathological conditions. UC- and CH-MSCs exhibit an increased level of mitochondria transfer as compared with BM-, AD- and DP-MSCs. In some embodiments, the UC- and CH-MSCs can be administered to a subject in need of mitochondrial based therapy.

Laboratory Use

By another aspect there is provide a method of maintaining stem cells and primary cells in culture, the method comprising,
(a) providing stem cells, primary cells or both;
(b) growing the stem cells, primary cells or both in culture medium comprising extracellular vesicles derived from MSCs, thereby maintaining stem cells, primary cells or both in culture.

As used herein, "primary cells" refers to any cells directly taken from an organism. In some embodiments, the primary cells are mammalian primary cells. In some embodiments, the primary cells are rodent or murine primary cells. In some embodiments, the primary cells are human primary cells. The primary cells may be from any organ or tissue, including but not limited to, blood, brain, heart, liver, lung, pancreases, colon, stomach, epidermis, testes, ovary, and muscle. In some embodiments, the primary cells are neurons. In some embodiments, the primary cells are oligodendrocytes.

As used herein, "stem cells" refer to any cells with the capability to differentiate to more than one cell type. In some embodiments, the stem cells are mammalian stem cells. In some embodiments, the stem cells are rodent or murine stem cells. In some embodiments, the stem cells are human stem cells. The stem cells may be from any organ or tissue, including but not limited to, blood, brain, heart, liver, lung, pancreases, colon, stomach, epidermis, testes, ovary, and muscle. In some embodiments, the stem cells are pluripotent, or multipotent. Each possibility represents a separate embodiment of the invention. In some embodiments, the stem cells are cancer stem cells (CSCs).

A person skilled in the art will appreciate that primary cells and stem cells do not survive for extended periods in culture. In some embodiments, the survival of a stem cell or primary cell in culture without MSCs is at most 3, passages, 5 passages, 7 passages or 9 passages. Each possibility represents a separate embodiment of the invention. In some embodiments, maintaining comprises culturing the stem cells, primary cells or both in vitro for at least 8, 10, 12, 14, 15, 16, 18, or 20 passages. Each possibility represents a separate embodiment of the invention. In some embodiments, maintaining comprises extending survival of the stem cells, primary cells or both beyond survival of the cells in culture medium substantially devoid of extracellular vesicles from the MSC. In some embodiments, the maintaining comprises the stem cells, primary cells or both retaining the ability to undergo both symmetric and asymmetric divisions.

In some embodiments, the culture medium comprises conditioned media from the MSC. In some embodiments, the culture medium comprises extracellular matrix from the MSCs. In some embodiments, the methods of the invention further comprise growing the stem cells, primary cells or both in primary cell growth media.

In some embodiments, the cells are healthy cells. In some embodiments, healthy cells are any primary or stem cells other than cancer cells. In some embodiments, the cells are healthy cells and the MSC are selected from UC-, CH-, AD-, BM-, DP-MSCS and a combination thereof. In some embodiments, the cells are healthy cells and the MSCs are selected from UC-, CH-MSC and a combination thereof. In some embodiments, the cells are healthy cells and the MSCs are CH-MSC. In some embodiments, the stem cells are cancer stem cells and the MSCs are selected from BM-, AD-, AM-MSC and a combination thereof. In some embodiments, the stem cells are cancer stem cells and the MSCs are AM-MSCs.

Subpopulations

As demonstrated herein below, the MSC subpopulations, as defined here, were shown to be amendable and/or superior to the general MSC populations for treating certain diseases or conditions. In one embodiment, UC- and CH-MSCs as described herein, may be grown in the presence of one or more of the following: 5-aza, valproic acid, TGF-β inhibitors, WNT3 proteins or agonists SHH inhibitors retinoic acid, metformin, butyric acid or prostaglandin E2, followed by maintenance in medium with horse serum or in serum free medium, so as to promote a phenotype that further supports therapeutic effect in muscle or neural diseases. In some embodiments, the WNT3 agonist is CAS 853220-52-7 (also called BML-284). As demonstrated herein, these MSC subpopulations also secrete high levels of GDNF, VEGF and IGF-1 which support motor neuron survival and therefore can also be employed for the treatment of ALS, such as when implanted intramuscularly or intrathecally.

In some embodiments, the MSCs are incubated in the presence of a target tissue before administration to the target tissue. Incubation of MSCs with a tissue, primes the MSCs and their extracellular vesicles toward that tissue and enhances the ability of the MSCs or vescicles to provide a directed regenerative effect in that target tissue.

The term "TGF-β inhibitors" as used herein, refers to any compound, therapeutic or drug that suppresses the physiologic response to transforming growth factor beta (TGFβ). This can be accomplished by targeting any step of the TGFβ signaling pathway. This suppression can be at least 60%, and least 65%, at least 70%, at least 75%, at least 80%, at least 85%, at least 90%, at least 95%, at least 99% suppression of this signaling. Many well characterized TGFβ inhibitors are known in the art.

The term "WNT3 agonists" as used herein refers to any compound, therapeutic or drug that mimics WNT3 activation activity. Examples of WNT3 agonists are available in the literature and some non-limiting examples are recombinant WNT3A proteins or the WNT3A agonist CAS 853220-52-7 (also called BML-284).

The term "SHH inhibitors" as used herein, refers to any compound, therapeutic or drug that suppresses the physiologic response to sonic hedgehog protein (SHH). This can be accomplished by targeting any step of the SHH signaling pathway. This suppression can be at least 60%, and least 65%, at least 70%, at least 75%, at least 80%, at least 85%, at least 90%, at least 95%, at least 99% suppression of this signaling. Many well characterized SHH inhibitors are known in the art.

In one embodiment, the MSC population described herein, may be grown as spheroids, such as in low attachment plates, in Opti-MEM media and 2% FBS or human serum albumin or in the presence of BDNF in serum free medium. In some embodiments, said MSCs are further grown in the presence of adrenergic receptor agonists or metformin or retinoic acid or an HDAC inhibitor, or a GSK-3 inhibitor, or TGF-β pathway inhibitor or a combination thereof and are maintained for about 1-24 hours in hypoxic condition. In some embodiments, said growth promotes a phenotype that further supports neuronal survival and regeneration. This growth condition when applied to UC-, CH-, BM-, AD- and DP-MSC promoted a phenotype that was particularly supportive of neuronal survival and regeneration. As demonstrated herein, these MSC subpopulations can be employed for the treatment of various neurological disorders.

The term "3D cell culture" as used herein refers to cell culture wherein cells are permitted to grow or interact with their surroundings in all three dimensions. In some embodiments, this can be achieved by growing the cells on low adherence plates, bioreactors, or small capsules. In some embodiments, the cells grown in 3D culture will take the shape of a spheroid as they grow. In other embodiments, the cells will take the shape of an organoid. The term "organoid" as used herein refers to a three-dimensional organ-bud grown in vitro, that shows realistic micro-anatomy similar to the organ which it is modeling.

The term "adrenergic receptor agonists" as used herein refers to any compound, therapeutic or drug that activates an adrenergic receptor. Examples of adrenergic receptor agonists are available in the literature.

The term "HDAC inhibitor" as used herein refers to any compound, therapeutic or drug that interferes with the function of histone deacetylases and suppresses their ability to deacetylate histones. This suppression can be at least 60%, and least 65%, at least 70%, at least 75%, at least 80%, at least 85%, at least 90%, at least 95%, at least 99% suppression deacetylase active. Many well characterized HDAC inhibitors are known in the art.

The term "GSK-3 inhibitor" as used herein refers to any compound, therapeutic or drug that interferes with the kinase function of Glycogen synthase kinase 3 A or Glycogen synthase kinase B and suppresses their ability to phosphorylate a target. This suppression can be at least 60%, and least 65%, at least 70%, at least 75%, at least 80%, at least 85%, at least 90%, at least 95%, at least 99% suppression deacetylase active. Many well characterized GSK-3 inhibitors are known in the art.

The term "hypoxia" or "hypoxic conditions" as used herein refers to a state in which the body, a region of the body, or cells are deprived of an adequate supply of oxygen. In some embodiments, the cells are grown in culture, in a hypoxia control chamber, wherein oxygen levels can be closely controlled. In hypoxia, oxygen levels may be below 5%, below 4.5%, below 4%, below 3.5%, below 3%, below 2.5%, below 2%, below 1.5%, below 1%, below 0.5%, below 0.1%.

In one embodiment, the MSC populations described herein, may be grown as spheroids with one or more of: hypoxia, PDGF, activin A, and low glucose, so as to promote a phenotype that further supports therapeutic effect in diabetes. As demonstrated herein, these MSC subpopulations can be employed for supporting regeneration of islet cells, and these growth conditions produced especially effective cells from populations 1, 2, 3 and 4 and their extracellular vesicles.

The term "low glucose" as used herein refers to state in which the growth media used for tissue culture has a glucose concentration at or below the standard of 1 gram/liter (5.5 mM). This is equivalent to a glucose concentration at or below that of normal blood sugar levels in vivo. In low glucose conditions the concentration of glucose may be less than 1 g/L, less than 0.9 g/L, less than 0.8 g/L, less than 0.7 g/L, less than 0.6 g/L, less than 0.5 g/L, less than 0.4 g/L, less than 0.3 g/L, less than 0.2 g/L, less than 0.1 g/L.

In one embodiment, UC-, CH-, BM- and DP-MSCs as described herein, may be grown in medium containing adrenergic receptor agonists together with exposure to hypoxia. As demonstrated herein, these MSC subpopulations and their extracellular vesicles can be employed for treatment of various cancerous states including brain tumors and neuroblastoma.

In one embodiment, all MSC populations as described herein, may be grown in medium containing metformin or phenformin in Optimem or other media without serum or with DMEM or MEM/F12 with serum alone or together with adrenergic receptor agonists and exposure to hypoxia, so as to promote a phenotype within the MSC and their extracellular vesicles that further supports therapeutic effect in various neurological disorders, radiation induced injury, diabetes, brain tumors and cerebral palsy.

In one embodiment, MSCs of all populations as described herein, may be grown in medium of pH 5.0-6.0 for a short time (1 hour) followed by growing as a spheroid with medium containing growth factors such as EGF and FGF and then treated with adrenergic receptor agonists or metformin, or phenformin, or retinoic acid or a combination thereof so as to promote a phenotype in the MSCs and their extracellular vesicles that further supports a therapeutic effect in neurological conditions. Short term treatment with low pH makes MSCs more amenable to the above treatments and thus enhances the promotion of phenotypes that further support therapeutic effect in specific disorders.

The term "low pH" as used herein, refers to a condition in which the pH of the growth media is at or below 6.0. In low pH, the growth media could have a pH of 6.0, 5.5, 5.0, 4.5, 4.0, 3.5, 3.0.

In one embodiment, UC- and CH-MSCs and their extracellular vesicles are administered to a subject prior to, simultaneous with or following hyperbaric oxygen therapy to enhance therapeutic effects and engraftment. In some embodiments, this is done with G-CSF or metformin, and in some embodiments without G-CSF or metformin. In some embodiments, hyperbaric oxygen therapy in combination with MSCs or their extracellular vesicles can be employed for the treatment of muscle disorders, brain and spinal injuries, neurological disorders, diabetes and radiation-induced injury.

The term "hyperbaric oxygen therapy" as used herein refers to 1-3, 1-2.5, 1-2, 1-1.5, 1.5-3, 1.5-2.5, 1.5-2, 2-3, 2.5-3 atmospheres of pressure, of absolute (100%) oxygen.

In one embodiment, AD- and AM-MSCs and their secreted exosomes increase EMT and stemness of tumor cells and can be employed to generate in vitro models of EMT and to maintain tumor cells and cancer stem cells in culture. Co-cultures of microglia and brain tumor cells with AD- and AM-MSCs and their secreted exosomes increased efficacy of human xenograft formation of tumors in mice and induce de-differentiation of differentiated tumor cells to cells with cancer stem cell phenotypes.

In one embodiment, any of the MSC populations are treated with low intensity laser light, pulsed focus, ultrasound, mechanical stimulation shock wave therapy prior to transplantation into the muscle or the heart so as to promote a phenotype that further supports therapeutic effect in skeletal, muscle diseases, motor and peripheral nerve diseases and cardiac disorders.

In one embodiment, UC- and CH-MSCs and their exosomes can be targeted to specific organs with low laser intensity light, pulsed focused ultrasound, and shock wave therapy. Deep brain stimulation can be employed for the targeting of MSCs and their exosomes into the brain for the treatment of Parkinson's disease and other movement disorders and psychiatric disorders.

The term "low intensity laser light" as used herein refers to treatment of tissue or cells with low-power lasers or light-emitting diodes in a range of 1-1000 mW and at wavelengths from 390-1100 nm. The treatment can be a continuous wave or pulsed. Various sources of light can be used including, but not limited to inert gas lasers and semiconductor laser diodes.

In one embodiment, the MSC populations can be maintained as 3D organoids, so as to promote a phenotype that further supports therapeutic effect in the generation of missing bone or tendon. Further growth of the cells in medium containing adrenergic receptor agonists combined with short exposure to hypoxia promotes a phenotype that further supports therapeutic effect in spinal cord injury.

In some embodiments, the MSCs of any population can be incubated with human cells before therapeutic administration. Human cells derived from tissue that is related to a disease or condition enhances the therapeutic effect of the MSCs in treating that disease or condition. For example, incubation of MSCs with human muscle cells, wherein transfer of soluble factor was possible, preconditioned the MSCs and their exosomes for a better therapeutic effect in treating muscle diseases. In some embodiments, the human cells are derived from muscle, neural, pancreatic, liver or cardiac tissues. In some embodiment, the cells are derived from any tissue in which a disease or condition is present.

For all these treatments that enhance therapeutic effect, exosomes can be extracted from the resulting MSC subpopulations that will also have the same enhanced phenotype as the MSCs themselves. Short-term irradiation of MSCs results in production of higher levels of exosomes.

The term "short term irradiation" as used herein refers to irradiation with 1-10 Gy prior to exosome extraction. Said extraction occurring 1-24 hours after irradiation.

In one embodiment, UC- and CH-MSCs and their extracellular vesicles can be used for the treatment of disc regeneration.

In one embodiment, the CH-, BM-, AD-, DP-MSCs are used in combination with UC-MSCs for the treatment of bone damage to generate bone repair and angiogenesis.

In other embodiments, the methods of this invention can further be performed in combination with incubation of the MSCs with additional compounds. In some embodiments, this incubation can be, but is not limited to incubation with: 5-aza, valproic acid, adrenergic receptor agonists, GSK-3 kinases inhibitors, TGFβ pathway inhibitors, WNT3 proteins or agonists SHH inhibitors, retinoic acid, ATRA, metformin, phenformin, butyric acid, copaxone, steroids, tamoxifen, curcumin or prostaglandin E2. As demonstrated herein, the resulting MSC subpopulations can be employed for supporting regeneration of islet cells, neurons, muscle and this growth conditions produced especially cells from UC-, CH-, BM-, AD-, DP-MSCs.

In some embodiments, the methods of this invention can further be performed in combination with G-CSF treatment. In some embodiment, the methods of this invention can be performed in combination with G-CSF treatment and one of more of the following: metformin, steroids, melatonin, curcumin, tamoxifen, copaxone, or pulsed focused ultrasound treatment. In some embodiments, this combined treatment is used to treat, in addition to other conditions, muscle disease, neuromuscular disorders, motor and peripheral muscle disorders, neurological disorders and ALS.

The term "G-CSF treatment" as used herein refers to administration of G-CSF to a subject, wherein the treatment mobilizes endogenous MSCs from the bone marrow to home to the site of injury or disease.

In one embodiment, UC- and CH-MSCs and their extracellular vesicles can be preconditioned with cells from a tissue of a disease, and then administered together with G-CSF. In some embodiments, the treatment further comprises pretreatment with hyperbaric oxygen therapy.

In one embodiment, UC- and CH-MSCs can be made to overexpress trophic factors such as IGF-1, BDNF, NGF, GDNF by viral vectors or modified mRNA. In some embodiments, these MSCs or their extracellular vesicles can be administered before, after or together with G-CSF or hyperbaric oxygen therapy, with or without metformin, for the treatment of ALS, brain and spinal cord injury, radiation-induced injury and neurological disorders.

In one embodiment, UC- and CH-MSCs can be made to overexpress membranal TRAIL or CD40L. In some embodiments these MSCs or their extracellular vesicles can be administered for the treatment of brain tumors and various other tumors.

In some embodiments, the use of MSCs for treatment of the diseases and conditions enumerated herein can be carried out in veterinary animals with or without the different treatment combinations described for human therapies. In some embodiment, human UC- and CH-MSCs and their exosomes can be used in these animals. In some embodiments, the MSC populations can be derived from veterinary animals and used to treat different types of animals without the need of using MSCs from the same breed.

Pharmaceutical Compositions

The pharmaceutical composition of the present invention is administered and dosed in accordance with good medical practice, taking into account the clinical condition of the individual patient, the site and method of administration, scheduling of administration, patient age, sex, body weight and other factors known to medical practitioners.

By another aspect there is provided, a pharmaceutical composition for use in treating a disease or condition comprising a pharmaceutically acceptable adjuvant, excipient or carrier and at least one of:
  (a) an isolated and enriched population of CH-MSCs;
  (b) extracellular vesicles derived from the CH-MSC population;
  (c) conditioned media from the CH-MSC population; and
  (d) extracellular matrix secreted by the CH-MSC population.

The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

Administration can by injection to any desired site on the body. However, other methods of administration can also be used, such as transplantation or transfusion with or without specific scaffolds. The dose can be determined by one skilled in the art, such as $0.1\times10^6$ cells/kg to $5\times10^6$ cells/kg, or 0.1-1 μg of purified exosomes. The MSCs can be harvested from any origin by methods known in the art or by methods described herein. The MSC may be maintained under specific conditions to have the expression profile of the MSC subpopulation as described herein.

It should be noted that MSCs and their exosomes can be administered as the composition and can be administered alone or as an active ingredient in combination with pharmaceutically acceptable carriers, diluents, adjuvants, and vehicles. The composition can also be administered orally, subcutaneously, or parenterally including intravenous, intraarterial, intramuscular, intraperitoneally, intratonsillar, and intranasal administration as well as intrathecal and infusion techniques. Implants of the compositions are also useful. The patient being treated is a warm-blooded animal and, in particular, mammals including man. The pharmaceutically acceptable carriers, diluents, adjuvants, and vehicles as well as implant carriers generally refer to inert, non-toxic solid or liquid fillers, diluents or encapsulating material not reacting with the active ingredients of the invention.

The doses can be single doses or multiple doses over a period of several days, weeks, months or even years. The treatment generally has a length proportional to the length of the disease process and drug effectiveness and the patient species being treated.

When administering the composition of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Non-aqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only and are not intended to be limiting unless otherwise specified. Thus, the invention should in no way be construed as being limited to the following examples, but rather, should be construed to encompass any and all variations which become evident as a result of the teaching provided herein.

As used herein, the terms "administering", "administration" and like terms refer to any method which, in sound medical practice, delivers a composition containing an active agent to a subject in such a manner as to provide a therapeutic effect. One aspect of the present subject matter provides for oral administration of a therapeutically effective amount of a composition of the present subject matter to a patient in need thereof. Other suitable routes of administration can include parenteral, subcutaneous, intravenous, intramuscular, or intraperitoneal. The dosage administered will be dependent upon the age, health, and weight of the recipient, kind of concurrent treatment, if any, frequency of treatment, and the nature of the effect desired. In some embodiments, administering comprises at least one of intravenous administration, intramuscular administration, intranasal administration, intrathecal administration, intrastriatal administration, intracranial administration, intraarterial administration, and subcutaneous administration.

As used herein, the term "carrier," "excipient," or "adjuvant" refers to any component of a pharmaceutical composition that is not the active agent. As used herein, the term "pharmaceutically acceptable carrier" refers to a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present.

Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers, and diluents useful in the present compositions include distilled water, physiological saline, Ringer's solution, dextrose solution, Hank's solution, and DMSO.

These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety.

The carrier may comprise, in total, from about 0.1% to about 99.99999% by weight of the pharmaceutical compositions presented herein.

The definitions of certain terms as used in this specification are provided herein. Unless defined otherwise, all technical and scientific terms used herein generally have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

As used in this specification and the appended claims, the singular forms "a", "an" and "the" include plural referents unless the content clearly dictates otherwise. For example, reference to "a nucleic acid" includes a combination of two or more nucleic acids, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Mesenchymal stem cell cultures: Bone marrow- and adipose-derived MSCs and were generated as described in the literature. Placenta-derived MSCs and umbilical cord-derived MSCs were generated as follows: The tissues are washed with PBS. The amniotic and the chorionic membrane are mechanically fragmented into small pieces and they are submitted to enzymatic digestion in two stages: The cell suspension is then filtered through 100 µM filter and the centrifuged cells are seeded in DMED medium/nutrient mixture F-12 (DMEM/F12) consisting of 15% fetal calf serum, 2 mM L-glutamine, 100U/ml penicillin and 100 µg/ml streptomycin. After two weeks, the plates are washed and incubated for one day with a ROCK inhibitor, followed by incubation in hypoxic conditions for 24 hr. The cells are then maintained in DMEM medium with 15% FCS depleted of exosomes. In some cases, cells are maintained in OptiMem, or in DMDEM+human serum albumin and can be supplemented with growth factors, such as FGF and EGF and with a cocktail of CHIR99021, Repsox and Parnate.

Using FACS analysis the cells were found to be positive for CD73, CD90, and CD105 but negative for the hematopoietic markers CD14, CD34, CD80, and CD45. The different cell types were also examined for their ability to differentiate to osteoblasts, chondrocytes, and adipocytes. The purity of all the MSC preparations was over 95%.

Umbilical Cord MSCs—the cord was washed in sterile PBS. A syringe with PBS was used to remove blood clots from the blood vessels. The cord was opened. A cell scratcher was used to remove the epithelial cells (10 scratches with PBS1). Blood vessels were removed. The cord and WJ were cut into small pieces (5-8 square mm). Each piece was put on the plate. The full plate was left to dry for better tissue attachment for 10 minutes. Medium (MEM alpha+15% FBS, 1% OS, L-glu, Na Pyruvate, NEAA) was added and was not changed or touched for 7 days.

RNA Purification:

For RNA purification, experiments were terminated by removal of the medium and addition of lysis solution (250-500µl). Afterward, RNA was purified according to manufacturer's instructions (Total RNA miniprep kit, SIGMA). Purified RNA concentration was determined using NanoDrop spectrophotometer (Thermo Scientific, Lafayette, CO). The ratio 260:280 nm was used to assess the purity of RNA.

Real Time PCR:

For internal control, S12 mRNA levels were employed. Data were analyzed using ABI Prism 7000 software. The quantification of mRNA levels has been done using the Delta-Delta Ct (ΔΔCT) method and results are expressed in arbitrary units.

Neurosphere Formation Assay:

The ability of GSCs to self-renew was tested after incubation with the MSC-CMs. Spheroids were collected, disaggregated and then were plated in 24-well plates at a density of 100 cells/well through limiting dilution. The number of neurospheres/well was determined 14 days thereafter for 8 different wells.

Preparation of Exosome by Ultracentrifugation:

Supernatant fractions collected from cell cultures were pelleted by centrifugation at 2000 g for 10 minutes. The supernatant was centrifuged at 20,000 g for 20 minutes. Exosomes were then isolated by centrifugation at 100,000 g for 70 minutes at 4° C. The exosome pellet was washed in 12 ml of PBS and was ready for use after additional ultracentrifugation. In some instances, the exosomes were isolated by density gradient ultracentrifugation (100,000-200,00 g). Size-based isolation techniques, such as ultrafiltration, were also employed.

Microarray Analyses

Mirna Array:

The experiments were performed using Affymetrix HU GENE1.0st oligonucleotide arrays. Sample processing was performed according to the Affymetrix WT protocol.

Xenografts Studies:

Dissociated GSCs transduced with a lentivirus vector expressing fLUC were inoculated intracranially into nude mice (Nu/Nu). Mice were transplanted with MScs (1×106 cells) 2 weeks following GSC implantation. All animals were monitored daily and sacrificed at the first signs of neurological deficit. Tumor growth in mice was monitored using Xenogen imaging system.

Bioluminescence Imaging:

For in vivo luciferase assays, D-luciferin (150 mg/kg) was inoculated i.p. into nude mice to measure the tumor size. Bioluminescence images were obtained using the IVIS Spectrum System (Perkin-Elmer Life Sciences, Waltham, MA).

Statistical Analysis:

The results are presented as the mean value±SE. Data were analyzed using analysis of variance and a Student's t test.

Example 1

Profiling MSCs Derived from Different Tissues

MSCs from different sources have been demonstrated to have differential cellular effects and therapeutic impacts in various clinical models. In addition, MSCs from each source represent a mixture of various subpopulations. In order to characterize different sources and subpopulations with specific characteristics and implications for more specific and efficient clinical applications, various parameters of these cells were compared and analyzed.

MSC from eight different tissues were examined: bone marrow (BM), chorionic placenta, (CH), amniotic placenta (AM), adipose (AD), umbilical cord (UC), Dental Pulp (DP), Exfoliated deciduous teeth (DD), Dental Follicular (DF).

Major differences were found between the MSCs that were derived from the different sources and also that each tissue could contain different subpopulations that are characterized by different profiles of markers. For example, with regards to the effects of specific MSCs on promoting or inhibiting tumor growth, it was surprisingly found that different miRNAs and lncRNAs were expressed and secreted by the different MSCs.

In addition to cytokines and growth factors, MSCs also secrete exosomes. These extracellular vesicles themselves contain miRNAs, and non-coding RNAs. They can also contain soluble proteins, and additionally have been found to have protein surface markers within their outer membrane.

Example 2

MSCs have a Common Expression Profile

MSCs and their exosomes were further analyzed to obtain unique expression profiles.

Flow cytometry and fluorescence-activated cell sorting (FACS) enables the prospective enrichment of MSCs and can be utilized to study intact cells as well as specific cell surface antigens. To identify cell surface proteins expressed on the surface of MSCs (i.e. surface markers), a high throughput flow cytometry screen was performed, which allowed the identification of cell surface antigens differentially expressed in five different types of MSCs (UC, CH, BM, AD and DP). Each population of MSCs was analyzed for 324 surface markers.

Of the 324 investigated surface markers 51 were detected on all MSCs. They were the following: CD9, CD10, CD13, CD26, CD29, CD44, CD36, CD46, CD47, CD49a, CD49b, CD49c, CD49d, CD49e, CD50, CD51/61, CD54, CD55, CD58, CD59, CD61, CD63, CD71, CD73, CD81, CD83, CD87, CD90, CD91, CD95, CD97, CD98, CD99, CD105, CD108, CD109, CD140b, CD142, CD146, CD147, CD151, CD164, CD165, CD166, CD273, β2-microglobulin, HLA-A,B,C, HLA-A2 STRO1.

All MSCs were negative for CD34, CD45, CD11b, CD14, CD49a or CD19 and HLA class II. Exosomes secreted from these cells are expected to be similarly positive or negative for the markers described above.

To further explore MSC subtype differences, gene expression arrays were also performed using Illumina chip. The expression of approximately 35,000 genes from MSCs produced from these 5 tissues were analyzed. A comparative study was done of growth factors secreted by MSCs from different sources, and factors were identified that are expressed from different MSCs at different levels. MSCs exert some of their effects by paracrine effects via the secretion of various growth factors. The secretion of different factors by the different types of MSCs was analyzed using 2 approaches. In the first, the secreted proteins were extracted using gene array analysis. In the second approach, protein secretion was measured using antibody array on MSC supernatants. Supernatants were collected from the MSC cultures and they were analyzed for 50 growth factors and cytokines using specific antibodies.

The vast majority of non-noncoding RNAs, secreted proteins and surface proteins were differentially expressed in the various MSCs and their exosomes. The results of these experiments are summarized in Tables 1-8. These populations of MSC can be distinguished from each other by unique lncRNA, miRNA and surface protein expression and by uniquely secreted proteins. Indeed, at least one unique surface protein was found on each of UC-, CH-, BM-, AD- and AM-derived MSCS, allowing for direct identification and isolation by, FACS, column chromatography, magnetic bead sorting, or any other method of immuno-identification.

Example 3

Each MSC and Exosome Subtype has a Unique Expression Profile

UC-MSCs were characterized by the unique expression profile found in Table 1.

TABLE 1

UC-MSCs uniquely expressed, and enriched RNAs, proteins, and exosomal factor

| | |
|---|---|
| lncRNAs | DGCR5, GAS5, H19, HAR1A, HOXA3AS, HOXA6AS, KRASP1, MER11C, PCAT-32, STOT3, TU-00176 |
| miRNAs | See Table 10 |
| genes | See Table 11 |
| surface proteins | CD184, CD193, CD235a, CD318, CD255, CD268, fMLP, ITGA2, ITGA4, CD326 |
| secreted factors | VEGF, ANG, PDFRAA, BDNF, NT-4, FGF4, TIMP1, IL-8, HAPLN1, DMP1, Stanniocalcin1, ADAM23, SCG5 |
| exosomes: | |
| lncRNAs | Y4, PTENP1, NEAT1 |
| proteins | ATP1B3, ATPB1, ATPB3, CD47, CD55, BSG, CSPG4, EPHA2, GPC1, GPRC5A, MME, MMP14, MPZL1, NCSTN, PLAUR, PVR, SLC16A1, SLC1A3, SLC1A4, SLC1A5, SLC2A3, SLC39A14, SLC7A1 |

CH-MSCs were characterized by the unique expression profile found in Table 2.

TABLE 2

CH-MSC uniquely expressed, and enriched RNAs, proteins, and exosomal factors

| | |
|---|---|
| lncRNAs | SCA8, TU00176, LINCVLDLR, ROR |
| miRNAs | See Table 10 |
| genes | See Table 11 |
| surface proteins | TCR alpha-beta, CD55, LIFR, ST6GALNACS, MIC A/B |
| secreted factors | HGF, WNT2, GDNF, Osteoprotegerin, MIP3α, NT-3, LIF, IL-6, IL-8, BDNF, FGF7, NT-4, EGFL6 |
| exosomes: | |
| lncRNAs | BCMS, BIC, HAR1B |
| proteins | COL4A2, LGALS3, SCUBE1, LGAS3, S100A10 |

BM-MSCs were characterized by the unique expression profile found in Table 3.

TABLE 3

BM-MSCs uniquely expressed, and enriched RNAs, proteins, and exosomal factors

| | |
|---|---|
| lncRNAs | aHIF, ANRIL, HOTAIR, HOXA3AS, LIT, PANDA, SAF |
| miRNAs | See Table 10 |
| genes | See Table 11 |
| surface proteins | CD24, CD48, CD66b, CD338, CD120b, CD268, FGFLR1, ITGA5, NES, PDGFRAA |
| secreted factors | IGFBP2, TGFβ, IL-4, ALPL, TSLC1, PGF, COL5A3, DSG2, PENK precursor |
| exosomes: | |
| lncRNAs | BC017743, BIC, TUG, NEAT1 |
| proteins | CACNA2D1, CLTC, CORO1C, DMBT1, IGHA1, IGHA2 |

AD-MSCs were characterized by the unique expression profile found in Table 4.

TABLE 4

AD-MSCs uniquely expressed, and enriched RNAs, proteins, and exosomal factors

| | |
|---|---|
| lncRNAs | PCAT-29 |
| miRNAs | See Table 10 |
| genes | See Table 11 |
| surface proteins | CD84, PDGFRBB, TNFRSF11B |
| secreted factors | TGFβ, IL-4, CCL2, CFRP1, COMP, CTSK, MFAP5, MMP1, CXCL6, IGFBP6 |

TABLE 4-continued

AD-MSCs uniquely expressed, and enriched RNAs, proteins, and exosomal factors

| | |
|---|---|
| exosomes: | |
| lncRNAs | AAA1, GOMAFU, HOTAIR |
| proteins | SOD3, TGM3, IGF2R, FGFR1, ADAMTS13 |

AM-MSCs were characterized by the unique expression profile found in Table 5.

TABLE 5

AM-MSCs uniquely expressed, and enriched RNAs, proteins, and exosomal factors

| | |
|---|---|
| lncRNAs | GOMAFU, H19-AS, NDM29, 7SK, 21A, BIC, CMPDHOAIR, H19-AS |
| miRNAs | See Table 10 |
| genes | See Table 11 |
| surface proteins | CD 157 |
| secreted factors | RANTES, GDNF, LIF, VTN, MFAP5, FMOD, IL-4, PRSS35, NPTX2, CPA4, GLS, Neuromedin |
| exosomes: | |
| lncRNAs | aHIF, BACE1AS, CMPD, DISC2, HOTTIP, HULC, KRASP1, MALAT1, MEG3, PCGEM1, SCA8, TUG |

DP-MSCs were characterized by the unique expression profile found in Table 6.

TABLE 6

DP-MSCs uniquely expressed, and enriched RNAs, proteins, and exosomal factors

| | |
|---|---|
| lncRNAs | PCAT-1, IPW, MALAT-1, ST7OT1, LIT |
| secreted factors | BDNF, GDNF |
| exosomes: | |
| lncRNAs | EGO, H19-AS, LOC285149 LOC285194, LincRNA-VLDLR, LincRNA-SFMBT2, PSF-inhibiting RNA, ROR, ST70T3, UCA1, Y5, HAR1B |

DD-MSCs were characterized by the unique expression profile found in Table 7.

TABLE 7

DD-MSCs uniquely expressed, and enriched RNAs, proteins, and exosomal factors

| | |
|---|---|
| lncRNAs | BCO17743, BCO4343C, HOTAIRM, Y3, Y5ST7OT4, GAS5, ROR, PCAT-32 |
| secreted factors | NGF, IGF-1, GDNF, BDNF |
| exosomes: | |
| lncRNAs | BC200, BACE1AS |

DF-MSCs were characterized by the unique expression profile found in Table 8.

TABLE 8

DF-MSCs uniquely expressed, and enriched RNAs, proteins, and exosomal factors

| | |
|---|---|
| lncRNAs | DLG2AS, HULC, IGF2AS, UCA1, WT-1AS, 21A, HOXA3AS, MER11C |
| secreted factors | NGF |
| exosomes: | |
| lncRNAs | LUST, PCAT-1, PCAT-29, Y3, Tu_0017629, PTENP1 |

Example 4

Characteristics Shared by Some but not all MSC Populations

In addition to the specific factors found in each population and the universal factors found to be shared by all MSC populations, expression of factors that are shared by some, but not all, of the MSC populations was characterized.

CH- and BM-MSCs were found to share CD53 surface expression. UC- and AD-MSCs were found to share CD6 surface expression. CH- and AD-MSCs were found to share CD40 surface expression. AD- and AM-MSCs were found to share CD50 surface expression. The surface markers that were shared by more than two MSC populations can be found in Table 6.

TABLE 9

Summary of marker expression shared by MSC populations

| UC, CH, BM and AD | UC, CH and BM | CH, BM and AD | UC, CH and AD | UC, BM and AD | UC, AD and AM |
|---|---|---|---|---|---|
| CD141 (Thrombo-modulin) | CD99R | CD57 | CD153 | CD75 | CD144 |
| CD201 (EPCR) | CD112 (PRR2) | CD24 (Heat Stable Antigen) | | | |
| CD138 (Syndecan-1) | CD120a | CD77 | | | |
| MIC A/B | CD121a | | | | |
| CD56 (N-CAM) | CD130 (gp130) | | | | |
| CD107a (LAMP-1) | CD152 (CTLA-4) | | | | |
| CD140a (PDGF receptor a chain) | CD196 (CCR6) | | | | |
| CD227 (MUC1) | CD274 (B7-H1, PD-L1) | | | | |
| EGF Receptor | SSEA-4 | | | | |
| HLA-DQ | CD49f (Integrin $\alpha_6$ chain, VLA-6) | | | | |
| | CD106 | | | | |
| | CD119 | | | | |
| | CD181 | | | | |
| | CD183 | | | | |

The enriched miRNA found in the five populations can be found in Table 10.

TABLE 10

Summary of enriched miRNAs in the MSC populations

| | Enriched miRNAs |
|---|---|
| UC-MSCs | hsa-mir-127-5p, hsa-mir-4725-5p, hsa-mir-504, hsa-mir-25, hsa-mir-32, hsa-mir-363, hsa-mir-367, hsa-mir-92a, hsa-mir-92b, hsa-mir-3684, hsa-mir-4700-3p, hsa-mir-1294, hsa-mir-24, hsa-mir-548a-5p, hsa-mir-548ab, hsa-mir-548ak, hsa-mir-548b-5p, hsa-mir-548c-5p, hsa-mir-548d-5p, hsa-mir-548h, hsa-mir-548i, hsa-mir-548j, hsa-mir-548w, hsa-mir-548y, hsa-mir-559, hsa-mir-3194-5p, hsa-mir-4536, hsa-mir-875-5p, hsa-mir-3924, hsa-mir-548v, hsa-mir-101, hsa-mir-3942-5p, hsa-mir-4703-5p, hsa-mir-4694-5p, hsa-mir-4777-3p, hsa-mir-149, hsa-mir-3609, hsa-mir-548ah, hsa-mir-2277-5p, hsa-mir-3676, hsa-mir-4327, hsa-mir-4795-3p, has, mir-618, hsa-mir-3156-5p, hsa-mir-4731-3p, hsa-mir-4801, hsa-mir-4316, hsa-mir-589, hsa-mir-146a, hsa-mir-146b-5p, hsa-mir-1206, hsa-mir-515-3p, hsa-mir-519e, hsa-mir-1178, hsa-mir-4804-3p, hsa-mir-4796-3p, hsa-mir-4477a, hsa-mir-1279, hsa-mir-2116, hsa-mir-409-3p, hsa-mir-448, hsa-mir-3688-5p, hsa-mir-106a, hsa-mir-106b, hsa-mir-17, hsa-mir-20a, hsa-mir-20b, hsa-mir-519d, hsa-mir-93, hsa-mir-4729, hsa-mir-4456, hsa-mir-1237, hsa-mir-605, hsa-mir-198, hsa-mir-338-3p, hsa-mir-513a-3p, hsa-mir-142-5p, hsa-mir-600, hsa-mir-1208, hsa-mir-202, hsa-mir-2054, hsa-mir-3182, hsa-mir-380, hsa-mir-34b, hsa-mir-802, hsa-mir-4640-3p, hsa-mir-4528, hsa-mir-145, hsa-mir-656, hsa-mir-29a, hsa-mir-29b, hsa-mir-29c |
| CH-MSCs | hsa-mir-3163, hsa-mir-128, hsa-mir-27a, hsa-mir-27b, hsa-mir-148a, hsa-mir-148b, hsa-mir-152, hsa-mir-651, hsa-mir-9, hsa-mir-466, hsa-mir-577, hsa-mir-380, hsa-mir-2909, hsa-mir-4803, hsa-mir-556-3p, hsa-mir-182, hsa-mir-4677-5p, hsa-mir-4672, hsa-mir-3942-5p, hsa-mir-4703-5p, hsa-mir-4765, hsa-mir-4291, hsa-mir-144, hsa-mir-1206, hsa-mir-4435, hsa-mir-452, hsa-mir-4676-3p, hsa-mir-25, hsa-mir-32, hsa-mir-363, hsa-mir-367, hsa-mir-92a, hsa-mir-92b, hsa-mir-340, hsa-mir-3620, hsa-mir-4324, hsa-mir-4789-5p, hsa-mir-346, hsa-mir-944, hsa-mir-3180-5p, hsa-mir-202, hsa-mir-511, hsa-mir-4326, hsa-mir-578, hsa-mir-4312, hsa-mir-4282, hsa-mir-597, hsa-mir-3689d, hsa-mir-2116, hsa-mir-4517, hsa-mir-199a-3p, hsa-mir-199b-3p, hsa-mir-3129-5p, hsa-mir-520d-5p, hsa-mir-524-5p, hsa-mir-203, hsa-mir-3942-3p, hsa-mir-501-5p, hsa-mir-143, hsa-mir-4770, hsa-mir-4422, hsa-mir-4495, hsa-mir-1271, hsa-mir-96, hsa-mir-1297, hsa-mir-26a, hsa-mir-26b, hsa-mir-4465, hsa-mir-4273, hsa-mir-1294, hsa-let-7a, hsa-let-7b, hsa-let-7c, hsa-let-7d, hsa-let-7e, hsa-let-7f, hsa-let-7g, hsa-let-7i, hsa-mir-4458, hsa-mir-4500, hsa-mir-98, hsa-mir-4652-3p, hsa-mir-4716-5p, hsa-mir-513a-5p, hsa-mir-223, hsa-mir-4288, hsa-mir-455-5p, hsa-mir-632, hsa-mir-4477b, hsa-mir-142-3p, hsa-mir-561, hsa-mir-4698, hsa-mir-3140-3p, hsa-mir-3662, hsa-mir-410, hsa-mir-376a, hsa-mir-376b, hsa-mir-1270, |

TABLE 10-continued

Summary of enriched miRNAs in the MSC populations

Enriched miRNAs

|  |  |
|---|---|
|  | hsa-mir-620, hsa-mir-515-5p, hsa-mir-875-5p, hsa-mir-140-5p, hsa-mir-4256, hsa-mir-30a, hsa-mir-30b, hsa-mir-30c, hsa-mir-30d, hsa-mir-30e, hsa-mir-4254, hsa-mir-515-3p, hsa-mir-519e, hsa-mir-2964a-5p, hsa-mir-2115, hsa-mir-520a-5p, hsa-mir-525-5p, hsa-mir-1244, hsa-mir-3190, hsa-mir-548a-5p, hsa-mir-548ab, hsa-mir-548ak, hsa-mir-548b-5p, hsa-mir-548c-5p, hsa-mir-548d-5p, hsa-mir-548h, hsa-mir-548i, hsa-mir-548j, hsa-mir-548w, hsa-mir-548y, hsa-mir-559, hsa-mir-2681, hsa-mir-3671, hsa-mir-375, hsa-mir-4789-3p, hsa-mir-3143, hsa-mir-125a-5p, hsa-mir-125b, hsa-mir-4319, hsa-mir-5096, hsa-mir-338-5p, hsa-mir-493, hsa-mir-3153, hsa-mir-875-3p, hsa-mir-516a-3p, hsa-mir-323-3p, hsa-mir-3065-5p, hsa-mir-4762-3p, hsa-mir-3617, hsa-mir-641, hsa-mir-124, hsa-mir-506, hsa-mir-4531, hsa-mir-4512, hsa-mir-570, hsa-mir-4679, hsa-mir-3144-3p, hsa-mir-4777-3p, hsa-mir-4732-3p, hsa-mir-3177-5p, hsa-mir-548n, hsa-mir-4328, hsa-mir-2355-3p, hsa-mir-4330, hsa-mir-4524, hsa-mir-4719, hsa-mir-3976, hsa-mir-544, hsa-mir-3607-3p, hsa-mir-581, hsa-mir-205, hsa-mir-4731-3p, hsa-mir-4801, hsa-mir-3667-5p, hsa-mir-1245b-3p, hsa-mir-4760-3p, hsa-mir-137, hsa-mir-3194-3p, hsa-mir-342-3p, hsa-mir-2682, hsa-mir-449c, hsa-mir-532-3p, hsa-mir-4305, hsa-mir-1, hsa-mir-206, hsa-mir-613, hsa-mir-676, hsa-mir-1296, hsa-mir-196a, hsa-mir-196b, hsa-mir-3941, hsa-mir-4795-3p, hsa-mir-431, hsa-mir-607, hsa-mir-548k, hsa-mir-4464, hsa-mir-4748, hsa-mir-654-3p, hsa-mir-544b, hsa-mir-3074-5p, hsa-mir-3115, hsa-mir-4635, hsa-mir-4323, hsa-mir-548t, hsa-mir-4680-5p, hsa-mir-133a, hsa-mir-133b, hsa-mir-600, hsa-mir-1208, hsa-mir-4708-5p, hsa-mir-3123, hsa-mir-4251, hsa-mir-4307, hsa-mir-3185, hsa-mir-582-5p, hsa-mir-4436b-3p, hsa-mir-378, has, mir-378b, hsa-mir-378c, hsa-mir-378d, hsa-mir-378e, hsa-mir-378f, hsa-mir-378h, hsa-mir-378i, hsa-mir-422a, hsa-mir-4460, hsa-mir-200b, hsa-mir-200c, hsa-mir-429, hsa-mir-4470, hsa-mir-1245b-5p, hsa-mir-3142, hsa-mir-576-3p, hsa-mir-548m, hsa-mir-4666-3p, hsa-mir-325, hsa-mir-330-3p, hsa-mir-3690, hsa-mir-548a-3p, hsa-mir-548e, hsa-mir-548f, hsa-mir-4709-5p, hsa-mir-532-5p, hsa-mir-539, hsa-mir-4303, hsa-mir-4302, hsa-mir-300, hsa-mir-381, hsa-mir-4645-3p, hsa-mir-3910, hsa-mir-1301, hsa-mir-5047, hsa-mir-188-5p, hsa-mir-3974, hsa-mir-3923, hsa-mir-3686, hsa-mir-670, hsa-mir-2052, hsa-mir-548al, hsa-mir-3200-3p, hsa-mir-4686, has, mir-3545-5p, hsa-mir-194, hsa-mir-498, hsa-mir-3913-3p, hsa-mir-3168, hsa-mir-499-3p, hsa-mir-499a-3p, hsa-mir-656, hsa-mir-4762-5p, hsa-mir-4496, hsa-mir-141, hsa-mir-200a, hsa-mir-3529, hsa-mir-379, hsa-mir-3691-3p, hsa-mir-520f, hsa-mir-503, hsa-mir-4477a, hsa-mir-513a-3p, hsa-mir-3149, hsa-mir-3927, hsa-mir-1283, hsa-mir-4767, hsa-mir-487b, hsa-mir-4637, hsa-mir-19a, hsa-mir-19b, hsa-mir-4683, hsa-mir-548an, hsa-mir-1200, hsa-mir-4638-3p, hsa-mir-1825, hsa-mir-522, miR-24, miR-22-3p, miR-92, miR-378, miR-93, hsa-mir-145, hsa-mir-656, hsa-mir-29a, hsa-mir-29b, hsa-mir-29c |
| BM-MSCs | hsa-mir-1200, hsa-mir-4267, hsa-mir-3121-3p, hsa-mir-4324, hsa-mir-298, hsa-mir-4708-5p, hsa-mir-4753-5p, hsa-mir-802, hsa-mir-4446-5p, hsa-mir-4486, hsa-mir-544b, has, mir-125a-5p, hsa-mir-125b, hsa-mir-4319, hsa-mir-4755-5p, hsa-mir-326, hsa-mir-330-5p, hsa-mir-9, hsa-mir-767-5p, hsa-mir-151-3p, hsa-mir-4697-3p, hsa-mir-1343, hsa-mir-141, hsa-mir-200a, hsa-mir-621, hsa-mir-4640-5p, hsa-mir-4726-5p, hsa-mir-4272, hsa-mir-4311, hsa-mir-661, hsa-mir-4797-5p, hsa-mir-3663-3p, hsa-mir-1183, hsa-mir-1273f, hsa-mir-3926, hsa-mir-577, hsa-mir-4778-3p, hsa-mir-3922-5p, hsa-mir-139-5p, hsa-mir-1285, hsa-mir-3187-5p, hsa-mir-612, hsa-mir-4487, hsa-mir-922, hsa-mir-4660, hsa-mir-548n, hsa-mir-4531, hsa-mir-590-3p, hsa-mir-4731-5p, hsa-mir-629, hsa-mir-143, hsa-mir-4770, hsa-mir-33a, hsa-mir-33b, hsa-mir-148a, hsa-mir-148b, hsa-mir-152, hsa-mir-659, hsa-mir-3064-5p, hsa-mir-200b, hsa-mir-200c, hsa-mir-429, hsa-mir-1273e, hsa-mir-3160-3p, hsa-mir-4680-3p, hsa-mir-1266, hsa-mir-4518, hsa-mir-628-5p, hsa-mir-4330, hsa-mir-558, hsa-mir-137, hsa-mir-545, hsa-mir-501-5p, hsa-mir-4477a, hsa-mir-1182, hsa-mir-940, hsa-mir-1202, hsa-mir-3972, hsa-mir-4299, hsa-mir-891b, hsa-mir-198, hsa-mir-4329, hsa-mir-27a, hsa-mir-27b, hsa-mir-4419a, hsa-mir-4510, hsa-mir-593, hsa-mir-514, hsa-mir-514b-3p, hsa-mir-486-3p, hsa-mir-4423-5p, hsa-mir-491-3p, hsa-mir-4291, hsa-mir-936, hsa-mir-25, hsa-mir-32, hsa-mir-363, hsa-mir-367, hsa-mir-92a, hsa-mir-92b, hsa-mir-495, hsa-mir-520g, hsa-mir-520h, hsa-mir-378g, hsa-mir-218, hsa-mir-499-5p, hsa-mir-124, hsa-mir-506, hsa-mir-3141, hsa-mir-3121-5p, hsa-mir-4795-3p, hsa-mir-4528, hsa-mir-34a, hsa-mir-34c-5p, hsa-mir-449a, hsa-mir-449b, hsa-mir-4315, hsa-mir-1245, hsa-mir-4317, hsa-mir-4744, hsa-mir-627, hsa-mir-582-5p, hsa-mir-581, hsa-mir-607, hsa-mir-204, hsa-mir-211, hsa-mir-3153, hsa-mir-4786-3p, hsa-mir-3671, hsa-mir-466, hsa-mir-3657, hsa-mir-3921, hsa-mir-4653-5p, hsa-mir-140-3p, hsa-mir-3689a-5p, hsa-mir-3689b, hsa-mir-3689e, hsa-mir-3689f, hsa-mir-3163, hsa-mir-3065-5p, hsa-mir-598, hsa-mir-3158-3p, hsa-mir-219-2-3p, hsa-mir-4666-3p, hsa-mir-4434, hsa-mir-4516, hsa-mir-1246, hsa-mir-1205, hsa-mir-4649-3p, hsa-mir-3136-3p, hsa-mir-153, hsa-mir-942, hsa-mir-3646, hsa-mir-4742-5p, hsa-mir-4432, hsa-mir-618, hsa-mir-4492, hsa-mir-4498, hsa-mir-762, hsa-mir-576-3p, hsa-mir-4477b, hsa-mir-4521, hsa-mir-202, hsa-mir-885-3p, hsa-mir-3156-5p, hsa-mir-432, hsa-mir-4724-3p, hsa-mir-328, hsa-mir-4307, hsa-mir-4761-5p, hsa-mir-4684-5p, hsa-mir-760, hsa-mir-199a-5p, hsa-mir-199b-5p, hsa-mir-1270, hsa-mir-620, hsa-mir-146a, hsa-mir-146b-5p, hsa-mir-4684-3p, hsa-mir-657, hsa-mir-22 |

TABLE 10-continued

Summary of enriched miRNAs in the MSC populations

Enriched miRNAs

| | |
|---|---|
| AD-MSCs | hsa-mir-3650, hsa-mir-34a, hsa-mir-34c-5p, hsa-mir-449a, hsa-mir-449b, hsa-mir-4803, hsa-mir-4305, hsa-mir-517b, hsa-mir-4446-5p, hsa-mir-514, hsa-mir-514b-3p, hsa-mir-3646, hsa-mir-3692, hsa-mir-3677-3p, hsa-mir-4440, hsa-mir-4485, hsa-mir-3673, hsa-mir-3143, hsa-mir-431, hsa-mir-1207-3p, hsa-mir-1343, hsa-mir-3135b, hsa-mir-518d-5p, hsa-mir-519b-5p, hsa-mir-519c-5p, hsa-mir-520c-5p, hsa-mir-526a, hsa-mir-936, hsa-mir-580, hsa-mir-4255, hsa-mir-579, hsa-mir-3925-3p, hsa-mir-3924, hsa-mir-4677-5p, hsa-mir-3164, hsa-mir-4789-5p, hsa-mir-3678-3p, hsa-mir-4776-3p |
| AM-MSCs | hsa-mir-330-3p, hsa-mir-4311, hsa-mir-4652-5p, hsa-mir-340, hsa-let-7a, hsa-let-7b, hsa-let-7c, hsa-let-7d, hsa-let-7e, hsa-let-7f, hsa-let-7g, hsa-let-7i, hsa-mir-4458, hsa-mir-4500, hsa-mir-98, hsa-mir-513b, hsa-mir-186, hsa-mir-4419a, hsa-mir-4510, hsa-mir-3121-3p, hsa-mir-182, hsa-mir-548an, hsa-mir-4771, hsa-mir-141, hsa-mir-200a, hsa-mir-451b, hsa-mir-1271, hsa-mir-96, hsa-mir-4755-5p, hsa-mir-125a-5p, hsa-mir-125b, hsa-mir-4319, hsa-mir-3173-3p, hsa-mir-203, hsa-mir-1248, hsa-mir-4772-5p, hsa-mir-4503, hsa-mir-3133, hsa-mir-154, hsa-mir-3065-5p, hsa-mir-4473, hsa-mir-515-5p, hsa-mir-4795-3p, hsa-mir-1260, hsa-mir-1260b, hsa-mir-3973, hsa-mir-1470, hsa-mir-4736, hsa-mir-507, hsa-mir-557, hsa-mir-142-5p, hsa-mir-3185, hsa-mir-4286, hsa-mir-3191, hsa-mir-1, hsa-mir-206, hsa-mir-613, hsa-mir-3926, hsa-mir-2355-5p, hsa-mir-383, hsa-mir-4667-3p, hsa-mir-4666-3p, hsa-mir-4524, hsa-mir-570, hsa-mir-4712-5p, hsa-mir-770-5p, hsa-mir-4446-5p, hsa-mir-139-5p, hsa-mir-607, hsa-mir-4457, hsa-mir-518a-5p. hsa-mir-527, hsa-mir-4749-3p, hsa-mir-503, hsa-mir-578, hsa-mir-4795-5p, hsa-mir-3921, hsa-mir-4653-5p, hsa-mir-4422, hsa-mir-3140-3p, hsa-mir-4316, hsa-mir-1908, hsa-mir-663, hsa-mir-548v, hsa-mir-146a, hsa-mir-146b-5p, hsa-mir-4796-3p, hsa-mir-382, hsa-mir-653, hsa-mir-181a, hsa-mir-181b, hsa-mir-181c, hsa-mir-181d, hsa-mir-4262, hsa-mir-33a, hsa-mir-33b, hsa-mir-3190, hsa-mir-4735-5p, hsa-mir-582-5p, hsa-mir-204, hsa-mir-211, hsa-mir-4520b-3p, hsa-mir-3119, hsa-mir-149, hsa-mir-15a, hsa-mir-15b, hsa-mir-16, hsa-mir-195, hsa-mir-424, hsa-mir-497, hsa-mir-1249, hsa-mir-642b, hsa-mir-767-5p, hsa-mir-3938, hsa-mir-3591-5p, hsa-mir-4252, hsa-mir-4668-3p, hsa-mir-3529, hsa-mir-379, hsa-mir-4479, hsa-mir-4781-5p, hsa-mir-18a, hsa-mir-18b, hsa-mir-4735-3p, hsa-mir-2116, hsa-mir-200b, hsa-mir-200c, hsa-mir-429, hsa-mir-501-5p, hsa-mir-409-3p, hsa-mir-342-3p, hsa-mir-4425, hsa-mir-4540, hsa-mir-624, hsa-mir-202, hsa-mir-548ae, hsa-mir-548aj, hsa-mir-548am, hsa-mir-548x, hsa-mir-718, hsa-mir-1237, hsa-mir-1294, hsa-mir-323-3p, hsa-mir-4329, has, mir-4428, hsa-mir-4530, hsa-mir-3141, hsa-mir-4787-3p, hsa-mir-4261, hsa-mir-508-3p, hsa-mir-138, hsa-mir-4732-3p, hsa-mir-4515, hsa-mir-1972, hsa-mir-634, hsa-mir-3135b, hsa-mir-4417, hsa-mir-646, hsa-mir-1179, hsa-mir-548s, hsa-mir-329, hsa-mir-362-3p, hsa-mir-4445, hsa-mir-577, hsa-mir-3143, hsa-mir-600, hsa-mir-3925-3p, hsa-mir-3166, hsa-mir-4451, hsa-mir-3176, hsa-mir-3922-3p, hsa-mir-4436a, hsa-mir-4761-3p, hsa-mir-4667-5p, hsa-mir-4700-5p, hsa-mir-4802-5p, hsa-mir-19a, hsa-mir-19b, hsa-mir-1183, hsa-mir-2054, hsa-mir-767-3p, hsa-mir-658, hsa-mir-3609, hsa-mir-548ah, hsa-mir-217, hsa-mir-144, hsa-mir-140-5p, hsa-mir-4699-3p, hsa-mir-1468, hsa-mir-300, hsa-mir-381, hsa-mir-27a, hsa-mir-27b, hsa-mir-3978, hsa-mir-513a-5p, hsa-mir-1301, hsa-mir-5047, hsa-mir-3658, hsa-mir-106a, hsa-mir-106b, hsa-mir-17, hsa-mir-20a, hsa-mir-20b, hsa-mir-519d, hsa-mir-93, hsa-mir-3163, hsa-mir-4533, hsa-mir-4738-3p, hsa-mir-4324, hsa-mir-4744, hsa-mir-4706, hsa-mir-4749-5p, hsa-mir-4487, hsa-mir-5096, hsa-mir-3689a-5p, hsa-mir-3689b, hsa-mir-3689e, hsa-mir-3689f, hsa-mir-133a, hsa-mir-133b, hsa-mir-3158-3p, hsa-mir-3673, hsa-mir-4251, hsa-mir-548a-5p, hsa-mir-548ab, hsa-mir-548ak, hsa-mir-548b-5p, hsa-mir-548c-5p, hsa-mir-548d-5p, hsa-mir-548h, hsa-mir-548i, hsa-mir-548j, hsa-mir-548w, hsa-mir-548y, hsa-mir-559, hsa-mir-602, hsa-mir-214, hsa-mir-3619-5p, hsa-mir-761, hsa-mir-219-5p, hsa-mir-4782-3p, hsa-mir-2114, hsa-mir-4672, hsa-mir-124, hsa-mir-506, hsa-mir-466, hsa-mir-4323, hsa-mir-4420, hsa-mir-3662, miR-10a, miR-181a, miR-100, miR-22, miR-16, miR-21, miR-17, miR-7a |

The enriched proteins found in the five populations can be found in Table 11.

TABLE 11

Summary of genes with enriched expression in the MSC populations

| | genes |
|---|---|
| UC-MSCs Upregulated | IL8, ALDH1A1, IL11, C4ORF7, NEFM, ANXA3, LOC7309, FAM84B, HS.1557, SNCA, SYNPO2L, HAPLN1, ITGA2, C20ORF1, C4ORF49, C4ORF26, FLJ3540, LOC7282, HOXD11, SERPINB, CDCP1, PECI, HS.2531, MPP4, RHOU, STC1, SSTR1, ADAM23, OLR1, SSFA2, |

TABLE 11-continued

Summary of genes with enriched expression in the MSC populations

| | genes |
|---|---|
| | TMEM88, FAM167A, NP, PLCXD1, S1PR1, EEF1A2, ANXA8, SCG5, C16ORF7, TOX2, ARHGDIB, CCL7, CD58, LOC6528, TYRP1, SHISA3, LPXN, PLAT, HS.4067, GABBR2, HS.9138 |
| UC-MSCs Down-regulated | LOC1001, GBP2, DOCK10, LIMCH1, TNC, LOC7288, C4ORF18, CA12, KCNK2, LOC2834, ADAMTS5, PHGDH, RCAN2, CLEC14A, SMAD6, MMP1, CLIC3, NDRG1, SVEP1, KIAA119, HS.1971, ECM2, NGF, FLJ1091, FBLN2, CHST15, ABI3BP, PDGFRB, CPE, CYP1B1, DDIT4, MGP, PRRX2, CXCR7, H19 |
| CH-MSCs Upregulated | BMP3, ADORA2BA2, ISL1, ARID3A, WNT1, CKB, HSD17B2, HS.570988, BCYRN1, EGFL6, CTSC, RAB20, NKD2, HS.291319, ABCG2, IQGAP2, WFDC3, SLC16A4, LIN28B, PABPC4L, IFIH1, CXCL14, CALB2, SLPI, C4ORF7, HOXA13, IGF1R, ELOVL2, CRISPLD2, FBXO8, KYNU, PLEKHG3, PAPPA, MAEL, ATP8B4, LOC647322, ADAMTSL2, OPN3, ASAM, ANXA8, HCLS1, CD24, HS.561679, C16ORF87, ARHGAP20, ADAMTS9, ALG9, HS.163752, VTN, GATA4, SYNPO2L, GTSF1, PDLIM1, LOC100128098, MMD, EBI2, MASP1, ST6GALNAC5, HS.28367, LOC652226, FOXF, LOC100130886, FLJ22662, PTGER2, HK2, CYB5A, HGF, RSPO3, MAP3K8, CD55, IL6ST, IMPA2, LOC652846, PDPN, MCOLN2, FOXQ1, RARRES1, LOC389300, LOC100132091, LOC653879, TGFB3, SLC12A8, TMX4, FAM102B, LIFR, GALM, SYPL2, HSPA2, ABCC4, TKT, HS.25318, HS3ST1, C4ORF26, C12ORF59, NCOA7, S1PR3, PITX2, ALOX5AP, PLD1, F3, BCL3, WNT2, ACTBL2, FAM117B, RTTN, KCNK12, SOCS3, CYP2S1, LOC387856, LOC100134265, LAMA5, GPRC5A, IL24, PI3, ADAMTS19, CLDN23, CD14, IL7R, LOC100130835, ANXA8L2, FAIM3, NAMPT, MAN1A1, ITGA1, EGFLAM, SIPA1L2, FAM65C, VCAM1, SLC7A11, SARM1, TFPI, DSCR8, LXN, NID2, TFRC, TSHZ1, ABCG2, IRS1 |
| CH-MSCs Down-regulated | ITGB3, TBC1D9, ARHGDIB, HOXB7, DDAH1, RAB11FIP5, MMP14, PEA15, KLF2, KCND2, ARHGEF6, ATL1, SHRM, ZFHX4, RAGE, CLEC11A, ELOVL4, CDH13, PRRX2, DUSP23, FRMD4A, GAS6, S100A16, LOC646345, LOC643911, IGFBP7, PPP1R13L, FOXD1, COL8A2, GSTO2, NTM, SYNC1, GRAMD3, CDC42EP5, C1ORF133, FAM176A, ODZ4, SPOCK1, PTGFRN, SSPN, SPG3A, HS.19193, AHNAK2, UBE2E2, SCG5, MGC87042, C1ORF54, SRGN, SCG2, WASF3, PLXDC2, AUTS2, CTGF, TNC, GPC4, TMEM166, RGS4, PRICKLE1, ANKRD1, BGN, C10ORF116, HS.370359, HS.10862, SRPX, SCRG1, GPNMB, LTBP2, SLIT3, CRYAB, POSTN, SULF1, RAC2, CDH4, MET, KCTD20, TMEM75, C7ORF69, EDIL3, PIP4K2A, HS.71947, HOXB5, RNF150, FAM171A1, ASAP2, MEX3B, FXYD4, SYNC, HAPLN1, H2AFY2, GADD45A, LASS6, NGF, C14ORF37 |
| BM-MSCs Upregulated | DLX5, KRT81, SHISA2, ALPL, FLJ46906, CSPG4, FOXC1, LOC729708, CD24, ERRFI1, CADM1, TMEFF2, MLPH, GAPDHL6, MYBL1, PGF, TWIST1, CDK6, HS.453381, MTHFD2, ATOH8, ENPP1, KCTD15, HBEGF, COL5A3, AGTR1, FGFRL1, BAPX1, APCDD1L, STMN3, HS.551128, TNC, ITGA10, DSG2, LOC442597, TBC1D19, MGC4294, PENK, HAPLN1, TMEM132A, JAG1, SDC2, KIAA1644, PHGDH, PCNT, ITGA5, PSPH, HS.196849, WDR41, CAV1, B3GALTL, TMEM25, RNF144SH2B3, EIF4EBP1, ANXA3, GMDS, THBS3, GDF5, ASNS, BAALC, CRYBB2, SIX1, STAT4, SLC9A3R1, GPX7, SLC1A4, LOC728285 |
| BM-MSCs Down-regulated | ITGBL1, BST2, SLITRK4, IDI1, SPRY1, SLC39A8, TGM2, MANBA, IL1A, QPRT, HS.551145, MXRA5, CXCL6, FLJ35258, ANTXR1, EPDR1, GNG11, C7ORF28B, CEBPD, LOC649366, LGALS3BP, TMEM119, HOXB5, SOD2, SERPINB2, HMOX1, EBF3, PROCR, HOXB8, CREG1, FNDC1, HOXB7, CXCL1, CHURC1, C4ORF18, RSPO3, IL8, PCOLCE2, BMP6, GBP2, RDH10, GALNT12, TFPI2, TEK, MSC, F3, GSTT1, SPON2, IL6, SVEP1, DPP4, SCG2, CLDN11, CTSK, COMP, CCL2, FBLN2, IGFBP5, SHROOM4, GAST, AEBP1, C19ORF10, SCUBE3, HEG1, PITX2, PCDH18, NAAA, TPST1, ITGA1, NUPR1, RAB5A, SLC12A8, HS.579631, LOC100130835, FAM162B, MIR1978, HS.163752, C5ORF62, GANAB, ARHGEF3, PRKAR1A, C1QTNF5, LTBP2, P8, GABARAPL1, COBLL1, OLR1, PMP22, DDIT4L, RAB3IL1, LRRC17, LTBR, ABI3BP, PDLIM1, TNFRSF14, FGF2 |
| AD-MSCs Upregulated | PI16, OSR1, PNPLA7, SPATA18, HS.537004, MGC13057, CD36, CYGB, PSG4, C10ORF110, LOC654191, LOC88523, STMN2, C1S, S100A4, EMILIN2, MR1, FTHL12, TRH, LAMA4, SH3PXD2A, PLEN2, HCN4, HTR2B, AKR1C3, FNDC1, FAM65B, CCL13, NPEPL1, ECM2, IFI27, WISP2, GPAM, SLC31A2, LTBP2, ADM, PTGIS, HSPB7, ACVRL1, HIST1H2A, HLA-DPA1, FAM162B, TNFRSF11B, TMEM140, EPDR1, FBLN1, SLC1A1, HS.100261, FBLN2, ATF5, KLF4, POMZP3, HS.491292, HS. 579631, MOXD1, SGCG, ADA, LOC642567, CTSF, SLC27A1, SUSD2, EBF3, TMEM204, SRPX, LOC100134259, CLAHM2, CCL2, CYBRD1, CRABP2, PDGFD, C1QTNF5, NAGLU, SFRP1, HS.562504, LOC399888, SLITRK4, C16ORF45, RIPK3, COMP, MSX1, HIST1HIC, LGALS3, DNASE1L3, TPP1, CTSK, GPX3, IFIT1, SULF1, |

TABLE 11-continued

Summary of genes with enriched expression in the MSC populations

| | genes |
|---|---|
| | AZI2, LOC7380820, MFAP5, HMOX1, MFAP4, LPHN2, PCSK5, NUPR1, CXCR7, PLSCR4, LOC389033, LOC 647307, PLXDC2, HS.193406, SFRP2, GREM2, IGFBP6, C18ORF56, FTHL3, FTHL11, COX7A1, APBB1IP, A4GALT, VWCE, VCAN, ITGA1, IL13RA2, ECM1, NOV, LOC729009, SERINC2, TMEM100, LIMCH1, MAPK13, PSG3, FLJ10916, ARHGEF3, SPOCK1, MMP1, PLAC9, HIST2H2AC, ANXA4, BHLHB2, P76, LRRC32, TMEM119, LOC100131139, BHMT2, GPR116, PAM, PPP1R14A, PTGS1, FLJ35258, C6ORF105, KIAA1671, C6ORF145, PSG9, CD248, GDR15, GJB2, SCPEP1, FAM149B1, SLIT3, IF144, CLCA2, ITGBL1, XPNPEP2, THBS2, OLRML1, PPP1R3C, HSD3B7, NYNRIN, PSG6, HTRA1, PSG5, FBLN5, CXXL6, IFIT3, PLXND1, PCDH18, KCND2, SPINK6, DPYD, IFI6, CRIP1, ZNF521, CRLF1, TRIM22, LGMN, DACT3, AGT, GRN, DEPDC6, MN1, EMX2, PIK3IP1, ITGB5, BEST1, FBXO32, APOD, SLC15A3, TNFRSF14, SPINK5L3, STAT1, H19, RRAGD, FOLR3, FTH1, AOX1, SCUBE3, XG, MYO1D, OSBPL8, ABI3BP, C10ORF10, PPAPDC3, ADAMTSL4, SFRP4, OPTN, CTSO, SNORD13, ZDHHC1, SCARA5, OAF, NCALD, HAS1, PTGER1, SAMD9, C13ORD15, NINJ2, CDH10, SEPP1, PRG4, SAM149A, LOC651872, DPT, SLC2A5, PLAT, PRICKLE1, FBN1, MGP, GPNMB, KIAA1324L, MAPK3, TPR, EMCN, CH25H, LOC649366, IL1A RAB3IL1, AHNAK2, LOC100129550, CLEC14A, INMT, HSPB2, CCDC136, TEKT, AEBP1, C13ORF33, ANKRD37, NRBF2, LOC727768, IFI44L, CBLN3, PCOLCE2, C16ORF30, CLEC3B, PMP22, C5ORF54, FGL2, LY96, C20ORF108, HS.552087, HIST2H2AA, LOC642477, OLR1, KAZALD1, PDGFRB, TSHZ2, POSTN, RENBP, DBC1, NFIA, PPAP2B, A2M, RECK, C6ORF85, LIMS2, FABP3, LOC653506, C4ORF18, CD200E, PROS1, GSN, IFI20, C7ORF41, IFIT2, HIST1H4H, LOC440157, SERPING1, IRS2, SEMA3C, PTGDS, OLFM1, P8, CTSL1, LOXL4, LOC654096, RELN, GLB1L, PIGZ, EFEMP1, PDE1A, AK3, FAM87A, FTHL2 |
| AD-MSCs Down-regulated | LOC100134393, DSG2, ASF1B, CCNB1, SLC9A3R1, FANCI, FABP5L2, CDC2, ODC1, MATN2, CENPN, NETO2, COL4A5, H2AFZ, LOC651816, CCNB2, LOC644480, CDCA2, FBN2, CCNA2, STAT4, HNRPA1P4, PLK4, HS.497591, IQCF2, LOC388275, UHRF1, CDCA8, LOC388588, CENPV, LOC731049, PTTG3P, MAPK12, ITGA10, LOC399942, CDC45L, TBX2, LMNB1, TRIP12, KIAA0101, XYLT1, TNC, KIF20B, CEP55, AMY1C, CDC25C, CENPE, AURKA, F2RL1, MST4, NDC80, DLGAP5, LIG1, KIF23, CENPA, KIF20A, ASNS, BOP1, C6OFT173, CENPF, EPHA2, SMS, HMMR, ANLN, LSM4, FOXM1, FAM61A, CKAP2L, KLF5, LOC653874, BIRC5, EFNB2, PRELID1, HNRNPH1, MCM5, PBK, SGOL1, SPC25, TK1, PTTG1, LOC730534, LOC 731314, CADM1, AURKB, ANXA3, C15ORF23, EZR, GINS2, RRM1, TROAP, CKS2, CDC20, LOC92755, LOC 646347, KIF2C, TOP2A, SALL2, CENPM, CDCA3, PITX1, MLF1P, DNAJC9, CDT1, RANBP1, CENPK, TTK, ADORA2B, TUBB2C, CDCA5, PA2G4, TYMS, ERRFI1, FAM60A, CKS1B, KIFC1, CCT2, KIF14, KRT19, KLHDC4, MCM7, IGF2BP3, RGS4, RNASEH2A, BUB1, ATP2B4, SKA1, MELK, HS.574023, UBE2T, TPX2, PDCL3, WDR51A, UBE2C, DEPDC1B, LOC642590, CPA4, KPNA2, OIP5, MARCKSL1, ADAMTS3, POLQ, CDKN3, C12ORF24, RRM2, FOXC1, THOC3, ITM2C, KIF4A, HNRNPA1, E2F2, NUSAP1, TUBG1, GTSE1, VIL2, TUBB4Q, LOC650369, HES4, LOC643287, PAFAH1B3, TACC3, TMEM132A, ETS2, FAM83D, PENK, LOC729816, ASPM, NCAPG2, SLC2A8, TM4SF1, LOC729102, SPC24, RPL39L, HJURP, CEP135, NCAPD2, RAD51AP1, NCAPG, TMEM118, LOC717803, CBX5, PRC1, TMEM48, PRR11, NEK2, ACTG2 |
| AM-MSCs Upregulated | PPARG, NOTCH2, FGFR1, DVL1, CCND1, AQP1, C4ORF26, PLD5, ANXA8, ANXA8L2, LOC652846, PARM1, RPESP, FAM84B, D4S234E, FMOD, PRSS35, SYNPO2L, SLITRK4, CDKN2B, STXBP6, ANKRD37, TPD52L1, MFAP5, NPTX2, LOC728473, DAPK1, PDLIM3, H19, PITX2, GUCY1A3, HOXB8, CKB, CPA4, KRT19, CGNL1, ST6GALNAC3, SH3GL3, ARHGEF3, FOXQ1, ADORA2B, KCNS1, GLS, SOCS2, NMU, TNF, RIMS2, BST1, MSX1, VTN, SERPINB9, PTGES, HOXB5, B3GALNT2, CCNYL1, DCN, PXK, SIGMAR1, KAT8, FGF2, CTNNA1, COL1A1, PRRX2, ETS2, DDIT4, IFITM1, CSRP2, HS.7093, EEF1A2, SLC7A7, HS.557431, HS.334831, LYPD6B, HS.119933, CCND2, SLC12A8, ECHDC3, SESN3, PID1, LOC100128893, LOC730994, SLC9A3R1, SORT1, HS.189987, FCHSD2, C19ORF33, EDN1, TARSL2, TNFAIP3, OSAP, C11ORF67, FSTL3, PLEKHA7, SMARCD3, RIPK1, C4ORF49 |
| AM-MSCs Down-regulated | TMEM22, CNTNAP1, HS.100261, ANXA10, IL6, EMP1, KITLG, IRS1, IRX3, HOXA9, HOXA11AS, CXCL6, SERPINB2, CXCL5, ADM, ANKRD1, PLAU, MGC87042, LOC402279, IGFBP5, TMEM166, TMEM51, TNC, LOC728320, SRGN, HS.370359, EPDR1, C4ORF7, POSTN, SRPX, OPRD1, COL6A3, CLCF1, C13ORF33 CXCL12, SLFN11 |

Example 5

Different MSC Populations are Suited for Treating Specific Diseases

In vitro and in vivo studies were performed, and it was found that specific MSC populations were optimal for the treatment of various diseases due to their secreted factors and non-coding RNAs, among other reasons. Specifically, UC- and CH-MSCs showed superior therapeutic impact for treatment of glioblastoma, brain metastases, multiple sclerosis, muscle diseases, anti-aging, tumors, radiation induced injury, amyotrophic lateral sclerosis (ALS), and in conditions associated with rejection of transplanted cells, aging and radiation. UC-, CH- and AD-MSCs showed superior therapeutic impact for treatment of diabetes and muscular diseases.

Exosomes derived from these populations were found to be effective in treating the same conditions which were effectively treated by the cells from which they were derived. Further, exosomes from UC- and CH-MSCs were found to be allogeneic (similar to the cells from which they were derived), and to not express MHCII on their surface membrane. Thus, these cells and exosomes are effective "off the shelf" treatments, and are not rejected when administered allogenically.

Example 6

Different MSC Populations Exert Differential Effects on Cancer

Figure 1B:
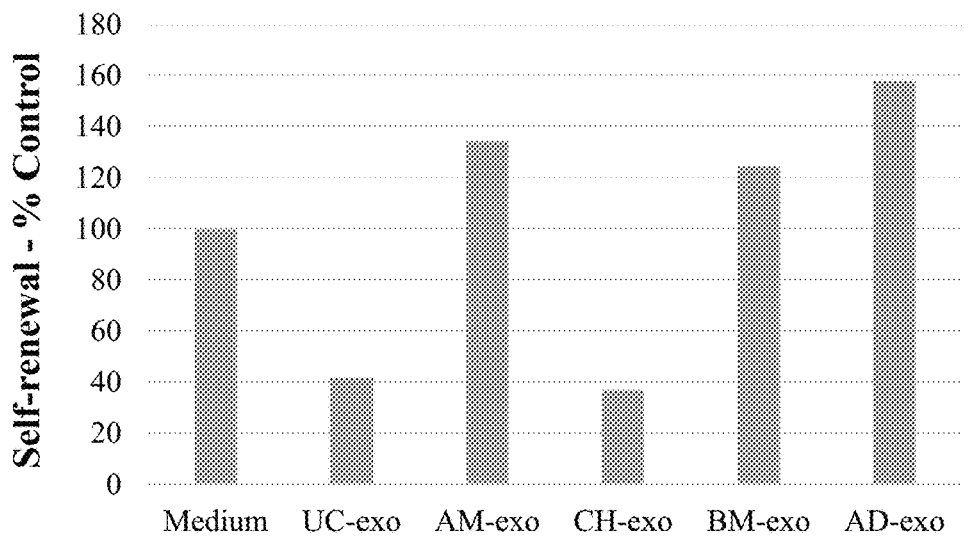
Figure 2A:
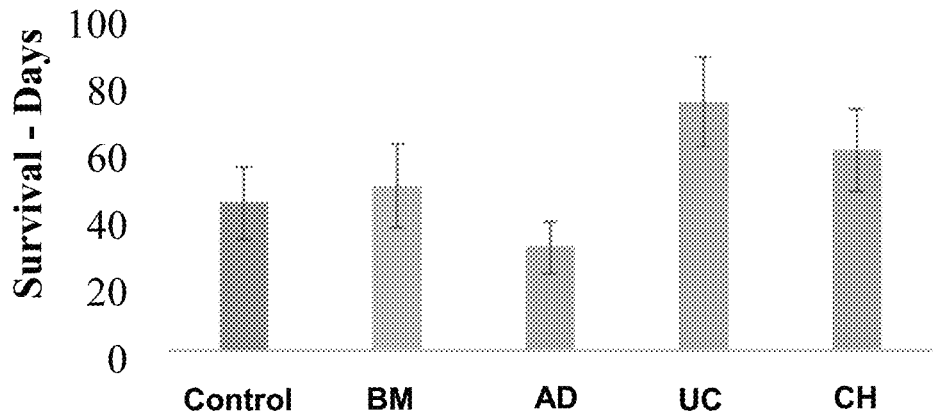
FIGS. 2A-H. MSC Population and their exosomes inhibit glioblastoma and prolong survival. (2A) A bar chart, showing survival, as measured in days, of mice receiving four different MSC subtypes or control cells. (2B) A bar chart, showing survival, as measured in days, of mice receiving exosomes from five different MSC populations or PBS as control. (2C) Survival curve of animals receiving exosomes from MSC subtypes or control. (2D) A bar chart showing the number of dead GSC after transwell coculture with MSCs or their exosomes, with and without radiation. (2E) A bar chart showing the number of dead metastatic lung and breast cancer cells after transwell coculturing with MSCs, their exosomes, with and without radiation. (2F) A bar chart of self-renewal of glioblastoma cells, and metastatic lung and breast cancer cells after transwell coculture with MSCs or their exosomes, with and without radiation. (2G) A bar chart of dead neurons and oligodendrocytes after irradiation with and without coculturing of MSCs. (2H) A bar chart showing the relative expression of pro- and anti-inflammatory cytokines after transwell coculture with UC-MSCs, irradiation or both.
Figure 2B:
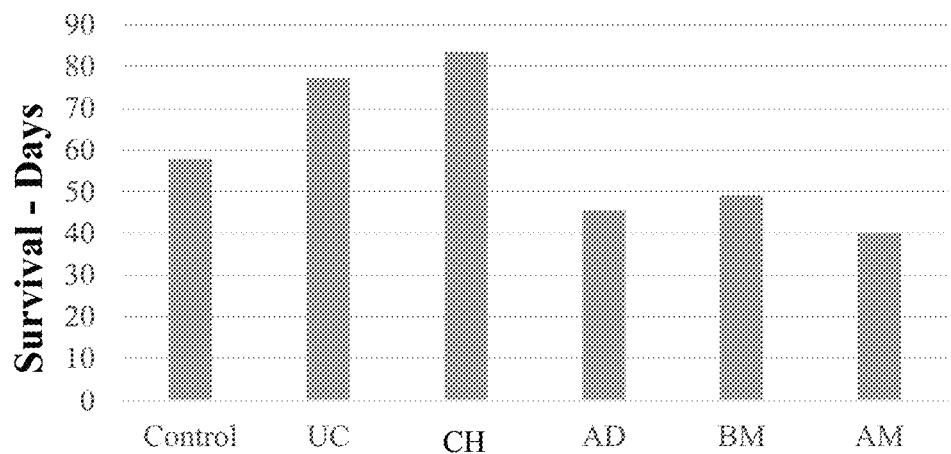
Figure 2C:
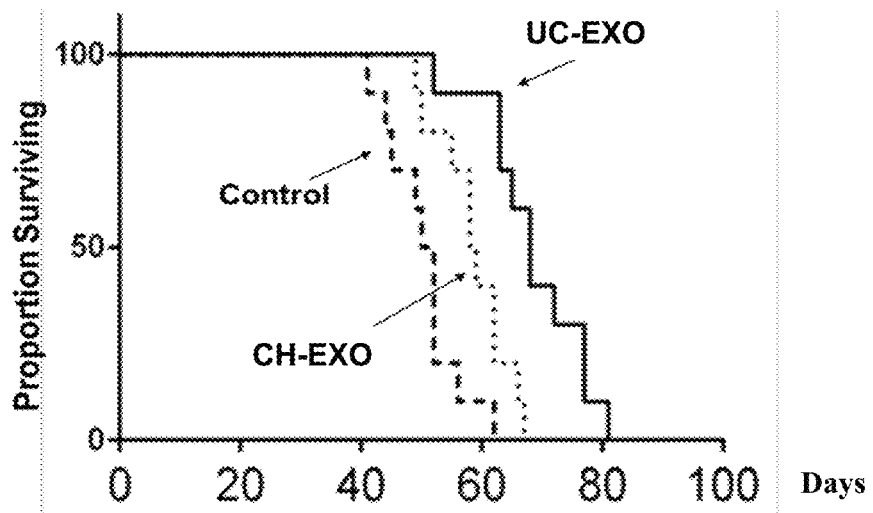

The AD-, AM- and BM-MSCs increase the self-renewal and mesenchymal markers of glioma cells and glioma stem cells (GSCs). The self-renewal ability compared to a control is shown in FIG. 1A. They also increase the migration of these cells. Their exosomes also exert similar effects (FIG. 1B). In contrast, the exosomes derived from UC- and CH-MSCs reduced self-renewal in glioma cells and glioma stem cells. Four of five markers of mesenchyme and stemness were found to be higher after treatment with AD-, AM- and BM-MSCs and lower after treatment with UC- and CH-MSCs (FIG. 1B). DP-MSCs behave similar to UC- and CH-MSCs, although with a reduced effect. Animals receiving a GSC xenograft and then treated with UC- and CH-MSCs, or their exosomes showed prolonged survival (FIG. 2A), and reduced tumor volume. In contrast, treatment with BM-MSCs had no effect on survival, whereas treatment with AD-MSC and AM-MSCs actually decreased survival (FIG. 2A). Similarly, exosomes derived from UC- and CH-MSCs exert these same anti-tumor effects and increased survival (FIG. 2B), whereas exosomes from AD-, BM- and AM-MSCs all decreased survival. (FIGS. 2B and 2C). UC- and CH-MSCs share common exosomal tumor suppressor miRNAs. These miRNAs were often found in only very low levels in the cells themselves, but were present at high levels in the exosomes. Silencing of two of these exosomal miRs, miR-145 and miR-656, in these MSCs abrogates their inhibitory effect on GSC self-renewal and migration.

Use of UC- and CH-MSCs and their exosomes to treat other forms of cancer was also investigated. Cancer cell lines derived from various tissues were plated in transwell plates, and either UC- or CH-MSCs were plated in the other well of the transwell. The percentage of dead cancer cells was calculated after 3 days of transwell culture. Both MSC populations had a positive effect on cancer cell death, though for several cancer cell lines one population was clearly superior to the other. UC-MSCs had a superior effect in breast, lung, neuroblastoma and pancreas cells. Whereas CH-MSCs had a had a superior effect in colon, prostate, lung metastasis, breast metastasis, glioma meningioma, neuroblastoma, medulloblastoma and head and neck cancer cells. As the cells were grown in transwells it is soluble factors, likely exosomes, that are responsible for this pro-death effect on cancer cells. The results of the experiments are summarized in Table 12.

TABLE 12

Anti-tumor effects

| Cancer tissue of origin | Medium only % dead | UC % dead | CH % dead |
| --- | --- | --- | --- |
| breast | 3.22 | 32.3 | 24.1 |
| lung | 5.17 | 45.2 | 37.4 |
| colon | 4.42 | 29.6 | 38.2 |
| pancreas | 2.98 | 30.2 | 22.6 |
| prostate | 6.51 | 19.5 | 28.5 |
| lung metastasis | 5.45 | 22.8 | 40.1 |
| breast metastasis | 4.2 | 19.7 | 30.22 |
| glioma | 5.5 | 26.9 | 36.33 |
| meningioma | 4.9 | 20.67 | 26.56 |
| medulloblastoma | 3.15 | 27.4 | 29.23 |
| neuroblastoma | 5.32 | 32.77 | 26.2 |
| head and neck | 2.1 | 25.4 | 29.6 |

Figure 2D:
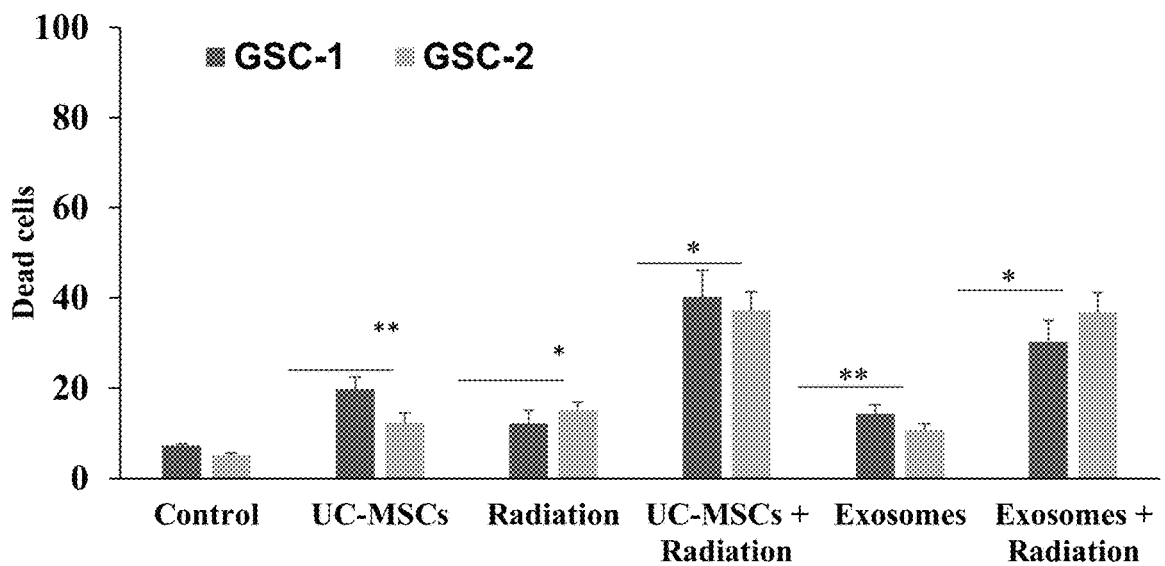
Figure 2E:
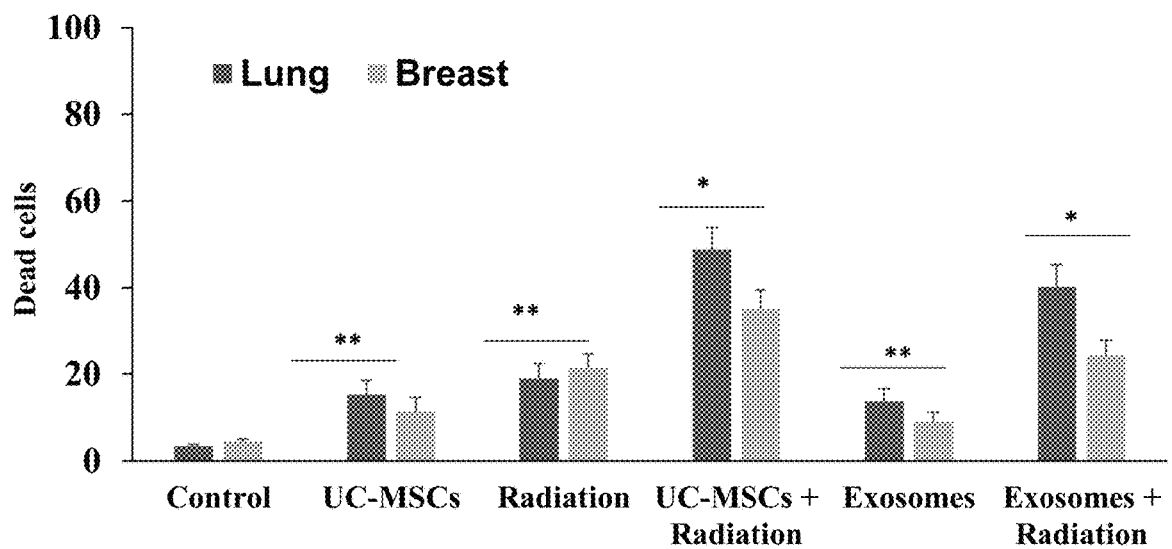
Figure 2F:
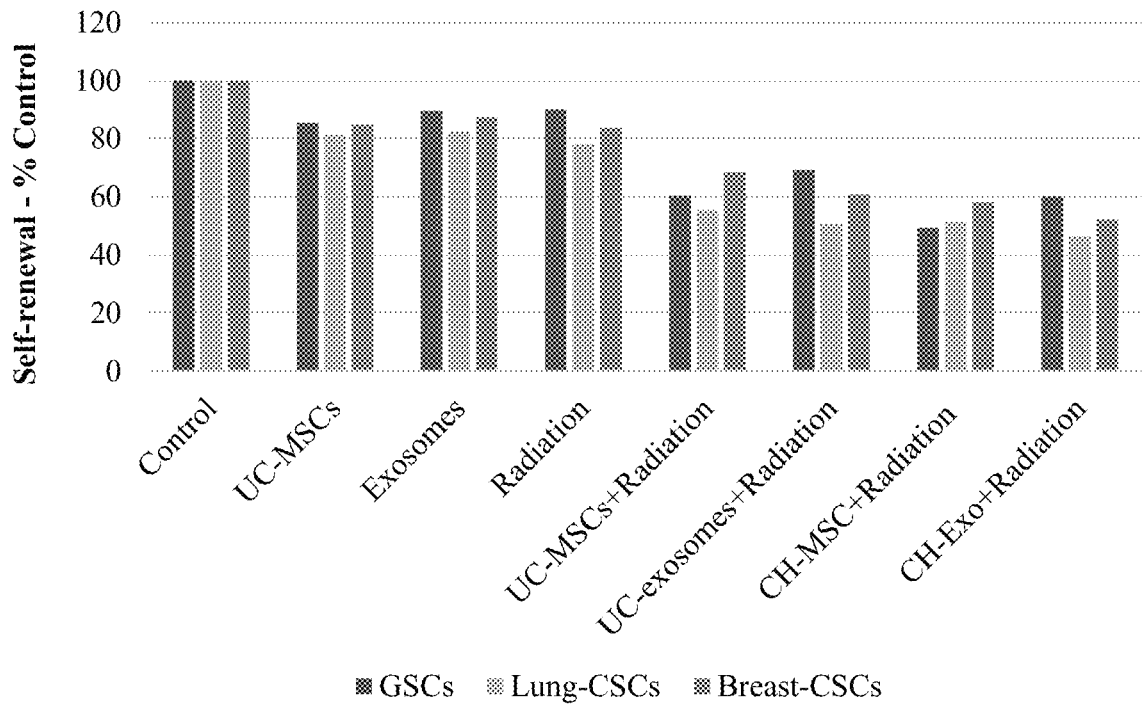

One of the treatments for GBM and other cancers is radiation. GSCs derived from two different primary gliomas were grown in transwell plates with either UC-MSCs their exosomes, or radiation alone, or a combination of the MSC/exosomes with radiation (FIG. 2D). A synergistic effect was observed when the cells or their exosomes were combined with the radiation. The same test was run on CSC from lung and breast derived brain metastases (FIG. 2E). Once again, the cells or their exosomes and irradiation had a synergistic effect on CSC death. Similarly, when an assay to measure self-renewal of the CSC was run, all three cancers investigated showed an enhanced reduction in self-renewal when the cells or exosomes were combined with irradiation (FIG. 2F). Similar results were observed with CH-MSCs and DP-MSCs. 4 Gy of radiation was used as the combination therapy.

Figure 1C:
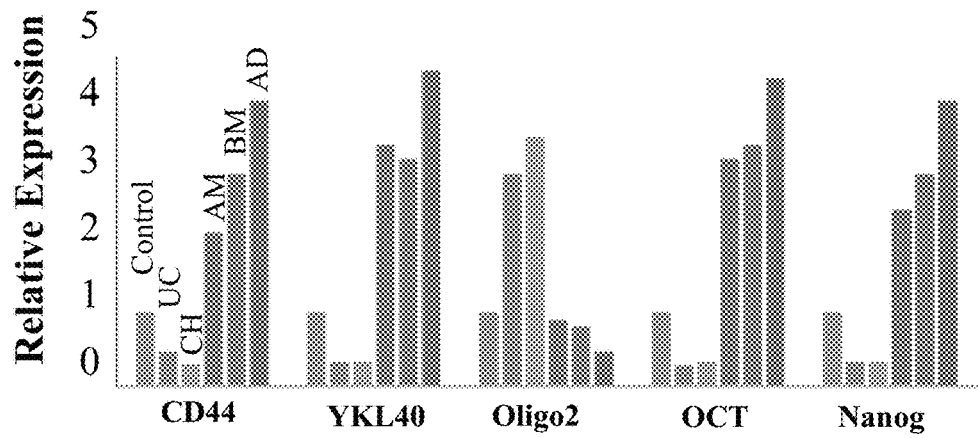
Figure 2G:
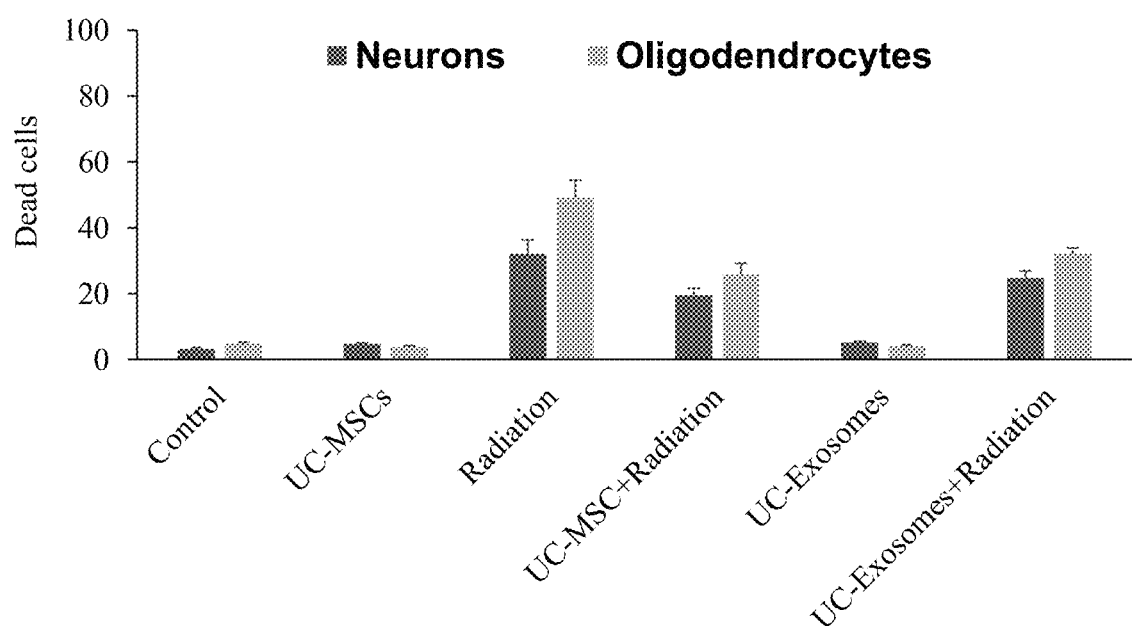
Figure 2H:
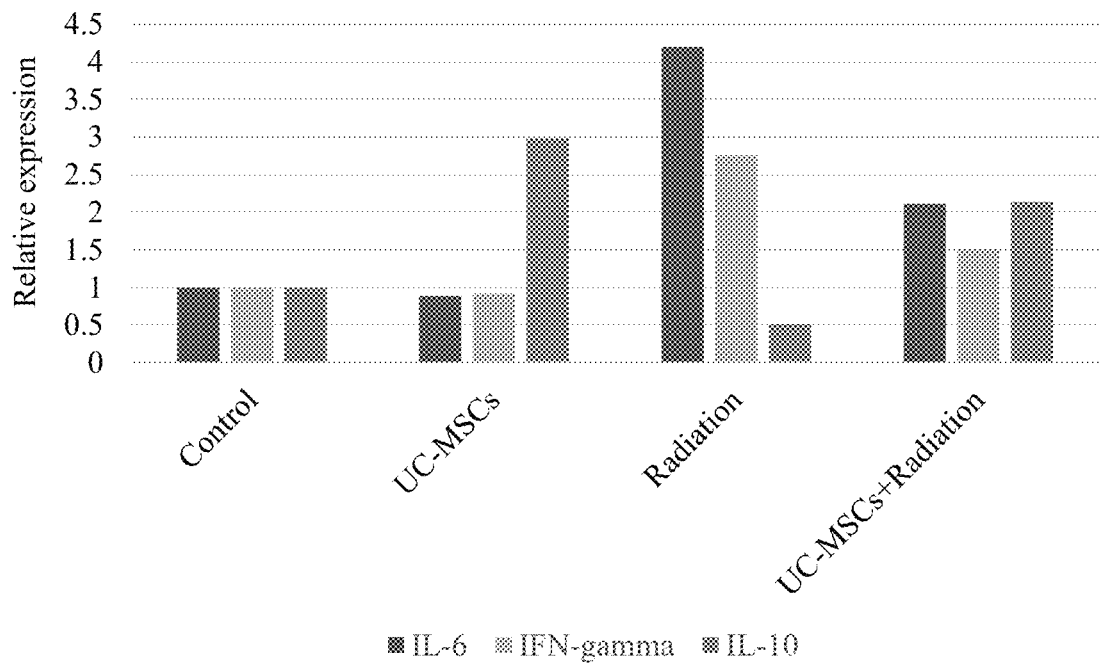

However, radiation induces neural cell injury, a side effect that causes cognition deficiency, thus limiting the dose and usefulness of radiation to treat brain cancer. It was found that the UC-, DP- and CH-MSCs not only exert anti-tumor effects they also provide protection against radiation-induced injury in part by inhibition of the M2 microglia phenotypes. Primary neurons and oligodendrocytes were cocultured with various MSC and then exposed to 4 Gy of radiation. The survival of the primary cells was measured five days later (FIG. 2G). The UC- and CH-MSCs and to a lesser extent DP-MSCs reduced the number of dead neurons and oligodendrocytes following radiation. Significantly, it was these cell populations that sensitized cancer cells to radiation (FIG. 2D-F). Microglia were also cultured either with or without UC-MSCs and then exposed to radiation. Irradiation increased expression of pro-inflammatory IL-6 and IFNγ, hallmarks of the M2 phenotype; whereas transwell coculture with UC-MSCs increased IL-10 levels, a hallmark of the M1 anti-inflammatory phenotype (FIG. 2I1). Coculture with UC-MSCs in combination with irradiation, resulted in increased expression of all 3 cytokines, however the increase in IL-6 was half as great as after radiation alone, and the IFNγ increase was also reduced. Similar effects were observed with CH-MSCS and with exosomes derived from these cells. These results suggest that the survival of healthy cells may be due to inhibition of the M2 microglial phenotype, and further than exosomes from MSCs are likely to mediate at least part of the MSC effect, as the coculture was through transwell plates.

Example 7

Different MSC Populations Exert Different Effects on Brain Metastasis

Figure 3:
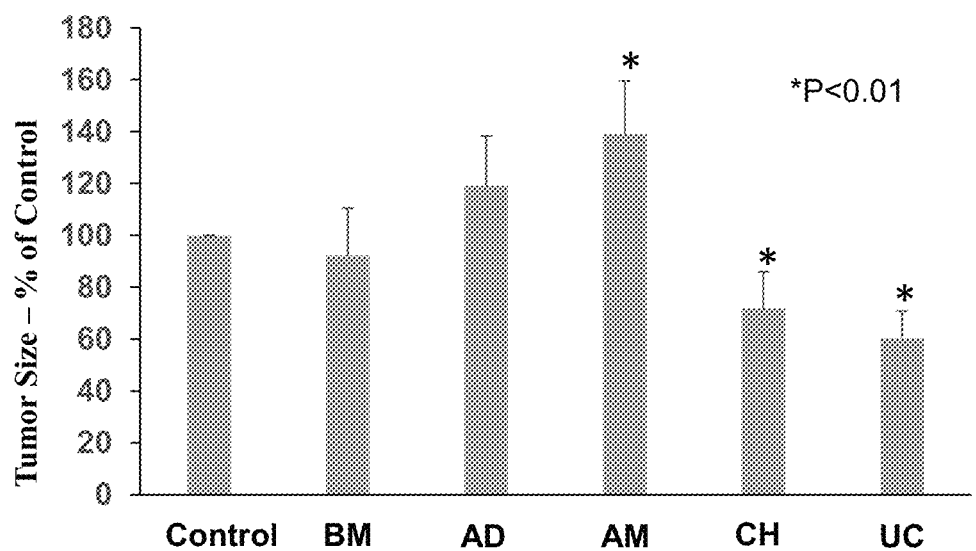
FIG. 3. MSC Populations and their exosomes inhibit brain metastasis. A bar chart of tumor size from mice with xenografts of brain metastases after treatment with five different MSC subtypes or control cells. Tumor size is depicted as the percentage of the size of the control tumor.

Xenografts of brain metastases were generated from cancer stem cells that were obtained from fresh tumor specimens of lung tumor-derived brain metastases. Twenty-one days post tumor cell implantation, different populations of MSCs were injected into the ipsilateral hemisphere (n=8), and animals were followed until they were sacrificed. The UC- and CH-MSCs decreased the size of the tumor and exerted a statistically significant increase in survival of the mice. The BM-MSCs did not have a significant effect on the size of the tumor or survival. By contract, the AD- and AM-MSCs actually increased tumor size and decreased survival, the AM-MSCs significantly so (FIG. 3).

Only UC- and CH-MSCs and their exosomes decreased tumor volume and increased survival. AD- and AM-MSCs decreased survival by about 5 days and increased tumor volume by as much as 30%. This in vivo data supports the above described results showing that UC-MSCs and their exosomes had beneficial effects on cell death and self-renewal of metastatic cells (FIG. 2D-2E).

In addition, it was found that intracranial or intranasal delivery of exosomes secreted from UC- and CH-MSCs also prolonged animal survival and decreased tumor volume. It was also found that tumor tissues after treatment with these MSCs and exosomes expressed lower levels of PCNA, which is indicative of lower cell proliferation, and lower levels of the mesenchymal transformation markers fibronectin and mouse SMA.

Example 8

Different MSC Populations Exert Different Effects on Diabetes

Figure 4A:
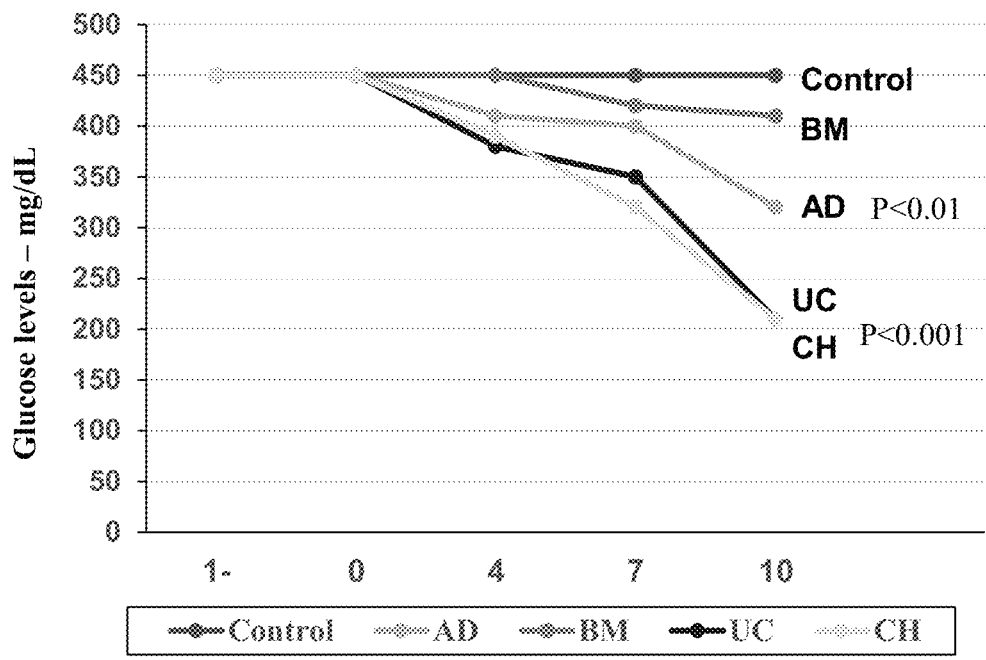
FIGS. 4A-B. MSC Populations and their exosomes lower blood glucose levels in a diabetes model. (4A) A line chart, measuring blood glucose levels in NOD mice every 2 days after administration of MSCs and control cells. Similar therapeutic effects were observed with exosomes derived from the different cells. (4B) A bar chart, showing blood glucose levels in NOD mice 10 days after administration of exosomes and PBS control.
Figure 4B:
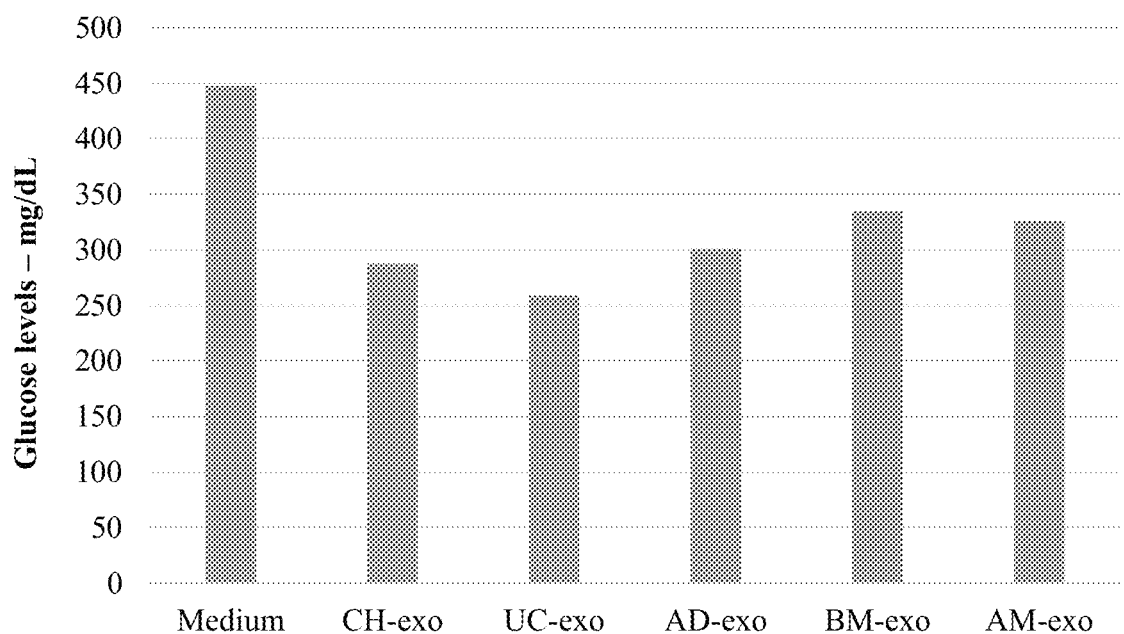

NOD mice (a mouse model of diabetes) were transplanted with 0.5 million MSCs of different populations when the mouse's glucose levels reached over 450 mg/dL. Blood glucose levels were analyzed every 2 days. The UC- and CH-MSCs induced a significant reduction in blood glucose levels, whereas AD- and AM-MSCs (data not shown) exerted a smaller effect (FIG. 4A). Similar results were obtained with exosomes derived from the different MSC populations (FIG. 4B). However, this effect was smaller than that of the cells. Exosomes were injected intravenously, and glucose levels were measured 10 days later. Once again Using in vivo imaging, it was also found that although all administered MSCs migrated to the pancreas, the BM-MSCs did not exert a significant effect on lowering glucose levels. Exosomes from the different populations were also injected and it was found that the exosomes injected into the tail vein caused some decrease in glucose levels, but to a lower level. In this case as well, the most significant effects were induced by exosomes obtained from UC- and CH-MSCs.

Example 9

Different MSC Populations Exert Different Effects on Muscle Disease

The effects of MSC and MSC exosome treatment on the muscle disease Duchenne muscular dystrophy (DMD) was examined using the MDX mouse model for DMD. Creatine phosphokinase (CPK) levels (a diagnostic marker for DMD) were analyzed in MDX mice four weeks after transplantation, by intramuscular administration to the quadriceps muscle, of different populations of MSCs. Expression of CPK was reduced by greater than 50% after treatment with UC- and CH-MSCs. AD-MSCs also reduced CPK levels by a statistically significant amount, though not to the degree of UC- and CH-MSCs. The muscle tissues were also analyzed for the expression of the pro-inflammatory cytokines IFN-gamma and TNF-alpha by RT-PCR. Only UC- and CH-MSCs yielded a decrease in inflammation in the muscle tissue, with the expression of the cytokines being reduced by greater than 50%. Neural cell adhesion molecule (NCAM) expression is a marker for muscle regeneration in MDX mice. NCAM expression levels were analyzed by immunostaining in the MDX mice's quadriceps muscle after transplantation of UC- and CH-MSC derived exosomes. Both types of exosomes increased muscle regeneration, with the number of NCAM positive cells more than quadrupling. UC- and CH-MSCs also exerted a positive effect on NCAM expression in satellite cells, in addition to the decrease in inflammatory cytokines. This effect was superior to the effect of the BM- and AM-MSCs and their exosomes.

Figure 5A:
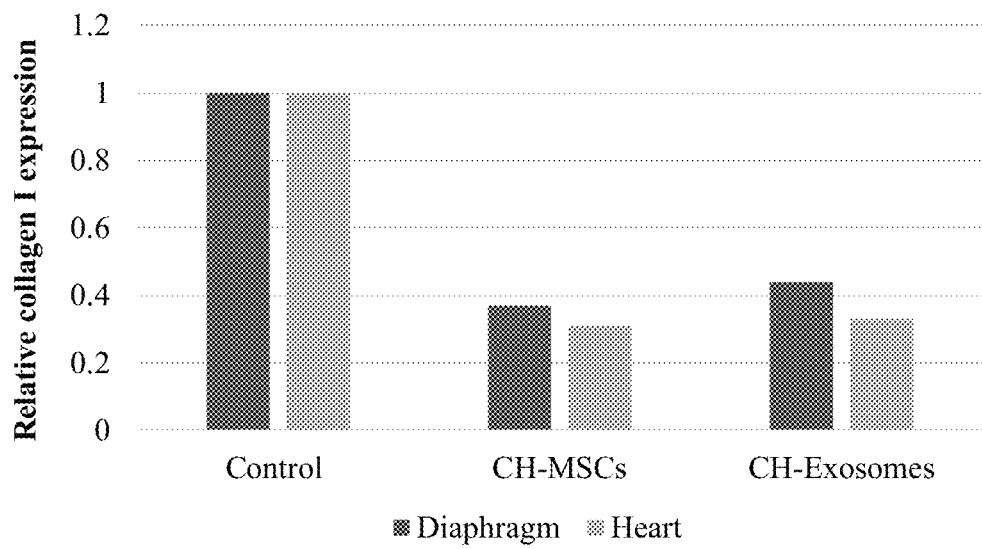
FIGS. 5A-E. MSC Populations and their exosomes for treating muscle disease. (5A) A bar chart showing collagen I expression in diaphragm and cardiac muscle in MDX mice after administration of PBS, CH-MSC, or exosome from CH-MSCS. (5B) A bar chart showing utrophin expression in diaphragm and cardiac muscle in MDX mice after administration of PBS, CH-MSC, or exosome from CH-MSCS. (5C-E) Western blot picture of Myosin heavy chain (MyHC) expression in (5C) C2C12 mouse myoblast cells, (5D) human myoblast cells and (5E) DMD myoblasts after transwell coculture with MSCs or their exosomes.
Figure 5B:
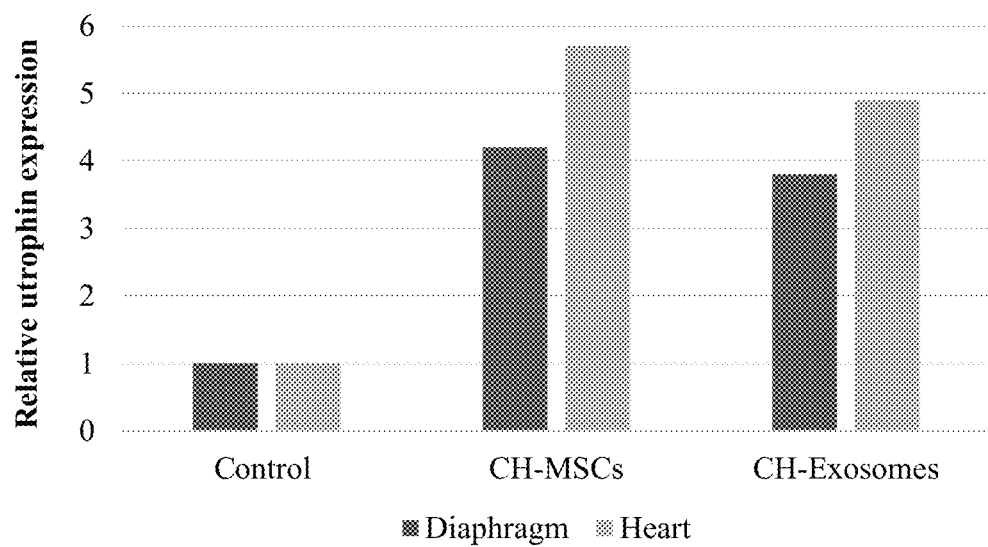

Similarly, positive results were observed when levels of collagen I were analyzed. Administration of CH-MSCs via intramuscular administration to the quadriceps muscle reduced expression of collagen I in the mouse's diaphragm and heart (FIG. 5A). Exosomes from these cells administered by the same method had the same result (FIG. 5A). An inverse correlation exists between collagen I and utrophin expression, and so utrophin expression was also measured. The expression of utrophin was increased in the quadriceps and cardiac tissues of the CH-MSC treated mdx mice (FIG. 5B). Ch-exosomes also increased utrophin expression (FIG. 5B).

Figure 5C:
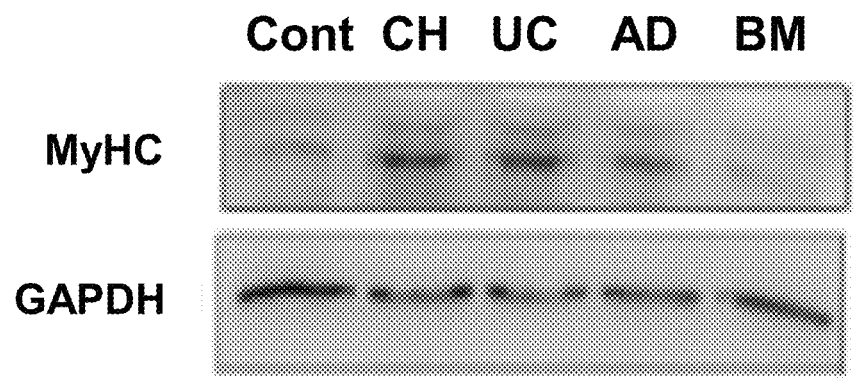
Figure 5D:
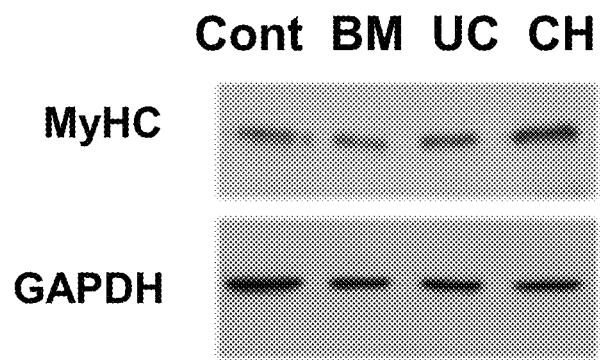
Figure 5E:
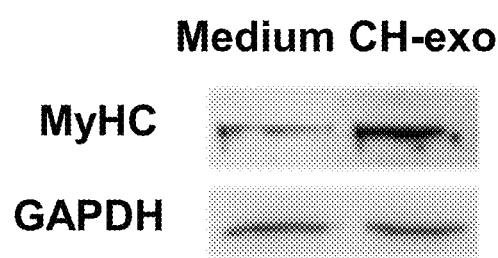

Further experiments were carried out to assess the effects of MSC exosomes on myoblasts in culture. Individual myoblasts must fuse to form a syncytium of myotubes in order to function as muscle tissue. Myoblast from healthy and DMD patients were grown in transwell culture with MSCs of the five populations and their exosomes, and a fusion index, the degree of myotube formation, was calculated. UC- and CH-MSCs and their exosomes all enhanced myotube formation of both healthy myoblasts and MDM myoblasts. AD-MSCs were able to enhance myotube formation, but only in healthy myoblasts. Myosin heavy chain (MyHC) expression was greatly increased after culture of healthy C2C12 mouse cells with CH- and UC-MSC, but less so (AD) or not at all (BM) with other MSCS (FIG. 5C). Similar results were also observed in human myoblast cells (FIG. 5D). And the effects were even more pronounced when exosomes from CH-MSCs were used (FIG. 5E). (Myosin 2 (MYH2) expression levels, a marker for skeletal muscle, were measured in control and exosome treated myoblasts by western blot. MYH2 was not detectable in the control or after BM-MSC-derived exosome culture, but was present after culture with the exosomes of the other four populations. MyoD accumulates in satellite cells during muscle repair. MyoD expression was analyzed in human satellite cells after culture with MSC exosomes of the five population. UC- and CH-MSCs-derived exosomes induced MyoD expression. The effects of these exosomes on healthy myoblasts and healthy satellite cells, suggests that exosomes (and their MSCs), especially from UC- and CH-MSCs, may be effective in treating other muscle diseases as well.

CH-MSCs exosomes contain high levels of the miR-29 family of microRNAs. BM-MSCs themselves also contain high levels of miR-29 family miRs, but the exosomes of these cells contained only low levels. Expression of the miR-29 family in muscle cell cultures from DMD patients was examined and it was found that its expression was significantly lower compared with that of muscle cultures obtained from healthy donors. Since low levels of the miR-29 family have been associated with acquisition of DMD phenotype and overexpression of these miRs promoted differentiation of myoblasts derived from mdx mice, it was hypothesized that the transfer of miR-29 by the CH-exosomes may mediate the increased differentiation of the DMD-derived myoblasts induced by the CH-MSCs.

Further it was found that CH-MSC derived exosomes could decrease the fibrogenic characteristics of DMD myoblasts. Human DMD myoblasts were incubated with CH-exosomes for 48 hr and the expression of collagen 1A and collagen 2A were analyzed using RT-PCR. The CH-exosomes decreased the expression of the two collagen isoforms. In addition, it was also found that the CH-exosomes decreased the expression of TGF-β in these cells.

Similar results were also obtained for injured muscle following treatment with cardiotoxin. Exosomes obtained from the five MSC populations were injected intramuscularly and similar results were obtained as occurred in the DMD model. It was found that injection of MSCs or their secreted exosomes to the quadriceps also decreased cell fibrosis in the diaphragm. Additionally, all MSC populations and their secreted exosomes, significantly increased the expression of utrophin in the injected quadriceps, the diaphragm and the cardiac muscle, albeit to different degrees for each tissue. Utrophin is found at the neuro-muscular junction and is essential for proper muscle function.

Example 10

Different MSC Populations Exert Different Effects on Multiple Sclerosis

To test the effects of different MSCs and their exosomes on the autoimmune, neuroinflammatory, demyelination disease, multiple sclerosis (MS), mice that were injected with pertussis toxin together with myelin basic protein (MBP) to model MS we used. The five different populations of MSCs and their exosomes were injected into the tail vein of the mice. Mice were assessed clinically for levels of paralysis using the following grading system: "0"—Normal mouse, no overt signs of disease; "1"—Limp tail or hind limb weakness, but not both; "2"—Limp tail and hind limb weakness; "3"—Partial hind limb paralysis; "4"—Complete hind limb paralysis; "5"-Moribund state, death by EAE: sacrifice for humane reasons.

Untreated animals started to exhibit disease progression already 6 days after disease induction and reached disease level of score 3 after about 14 days. UC- and CH-MSCs and to a lesser degree BM-MSCs, delayed the onset of the disease to days 13-15. However, BM-MSCs decreased disease severity only at the early stages and to a small degree. In contrast, UC- and CH-MSCs significantly decreased both disease onset and progression and mice treated with these cells exhibited a maximal clinical score of between 1 and 2. Exosomes secreted from these populations, also exhibited a similar effect, but to a lesser degree.

Figure 6:
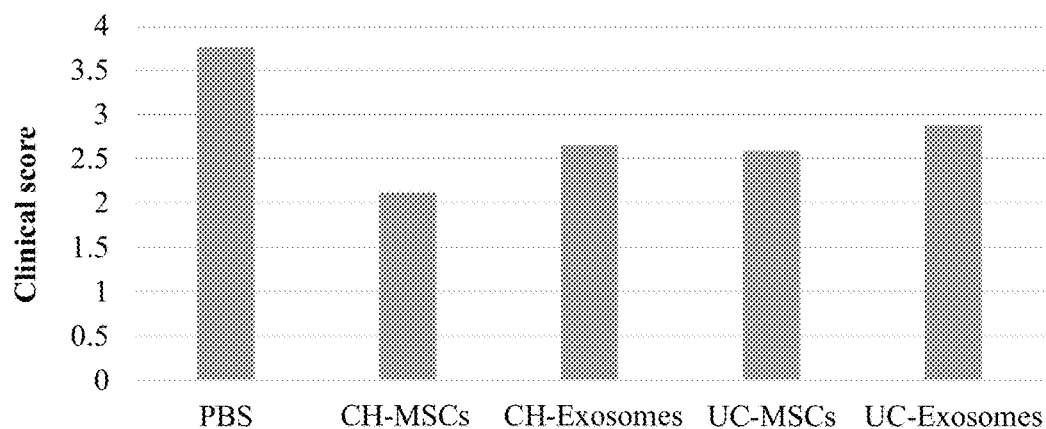
FIG. 6. MSC Populations and their exosomes exert therapeutic in a Multiple Sclerosis model. A bar chart showing the clinical score of MOG injected mice after administration of MSCs or their exosomes.

MS was further modeled using Myelin Oligodendrocyte Glycoprotein (MOG) injection. Five days after induction by MOG injection, UC- or CH-MSCs or their exosomes were administered intravenously to the mice and clinical score was evaluated at day 15 post-induction. Both types of cells and their exosomes had comparable success in improving the clinical score in the mice (FIG. 6).

Example 11

Different MSC Populations Exert Different Effects on Aging

The mouse D-galactose induced aging model (1,000 mg/kg, subcutaneously) was employed to investigate the effects of MSCs on aging. At 2 weeks following dosing, the mice were injected with MSCs ($10^6$ cells) or exosomes from the five populations and 4 weeks later the mice were sacrificed, and the skin tissue was collected and analyzed for dermal thickness and collagen quantification. It was found that treatment of the mice with any of the MSC populations inhibited, to some degree, the aging effects of D-galactose (increased thickness and collagen expression). However, UC- and CH-MSCs induced the most significant effects. Similar results were obtained with exosomes secreted from these populations.

Example 12

Figure 7A:
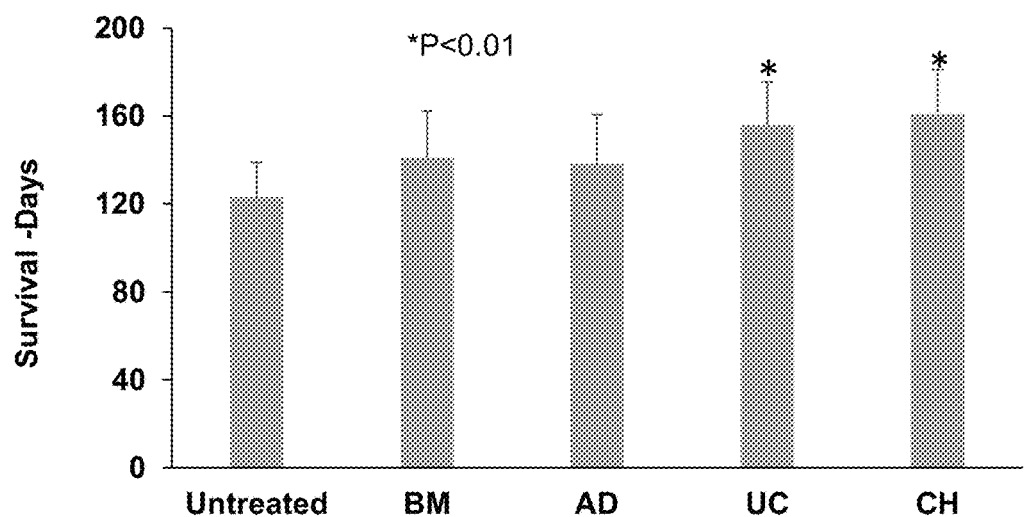
FIGS. 7A-E. MSC Populations and their exosomes for treating brain diseases. (7A) A bar chart showing survival (in days) of neurons in an ALS-rat model after administration of MSCs. (7B) A bar chart showing survival (in days) of neurons in an ALS-rat model after administration of exosomes. (7C) A bar chart showing rotational score in 6-OHDA injected mice after administration of MSCs or their exosomes. (7D) A bar chart showing the number of terminal ends of control and MeCP2-silenced neurons. (7E) A bar graph illustrating the average score on the Basso, Beattie and Bresnahan (BBB) locomotor scale of rats with and without spinal cord injury and with injury treated with CH-MSCs or their exosomes.
Figure 7B:
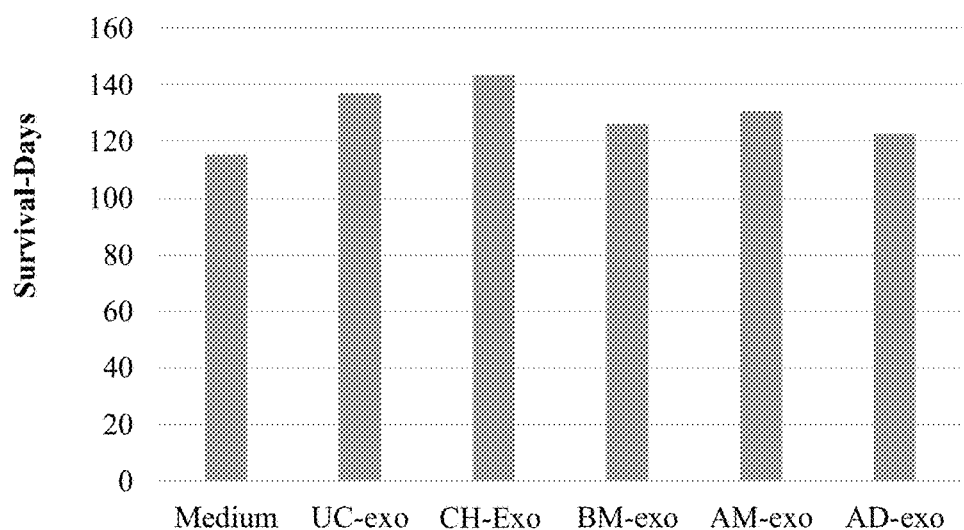

Different MSC Populations Exert Different Effects on Neuronal Disease and Injury SOD1/G93A rats (a model for Amyotrophic lateral sclerosis [ALS]) were implanted with MSCs (0.5×106 cells) at day 90 after disease onset and neuronal survival was analyzed. Only UC- and CH-MSCs significantly increased cell survival (FIG. 7A). Similar results were obtained with the exosomes of these populations (FIG. 7B).

Presymptomatic APP/PS1 mice at the age of 5 months were employed to model Alzheimer's disease. MSCs (1×106 cells) or exosomes were administered to the mice. The UC- and CH-MSCs exerted the strongest therapeutic impact followed by BM-MSCs. Specifically, a % recognition index was calculated for wild-type mice, and PBS treated control mice. The index score was decreased by 47% in the PBS-treated APP/PS1 mice. However, mice treated with CH-MSCs had only a 19% decrease, and those mice treated with CH-MSC exosomes had only a 24% decrease.

Figure 7C:
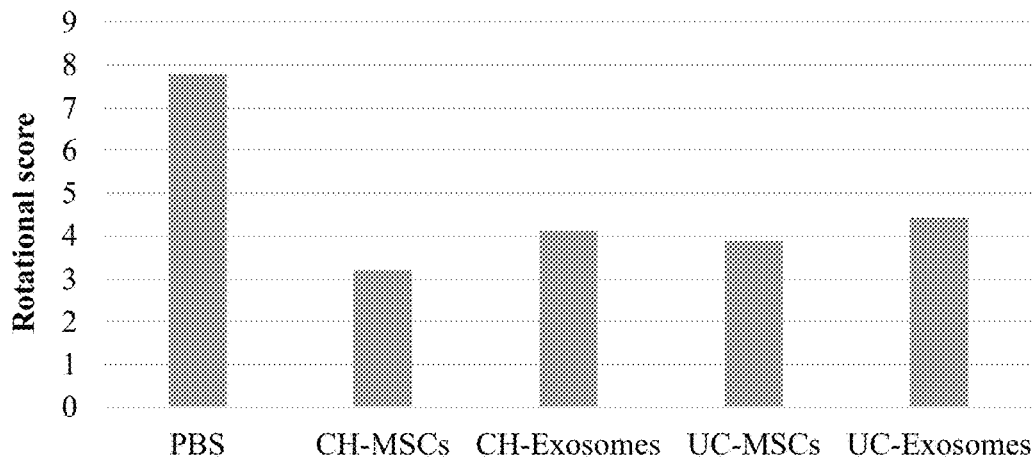

To test the effects of UC- and CH-MSC, and their exosomes, on Parkinson's disease (PD), mice were injected intrastriatally with 6-hydroxydopamine (6-OHDA) to model the disease. UC- or CH-MSCs or their exosomes were then injected either intrastriatally or intranasally. Two weeks after treatment the mice were analyzed using the apomorphine-induced rotation test, wherein a lower score indicates fewer PD associated brain lesions. Treatment with UC- and CH-MSCs, and their exosomes all resulted in significant improvement in this PD associated symptom (FIG. 7C).

UC- and CH-MSC, and their exosomes were cocultured in transwell plates with MeCP2 silenced neurons and control neurons in order to assess the ability to treat Rett syndrome.

Figure 7D:
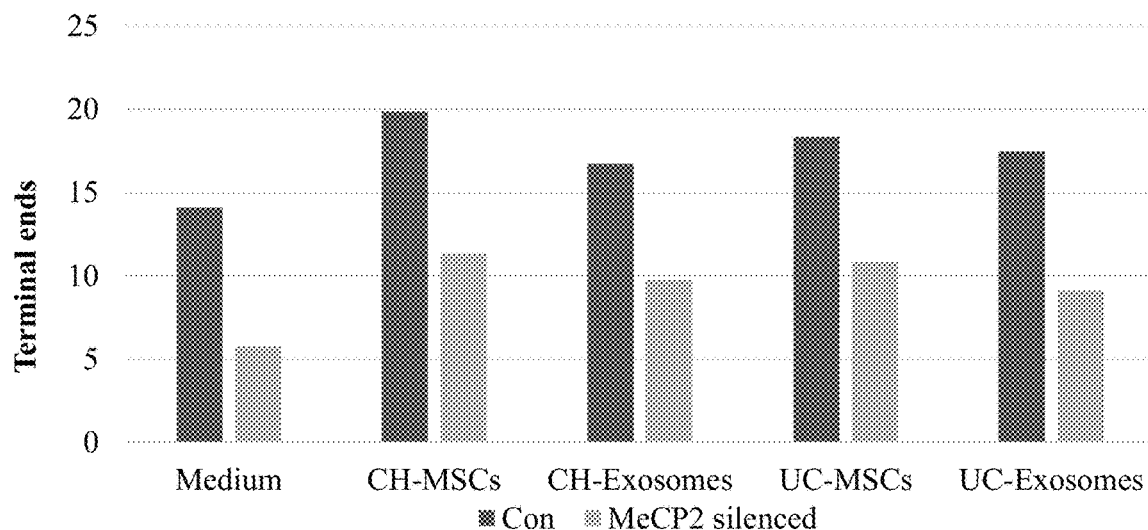

MeCP2 silenced neurons (Rhett is caused by mutations in the MeCP2 gene) had 59% fewer neuronal terminal ends than did control neurons grown without coculture. Coculture of control neurons with the MSCs or their exosomes increased the number of axonal termini by as much as 40% (FIG. 7D). In silenced neurons the increase was even greater, with both UC- and CH-MSCs causing a greater than 85% increase in terminal ends. Exosomes from these cells had a similar, though lesser effect.

To test the ability of CH-MSCs and their exosomes to treat spinal cord injury, wild-type rats underwent spinal cord perfusion injury by blocking the abdominal aorta below the left renal artery for 15 minutes. The injured rats were then treated with PBS CH-MSCs ($1\times10^7$ cells) or their exosomes injected at the L5-L6 segment of the spine. Four days later lower limb movement in the rats was evaluated using the Basso, Beattie and Bresnahan (BBB) locomotor scale method. Uninjured rats were also evaluated as a control. The BBB scale is a well-established and discriminating method for measuring behavioral outcome and for evaluating treatments after spinal cord injury. The scale ranges from zero to 21, with a higher score indicating superior movement. The scoring can be summarized by the following breakdown:

0-7: Isolated joint movements with little or no hindlimb movement.
8-13: Intervals of uncoordinated stepping.
14-21: Forelimb and hindlimb coordination.

Figure 7E:
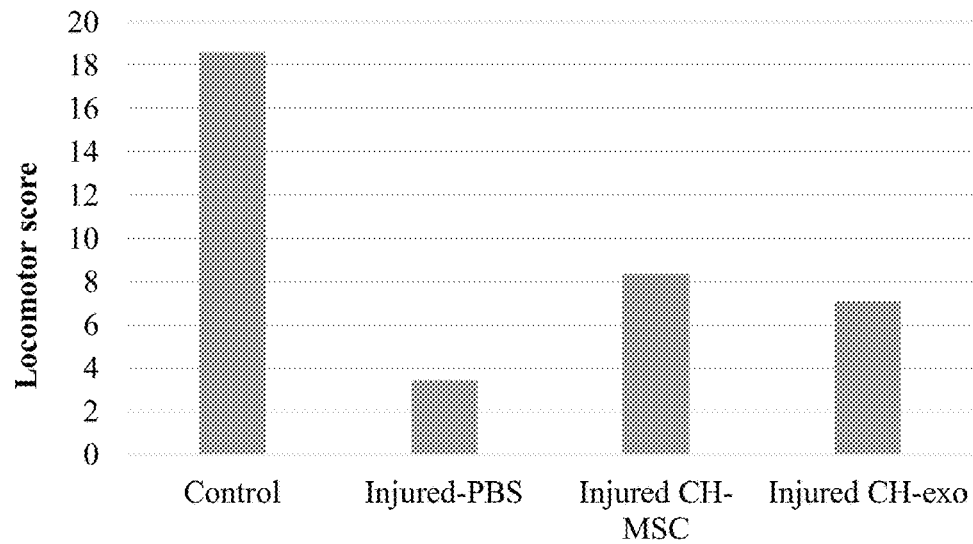

As can be seen in FIG. 7E, uninjured mice had a healthy score of 18.6 on the BBB scale, whereas control injured mice treated with only PBS scored in the lowest category with an average score of 3.46. Mice treated with CH-MSCs showed a strong improvement in locomotion, with an average score of 8.35, while treatment with exosomes had a slightly smaller though comparable effect.

Example 13

Different MSC Populations Protect from Radiation and Hypoxia Induced Injury

Figure 8A:
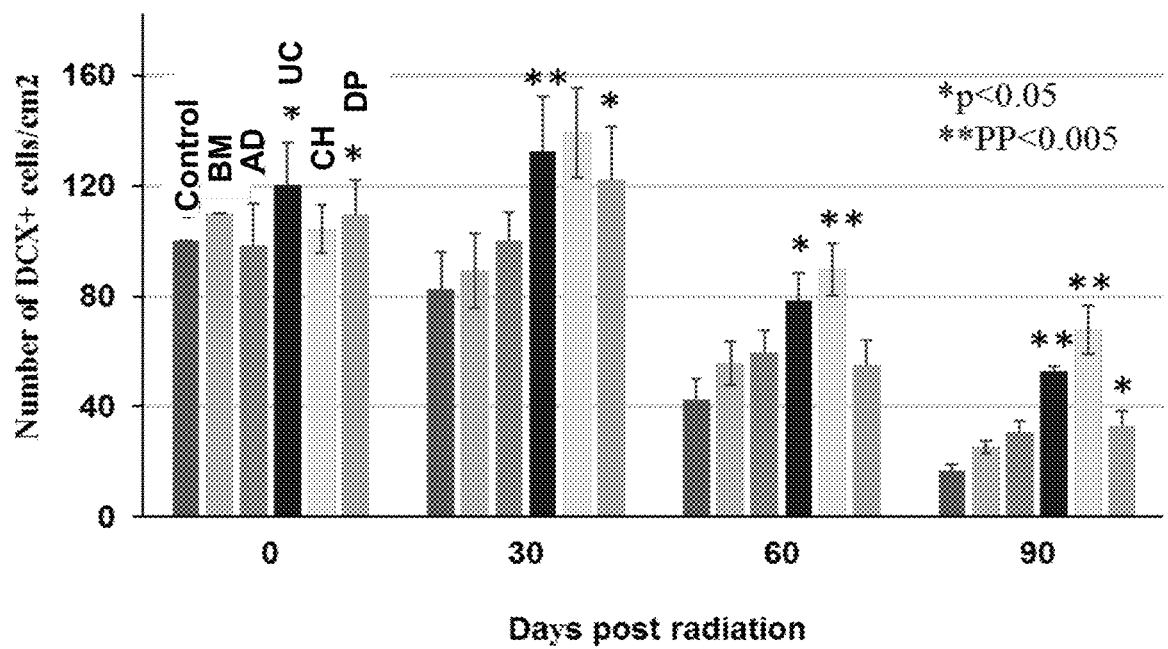
FIGS. 8A-B. MSC Populations and their exosomes protect neurons after radiation. (8A) A bar chart, depicting density of double cortin positive (DCX+) cells (that represent immature neurons) in the subvetricular zone (SVZ) of control and irradiated adult male rats 30, 60 and 90 days following fractionated irradiation with a total dose of 4-5 Gy. The populations of MSCs administered at each time point are presented in the following order: Control, BM, AD, UC, CH, DP. (8B) A bar chart, depicting density of double cortin positive (DCX+) cells in the subvetricular zone (SVZ) of control and irradiated adult male rats 60 days following fractionated irradiation with a total dose of 4-5 Gy. Exosomes were administered.
Figure 8B:
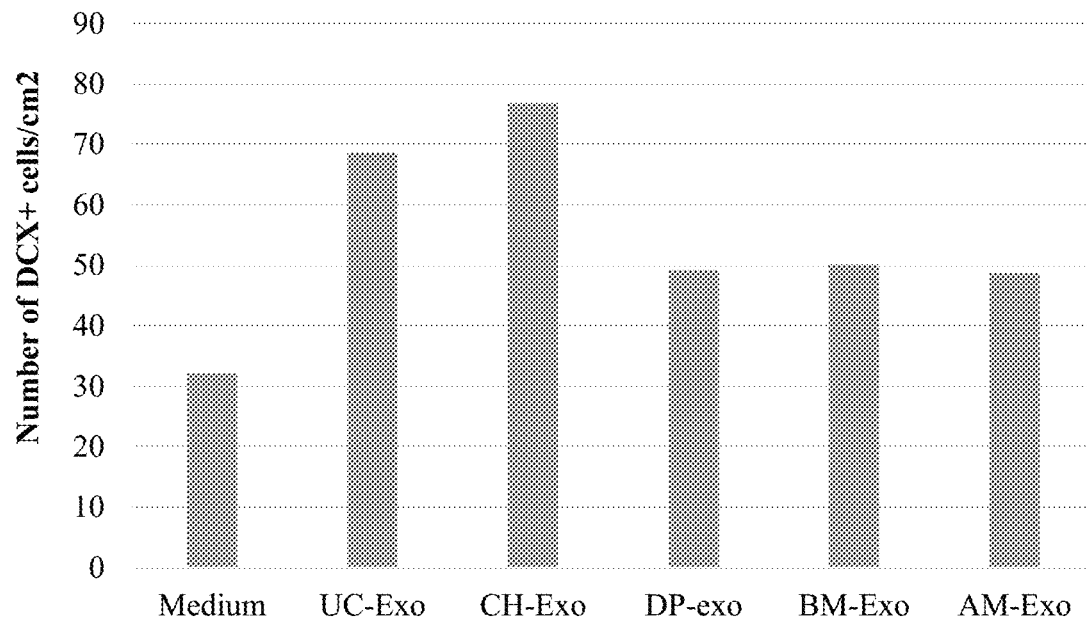

The five MSC populations, or exosomes derived from them, were administered to mice one day prior to irradiation of the brain. The number of immature neurons (positive for double cortin) were analyzed 30, 60 and 90 days after irradiation and administration of MSC (FIG. 8A). After administration of exosomes immature neurons were measured only at day 60 (FIG. 8B). The density of immature neurons was reduced after irradiation and the effects became more severe over time. UC-, CH- and DP-MSCs and their exosomes had a protective effect on the immature neurons and the density of those neurons were statistically significantly increased at all time points tested.

Administration of the cells 1-6 days post irradiation was still able to protect the brain from the radiation-induced injury as determined by the increase in active microglia cells and a decrease in the number of immature neurons. Similar to what was found when populations were administered one day prior to irradiation, UC-, CH- and DP-MSCs exhibited the strongest protective effect. However, BM- and AD-MSCs also exerted some effect when administered post-irradiation. In contrast, only exosomes derived from UC-, and CH-MSCs exerted a significant protective effect when administered post radiation. Interestingly, the MSC populations and their secreted exosomes, also protected the brain from radiation-induced injury when the brain was irradiated in a total dose of 20 Gy, which was delivered once a week for 3 weeks. These results are in agreement with those presented in FIG. 2G.

Figure 9:
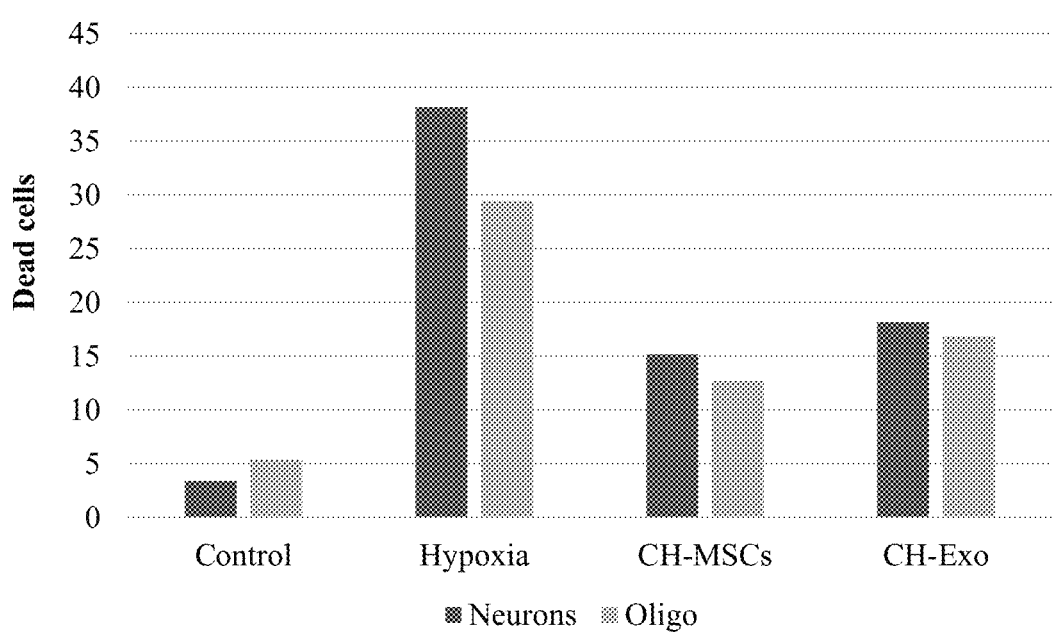
FIG. 9. MSC Populations and their exosomes protect neurons from hypoxia. A bar chart showing dead neurons and oligodendrocytes in normoxia and severe hypoxia, with and without CH-MSCs or their exosomes.

Primary neurons and oligodendrocytes were cocultured with CH-MSC or their exosomes and then exposed to severe hypoxic conditions (flow rate of 0.47 L/min air and 4.23 L/min $N_2$. Cell death of the primary cells was measured three days later (FIG. 9). The CH-MSCs and their exosomes reduced the number of dead neurons and oligodendrocytes following radiation.

Example 14

Different MSC Populations Protect Cells from Rejection During Transplant

The administration of allogenic neural stem cells, neurons, astrocytes, microglia and oligodendrocytes has been employed recently as a replacement therapy in various neuronal disorders. However, these procedures are complicated by the problems of cell rejection and impaired engraftment. It was found that the co-transplantation of these cells with t UC-, and CH-MSCs, and to a lesser degree their secreted exosomes, can minimize allogenic tissue rejection and improve engraftment and decrease cell apoptosis. In these experiments, allogeneic neural cells labeled with GFP from either human origin or from mice with a different genetic background were transplanted into recipient mice. For the allogeneic model C57BL/6J mice received primary astrocytes labeled with GFP from FVN/N H2 mice. Mouse or human astrocytes were injected intracranially into the spinal cord alone or with UC-, or CH-MSCs (2×105 each) and the animals were maintained for 3 weeks. The mice were sacrificed and the percentage of GFP labeled cells in the spinal cord were determined. It was found that both human and mouse MSCs spread in very low and negligible numbers in the spinal cord (3±0.46 cells/cm2). In contrast, co-administration of both astrocytes (mouse or human) with either UC-, or CH-MSCs significantly increased the number of the labeled astrocytes to survive (19±2.9 for UC-MSCs and 23±3.78 for the CH-MSCs).

Similar results for UC-, and CH-MSCs and their exosomes was observed for the transplanting of allogeneic islet cells for the treatment of diabetes.

Similarly, human myoblasts, satellite cells or mouse myoblasts (C2C12 positive) labeled with GFP were implanted into mice intramuscularly with and without MSCs from the five populations. The number of GFP-positive cells remaining in the muscle after 1 week and 4 weeks was determined. Transplantation without MSCs resulted in foreign human and mouse cells being eliminated from the muscle after 1 week. When the cells were transplanted with UC-, or CH-MSCs the degree of rejection was significantly decreased, and cells were observed in the muscle up to the 4-week time point. Transplantation with exosomes derived from these populations had a similar effect, with GFP-positive cells remaining after 4 weeks.

It was observed that AD-, and AM-MSCs secreted miRNAs that increased the epithelial to mesenchymal transition (EMT) process, whereas UC-, and CH-MSCs expressed high levels of miRNAs that are tumor suppressors. Similarly, UC-, and CH-MSCs secrete and express tumor suppressor long non-coding RNAs. Incubation of AD-, and AM-MSCs with tumors cells increased the expression of EMT markers such as YKL40, fibronectin and CD44 (FIG. 1A). Incubation with these MSCs also increased stemness markers such as SOX2, OCT4 and Nanog. Similar results were obtained with exosomes derived from these populations. Injection of immuno-deficient mice with AM-MSCs together with human tumor cells labeled with GFP resulted in larger and more infiltrative tumors than injection of the tumor cells alone. And as was seen therapeutically with UC-, and CH-MSCs, transplantation of human tumor cells with AM-MSCs decreased rejection of the tumor cells, even in mice that were not immune compromised.

Example 15

MSCs Alter Gut Microbiota

Gut microbiota play an important role in a variety of diseases including digestive, energy homeostasis, and neurological disease. CH and UC-MSCs and their exosomes were administered to NOD mice for 8 weeks and control mice received PBS. The cells and exosomes similarly altered the gut microbiota, increasing the abundance of Bacteroidetes, decreasing the abundance of Firmicutes and altering the Firmicutes/Bacteroidetes ratio.

Example 16

MSC Populations Enhance the Growth of Stem Cells and Primary Cells

Similar to the ability to protect cells from rejection, it was found that all MSCs, their exosomes and media from those cells (which includes the ECM) enhanced the survival of stem cells and primary cells in culture. One of the major limitations in growing primary cultures and stem cells is the difficulties in maintaining these cells for many passages before they undergo senescence, autophagy and/or other processes that impair normal and healthy growth and differentiation. Primary neurons, astrocytes, and skeletal muscle cells were plated with either conditioned media from MSCs, their exosomes or ECM derived from the MSCs and the ability of the cells to grow and divide was monitored. It was found that for all three cell types, and all three treatments increased survival in culture and allowed for healthy maintenance for a greater number of passages regardless of the MSC used. However, UC- and CH-MSCs had a noticeably stronger effect. Similarly, neural stem cells and muscle satellite cells also showed increased survival and further maintained their ability to undergo symmetric and asymmetric division.

Although the invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims.

The invention claimed is:
1. A method of treating a neurological disease in a subject selected from amyotrophic lateral sclerosis (ALS), Parkinson's disease, Rett syndrome, multiple sclerosis (MS), stroke, cerebral palsy and spinal cord injury, the method comprising:
  i) receiving exosomes extracted from autologous or allogeneic chorionic placenta-derived mesenchymal stem cells (CH-MSCs), wherein said CH-MSCs are isolated from a placenta tissue, wherein said isolation comprises selecting at least one cell expressing at least one surface marker selected from the group consisting of TCR alpha-beta, CD55, LIFR, ST6GALNACS, and MIC A/B, and optionally further comprising confirming expression of said at least one surface marker on the surface of said isolated CH-MSCs; and
  ii) administering to said subject a pharmaceutical composition comprising said exosomes, and a pharmaceutically acceptable carrier, wherein said composition is administered by an intravenous, intracranial, intraarterial, intraventricular, intraparenchymal, intrathecal, intraspinal, intrastriatal, intradural or intranasal route of administration; thereby treating said neurological disease.
2. The method of claim 1, wherein said disease is selected from the group consisting of amyotrophic lateral sclerosis (ALS), Parkinson's disease, Rett syndrome, multiple sclerosis (MS), stroke, and cerebral palsy.
3. The method of claim 1, wherein said population of CH-MSCs is substantially devoid of amniotic placenta-derived MSCs (AM-MSCs).
4. The method of claim 1, wherein said disease is ALS.
5. The method of claim 1, wherein said disease is Rett syndrome.
6. The method of claim 1, wherein said disease is Parkinson's disease.
7. The method of claim 1, wherein said disease is MS.
8. The method of claim 1, wherein said disease is stroke.
9. The method of claim 1, wherein said disease is cerebral palsy.
10. The method of claim 1, wherein said disease is spinal cord injury.
11. The method of claim 1, wherein said pharmaceutical composition comprises exosomes purified from autologous or allogeneic CH-MSCs or isolated autologous or allogeneic CH-MSC derived exosomes.
12. The method of claim 1, wherein said CH-MSCs are grown in hypoxic conditions, incubated in medium with low pH, exposed to radiation, or any combination thereof, prior to exosome extraction, so as to increase the yield of said exosomes in the pharmaceutical composition.
13. The method of claim 1, wherein said CH-MSCs are autologous to said subject.
14. The method of claim 1, wherein said CH-MSCs are allogeneic to said subject.
15. The method of claim 1, wherein said administration is selected from the group consisting of intravenous, intranasal, intraspinal and intrathecal administration.
16. The method of claim 1, wherein said CH-MSCs are not differentiated at the time of exosome extraction.
17. The method of claim 1, wherein said population of CH-MSCs is substantially devoid of cells that are not mesenchymal stem cells.
18. The method of claim 1, wherein said pharmaceutical composition comprises purified exosomes having less than 1% CH-MSCs.

* * * * *